United States Patent [19]
Chattopadhyaya

[11] Patent Number: 5,721,350
[45] Date of Patent: Feb. 24, 1998

[54] DEUTERATED NUCLEOSIDES

[76] Inventor: Jyoti Chattopadhyaya, Storgatan 20, S-753 31 Uppsala, Sweden

[21] Appl. No.: 356,168

[22] PCT Filed: Jun. 18, 1992

[86] PCT No.: PCT/SE92/00450

§ 371 Date: Feb. 14, 1995

§ 102(e) Date: Feb. 14, 1995

[87] PCT Pub. No.: WO93/25566

PCT Pub. Date: Dec. 23, 1993

[51] Int. Cl.$^6$ ............... C07H 19/00; C07H 21/00
[52] U.S. Cl. ............ 536/22.1; 536/23.1; 536/27.1; 536/28.1; 536/28.6
[58] Field of Search ................ 536/22.1, 23.1, 536/27.1, 28.6, 28.1

[56] References Cited

FOREIGN PATENT DOCUMENTS 1081217  7/1980  Canada.

OTHER PUBLICATIONS

Pathak et al. "A Regio and Stereoselective Synthesis of 2',2",3',4'-Tetradeuterio-2'-Deoxy Nucleosides" Tetrahedron, vol. 43, No. 18, pp. 4227–4234, 1987.

Serianni et al. "Stereoselective Deuterium Exchange of Methylene Protons in Methyl Tetrofuranosides: Hydroxymethyl Group Conformations in Methyl Pentofuranosides", J. Organic Chemistry, vol. 48, No. 10, 1983.

Adkins et al, Hydrogenation of Esters to Alcohols over Raney Nickel. I, J. Am. Chem. Soc., vol. LXIX, p. 3039, Dec. 1947.

Ramsey et al, Dissociation Constants of Some Substituted Phenyltrimethylammonium Perchlorates in Ethylene Chloride; Effect of Ion Asymmetry, J. Am. Chem. Soc., vol. LXIX, p. 3041, Dec. 1947.

Kondo et al, A Direct Assignment of All Base and Anomeric H1' Signals in the Proton Spectrum of a Trinucleoside Diphosphate, ApApA: Structure Implications, Febs Letters, vol. 53, No. 2, p. 213, May 1975.

Kondo et al, Conformational Properties of Adenylyl-3'→ 5'-adenosine in Aqueous Solution, Biochemistry, vol. 15, No. 4, p. 756, 1976.

Lee et al, Conformational Properties of Dinucleoside Monophosphates in Solution: Dipurines and Dipyrimidines, Biochemistry, Vo. 15, No. 16, p. 3627, 1976.

Ezra et al, Conformational Properties of Purine–Pyrimidine and Pyrimidine–Purine Dinucleoside Monophosphates, Biochemistry, vol. 16, No. 9, p. 1977, 1977.

Koch et al, A Novel Method for Specific Labelling of Carbohydrates with Deuterium by Catalytic Exchange, Carbohydrate Research, vol. 59, 1977.

Synthesis and Proton Magnetic Resonance Spectrum of a Selectively Deuterated Dinucleoside Monophosphate, Adenylyl-(3'-5')-adenosine, Journal of the American Chemical Society, vol. 94, No. 14, pp. 5121–5122, Jul. 12, 1972.

Kondo et al, The Chemical and Enzymatic Syntheses of Specifically Deuterated Dinucleoside Monophosphates, Journal of Labelled Compounds, vol. IX, No. 3, pp. 497–507, 1973.

Balza et al, Application of Catalytic, Hydrogen—Deuterium Exchange in $^{13}$C.–n.m.r. Spectroscopy, Carbohydrate Research, vol. 59, pp. C7–C11, 1977.

Angyal et al, Selective Deuteration Over Raney Nickel in Deuterium Oxide: Methyl Glycosides, Carbohydrate Research, Vo. 157, pp. 83–94, 1986.

Wu et al, Stereoselective Deuterium Exchange of Methylene Protons in Methyl Tetrofuranosides: Hydroxymethyl Group Conformation in Methyl–Pentofuranosides, J. Org. Chem., vol. 48, pp. 1750–1757, 1983.

Pathak et al, A Regio and Stereoselective Syntheses of 2',2",3',4'-Tetradeuterio-2'-Deoxy Nucleosides, Tetrahedron, vol. 43, No. 18, pp. 4227–4234, 1987.

Brush et al, Selective Deuteriation as an Aid in the Assignment of H NMR Spectra of Single–Stranded Oligodeoxynucleotides, J. Am. Chem. Soc., vol. 110, pp. 4405–4408, 1988.

Primary Examiner—Nathan M. Nutter
Attorney, Agent, or Firm—Browdy and Neimark

[57] ABSTRACT

Deuterated nucleotide and nucleoside units are used to synthesize strands of RNA and DNA wherein one unit is non-deuterated, with adjacent units deuterated. The deuteration is sufficiently high in order that resonance from the deuterated units do not overlap with resonances from non-deuterated units in NMR-experiments. Thereby a "NMR"-window is created in the DNA or RNA strands, which can be beneficially used for advanced studies of structure versus biological activity in DNA and RNA.

19 Claims, 51 Drawing Sheets

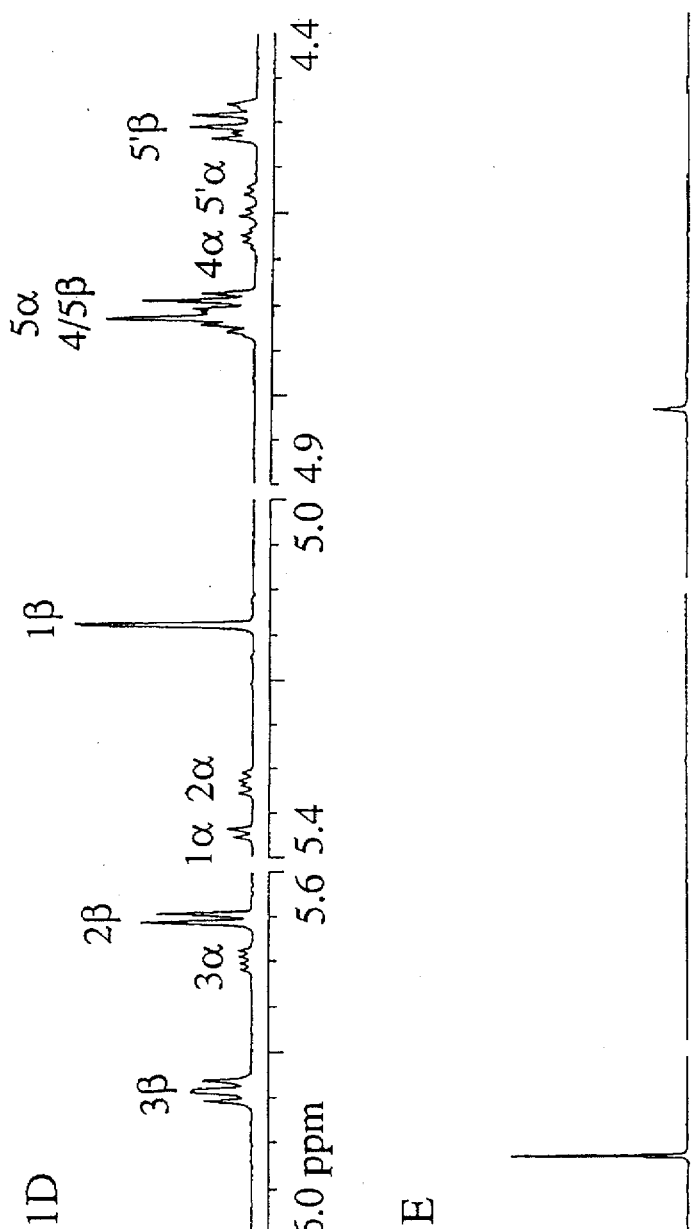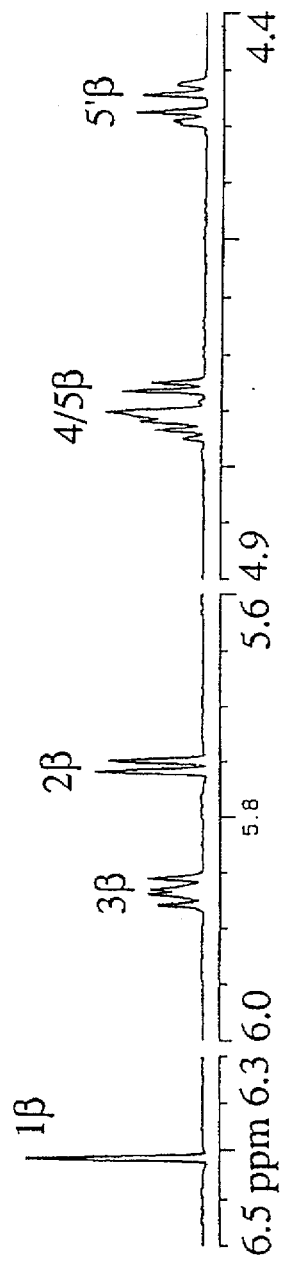
Fig. 1D
Fig. 1E
Fig. 1F

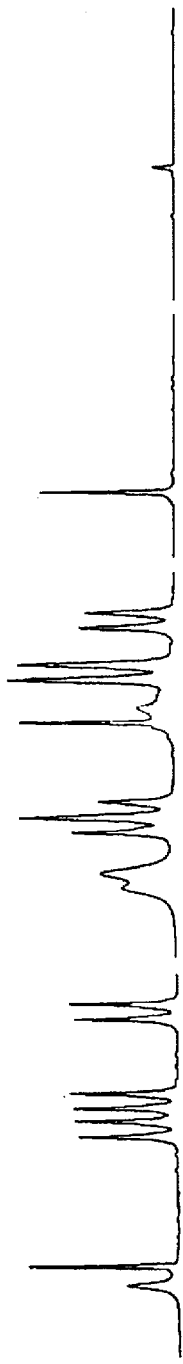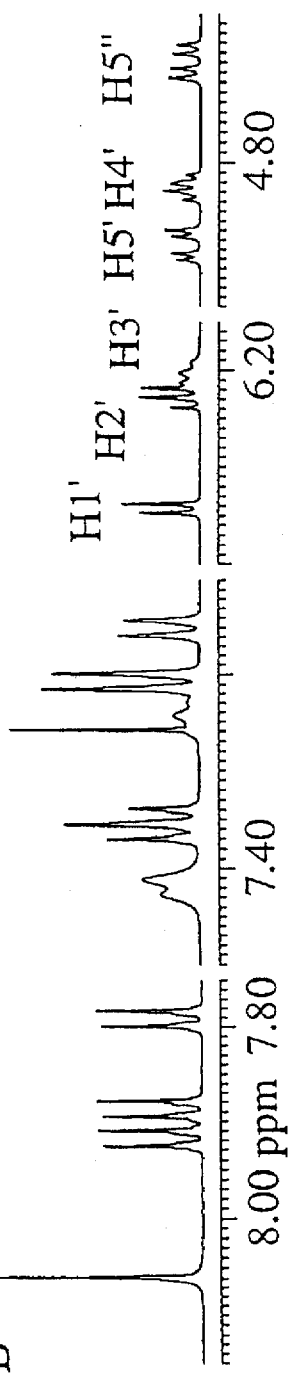
Fig. 3A
Fig. 3B
Fig. 3C

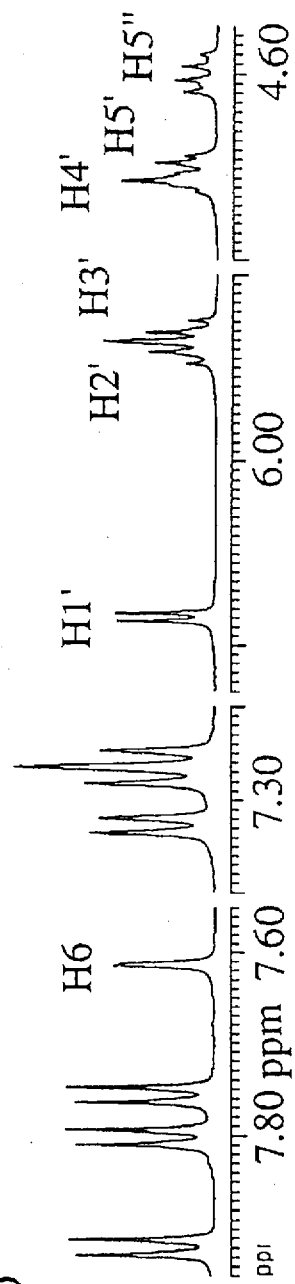
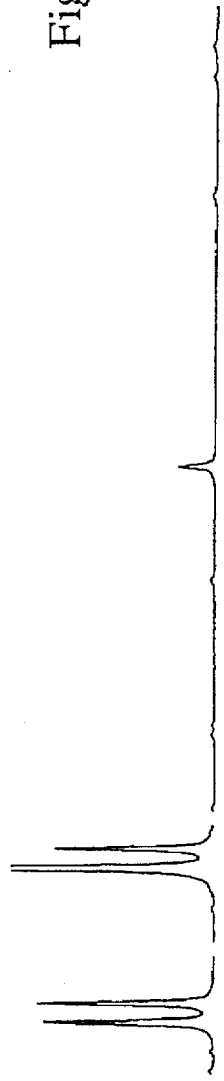
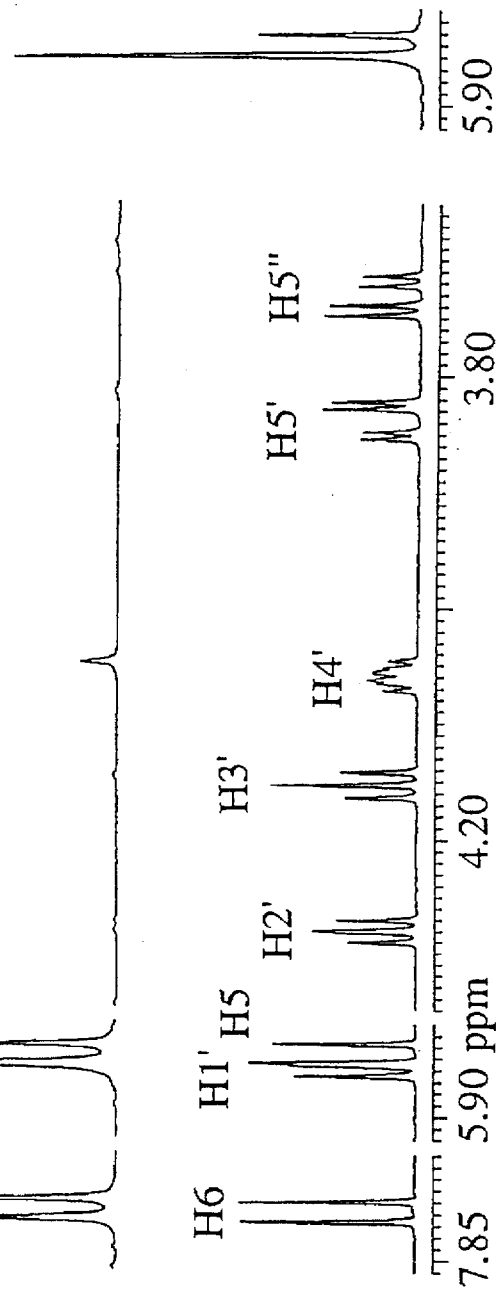
Fig. 3D
Fig. 3E
Fig. 3F
Fig. 3G

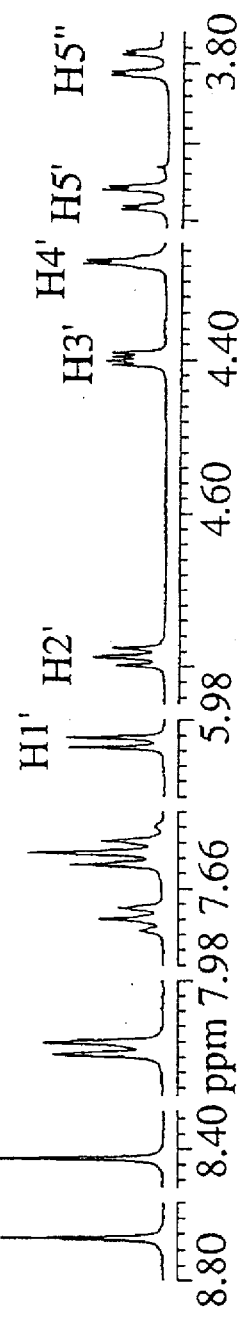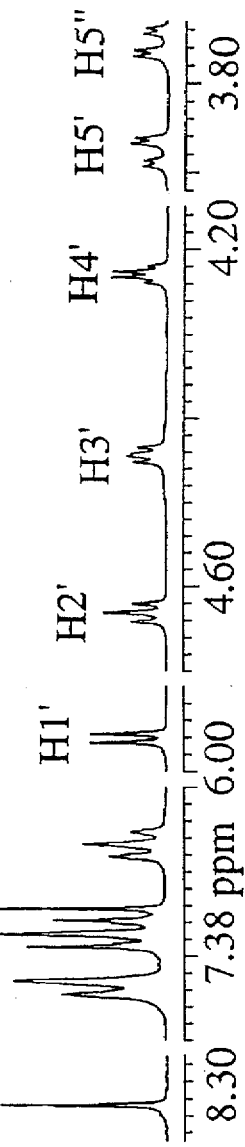
Fig. 4D
Fig. 4E
Fig. 4F

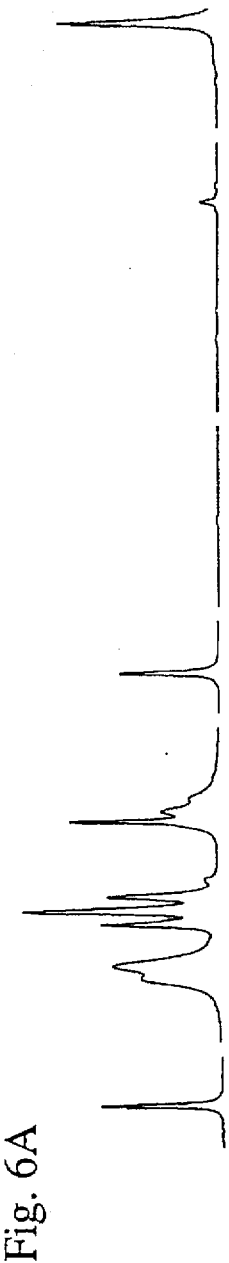
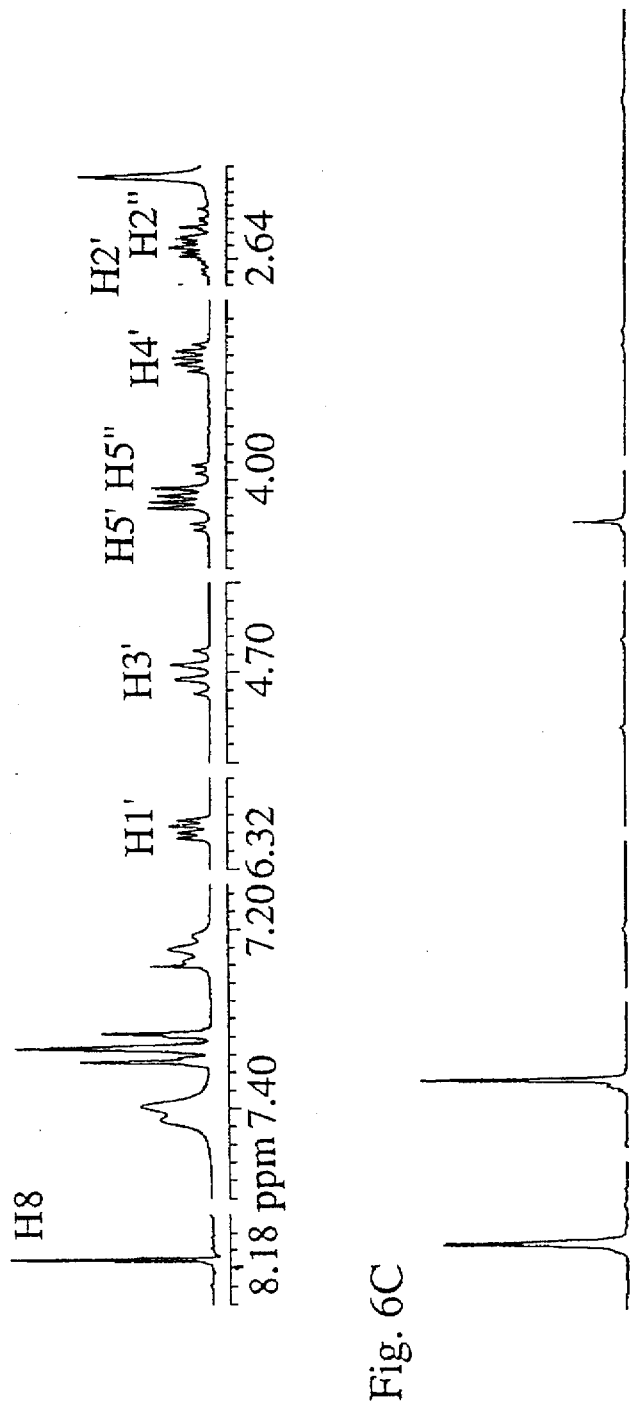
Fig. 6A
Fig. 6B
Fig. 6C

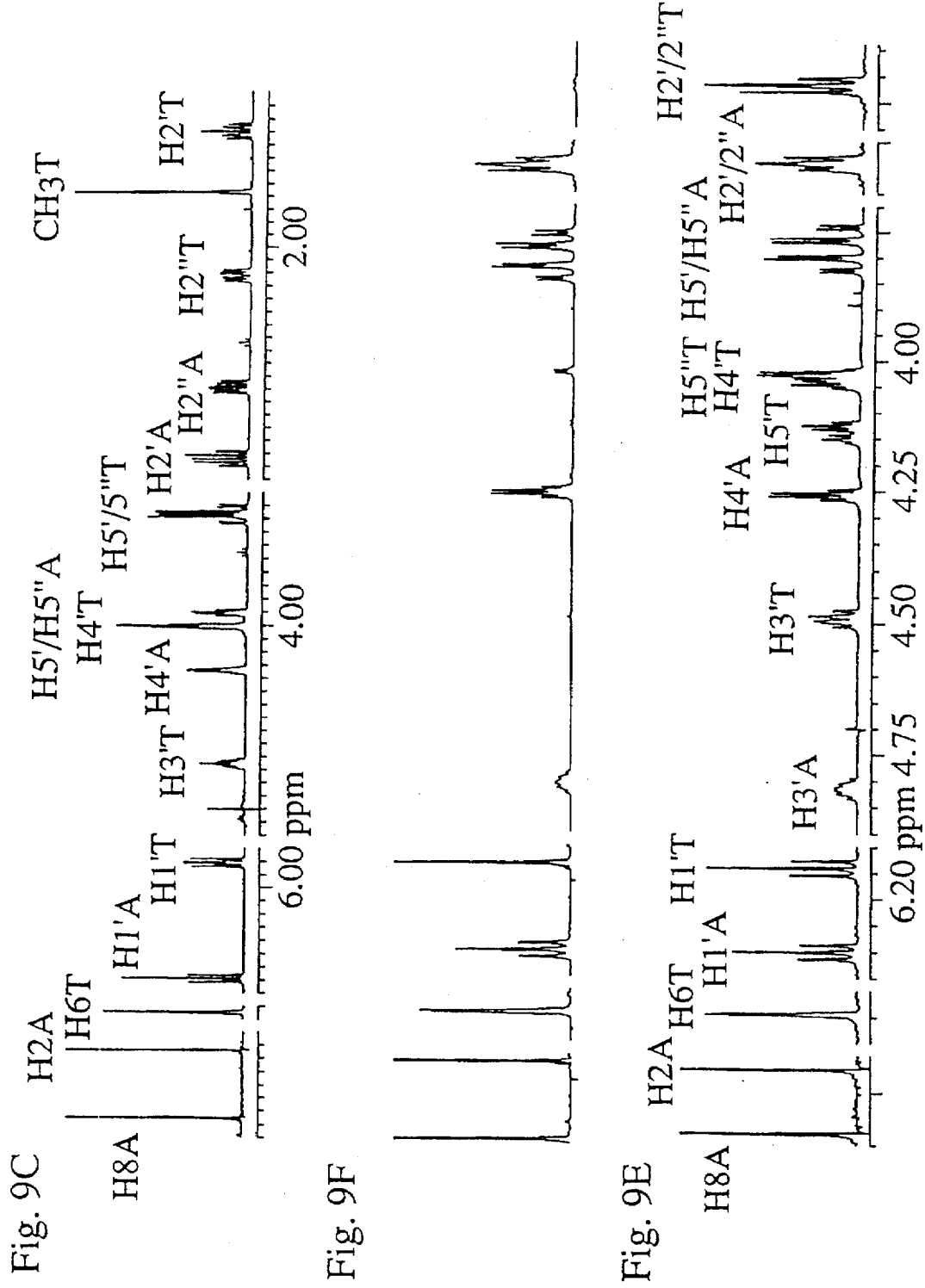

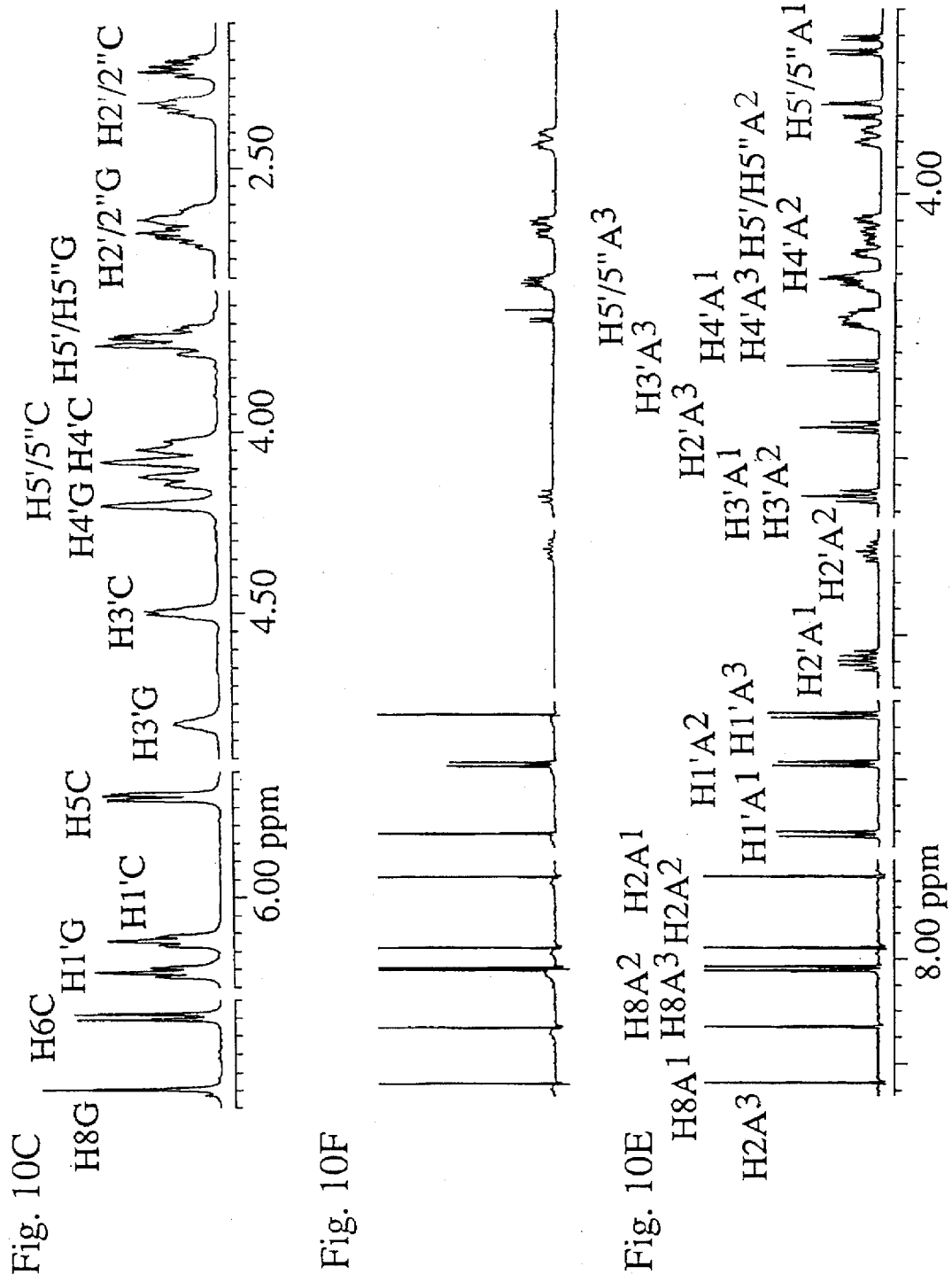

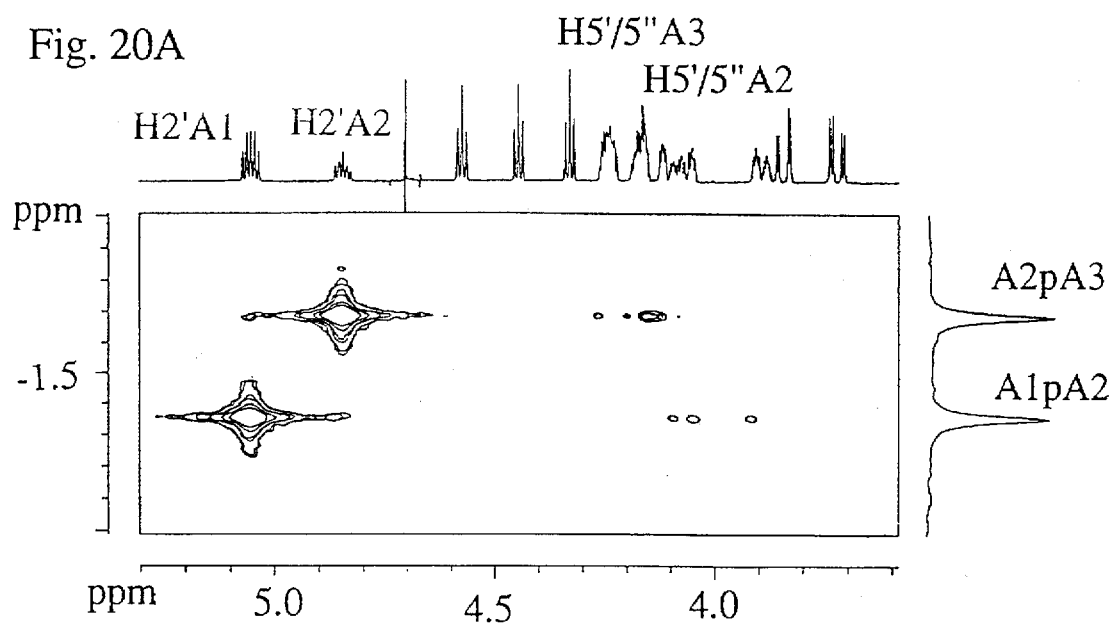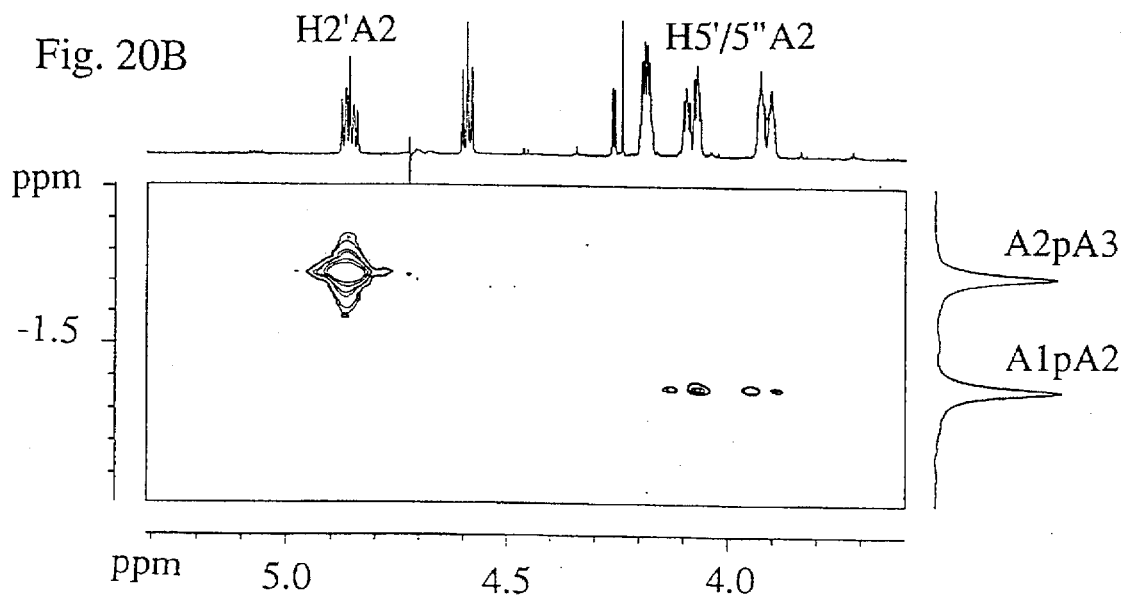

Fig. 21A
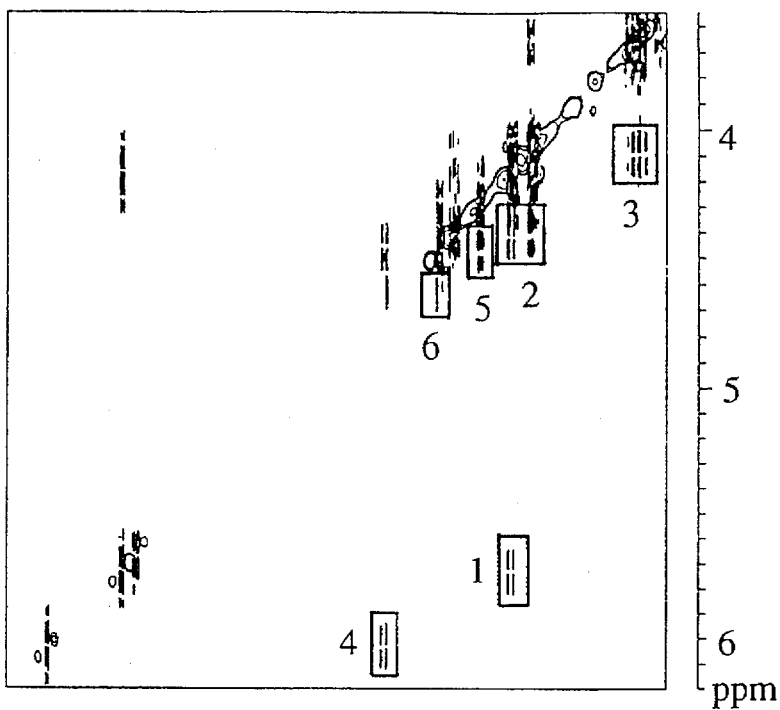
Fig. 21B
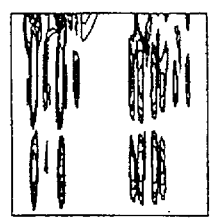
Fig. 21C
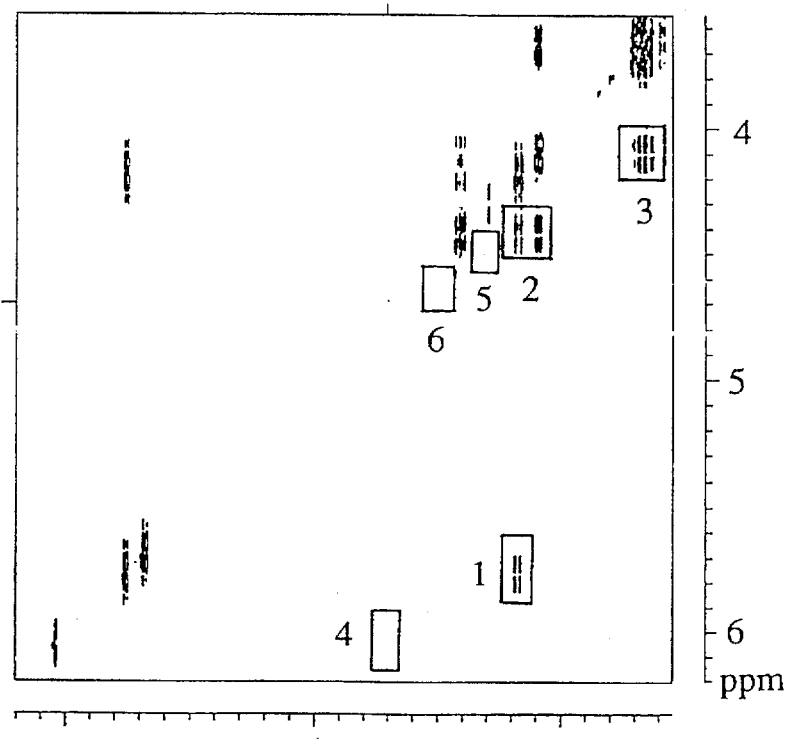
Fig. 21D
Fig. 21E
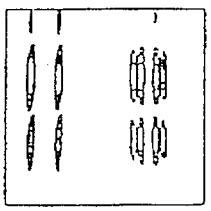
Fig. 21F

Fig. 23A
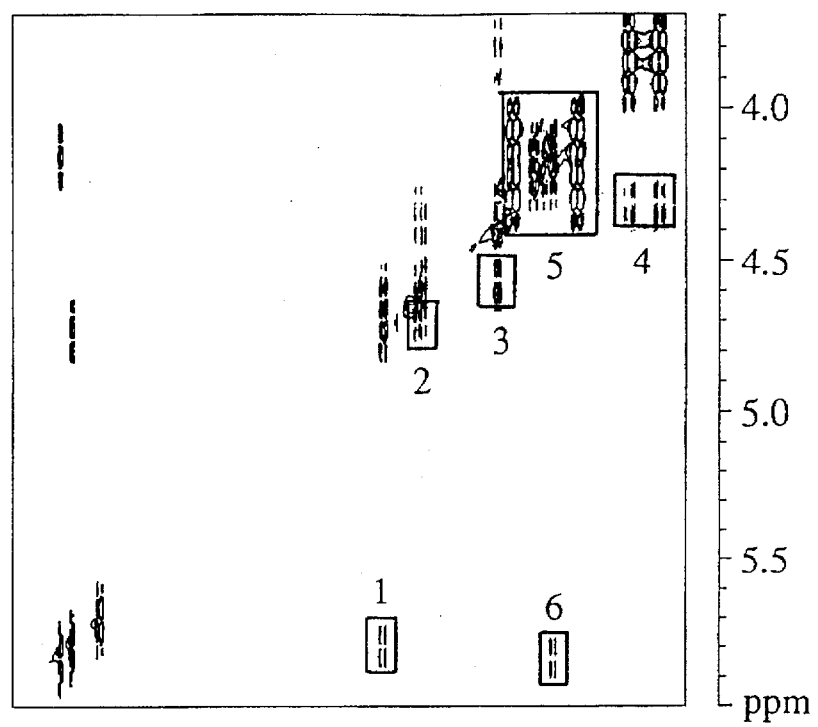
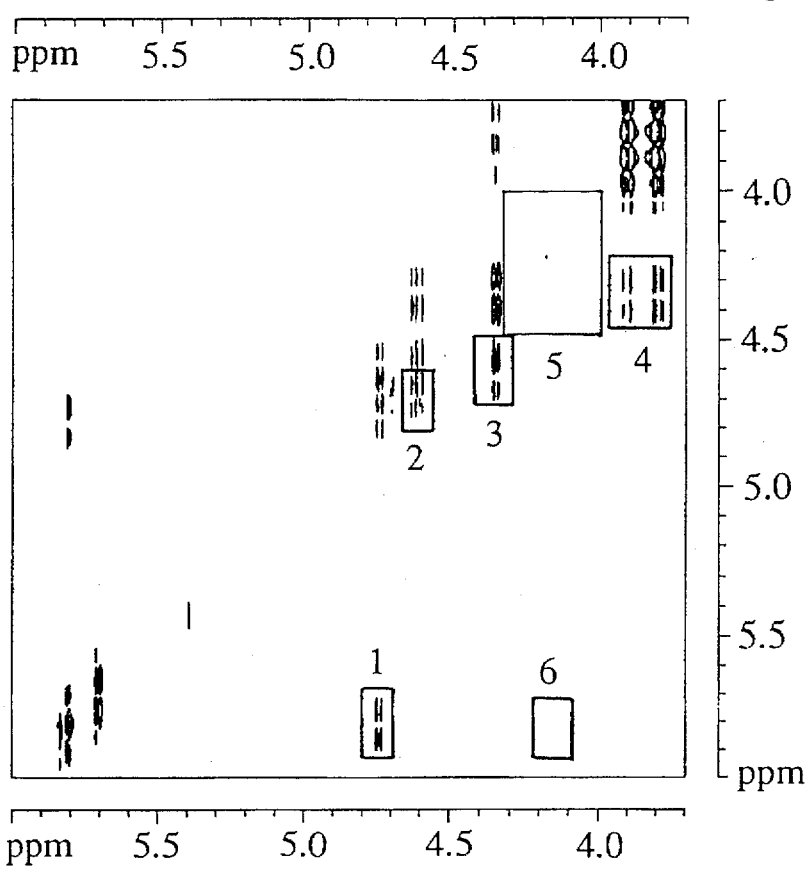
Fig. 23B

Fig. 24A
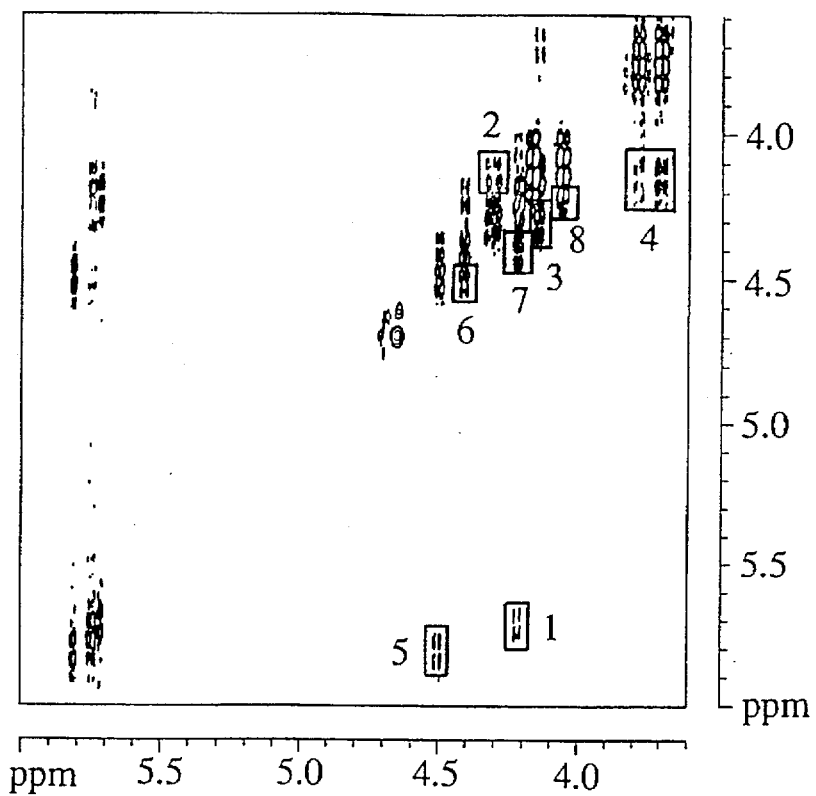
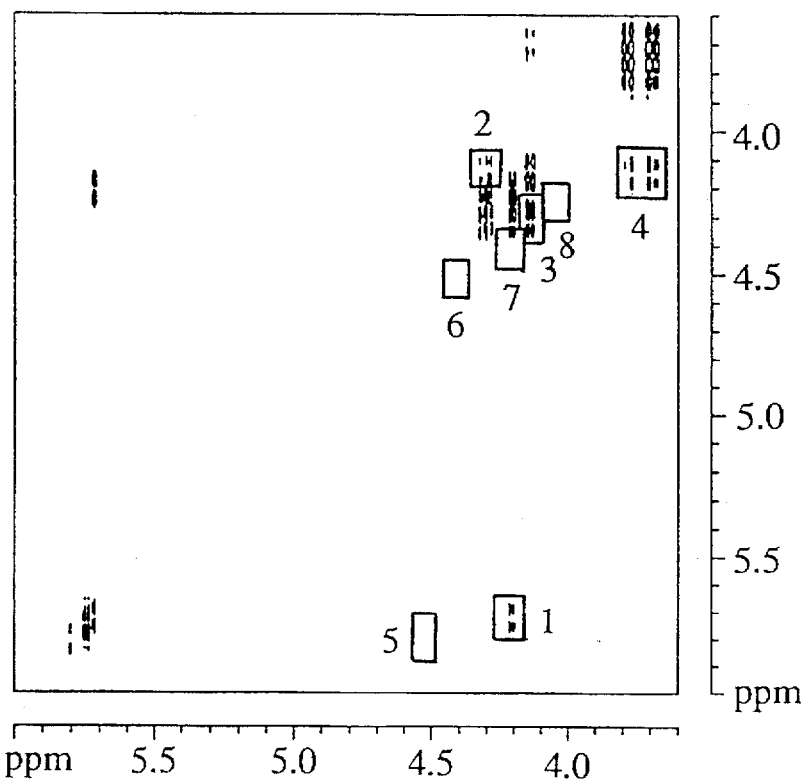
Fig. 24B

Fig. 29A
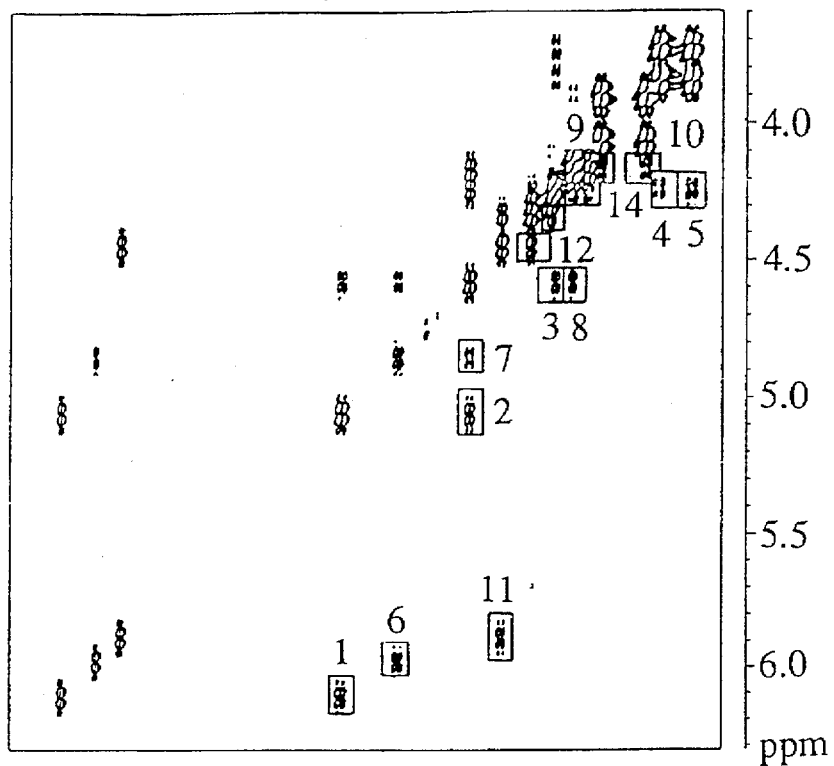
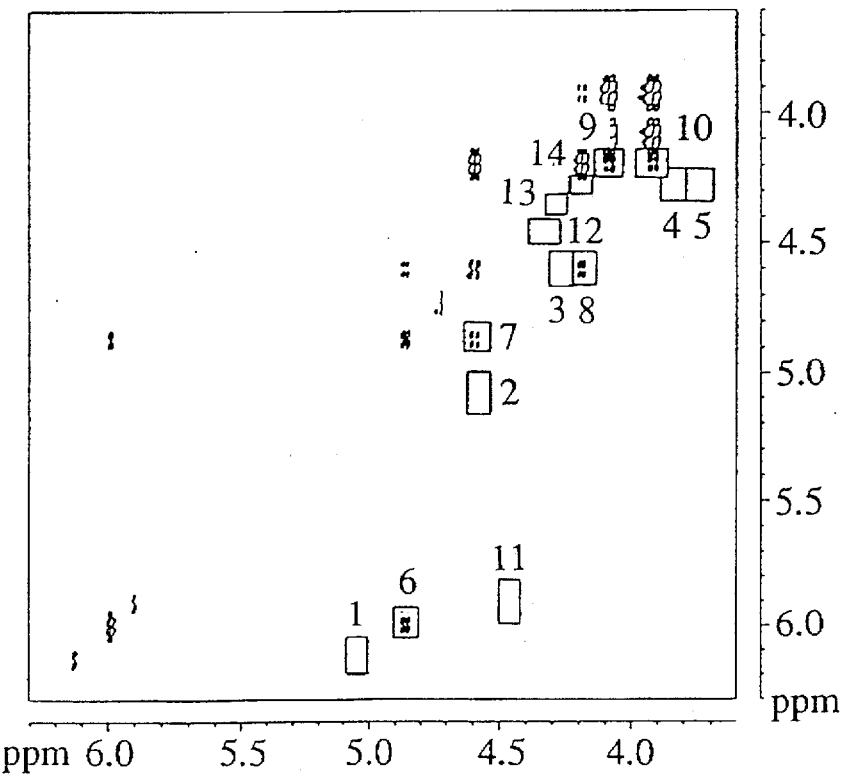
Fig. 29B

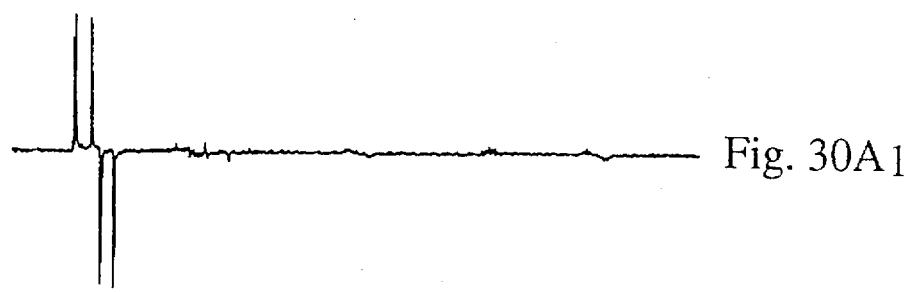
Fig. 30A1
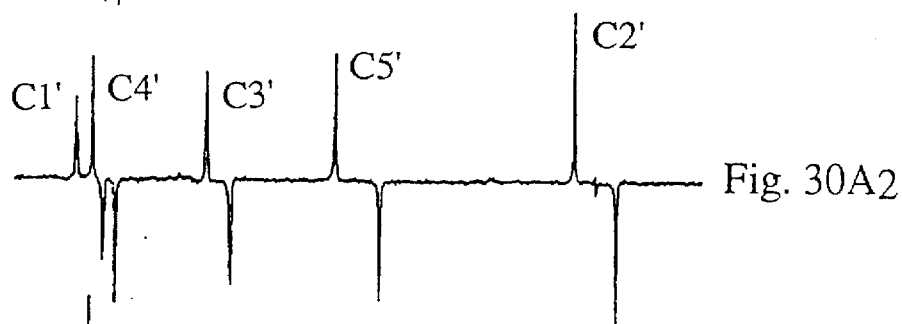
Fig. 30A2
Fig. 30B1
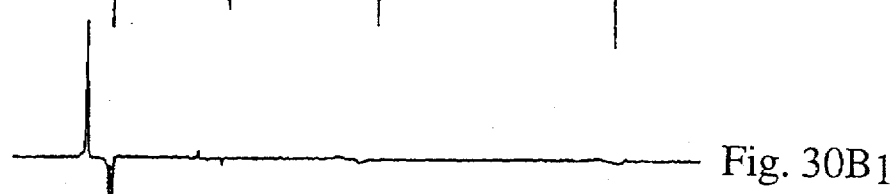
Fig. 30B2
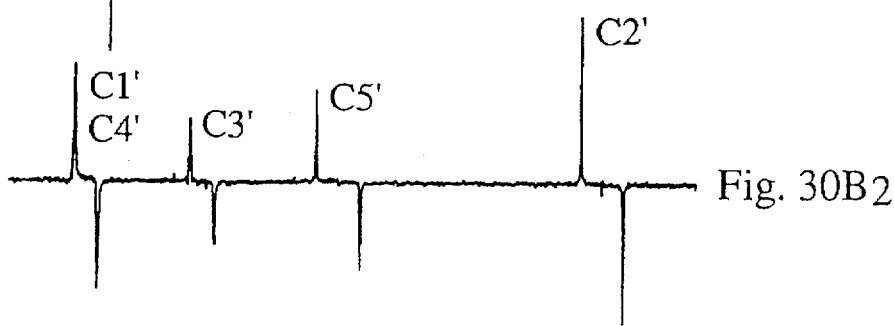
Fig. 30C1
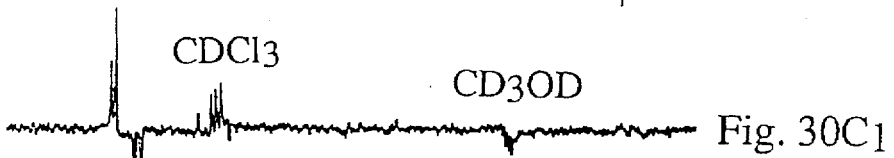
Fig. 30C2
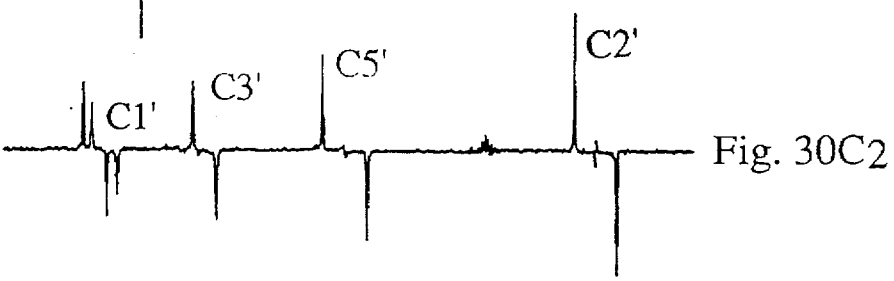
90 85 80 75 70 65 60 55 50 45 40 35 30 ppm

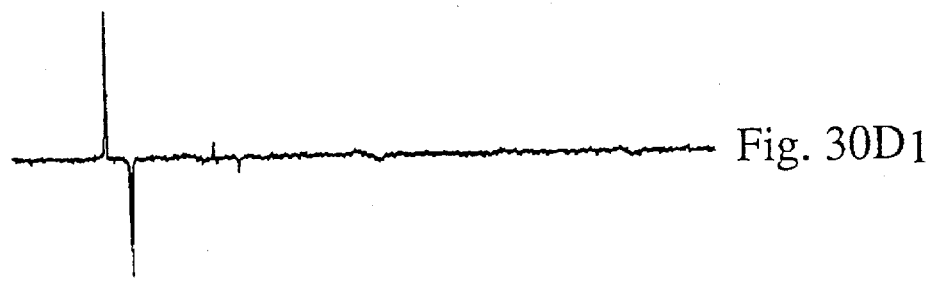
Fig. 30D1
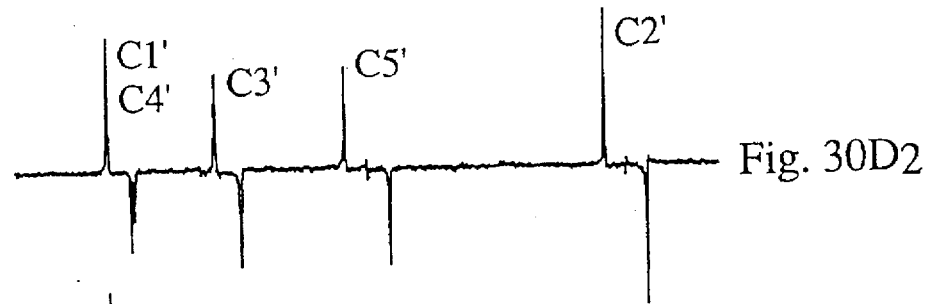
Fig. 30D2
Fig. 31A1
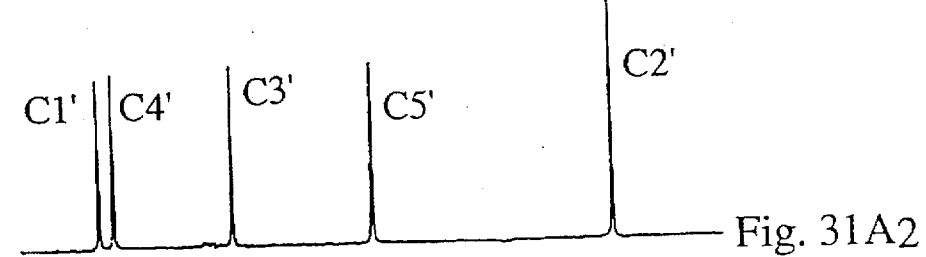
Fig. 31A2
Fig. 31B1
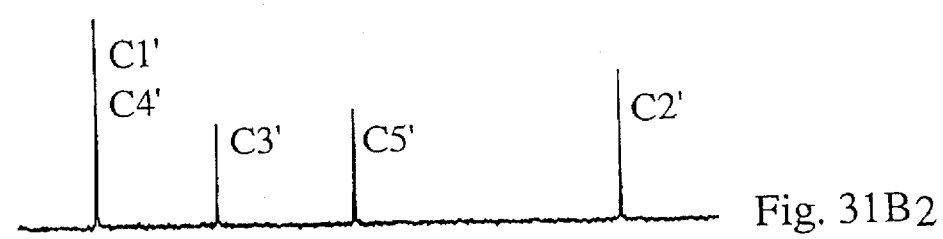
Fig. 31B2

Fig. 31C1
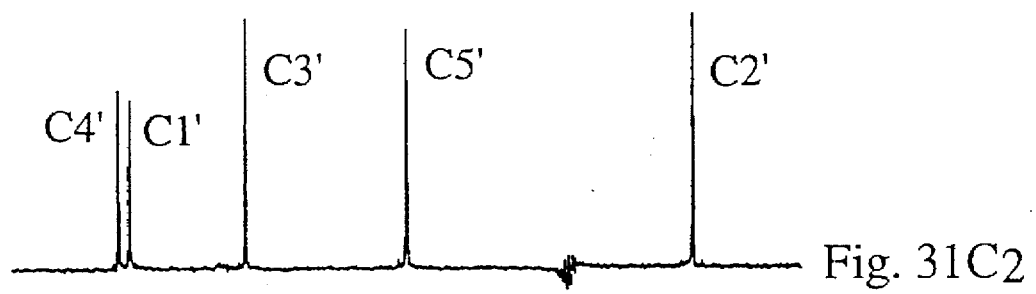
Fig. 31C2
Fig. 31D1
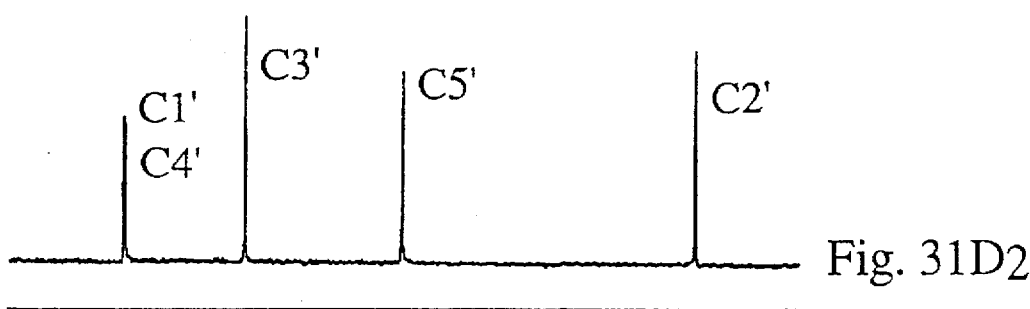
Fig. 31D2

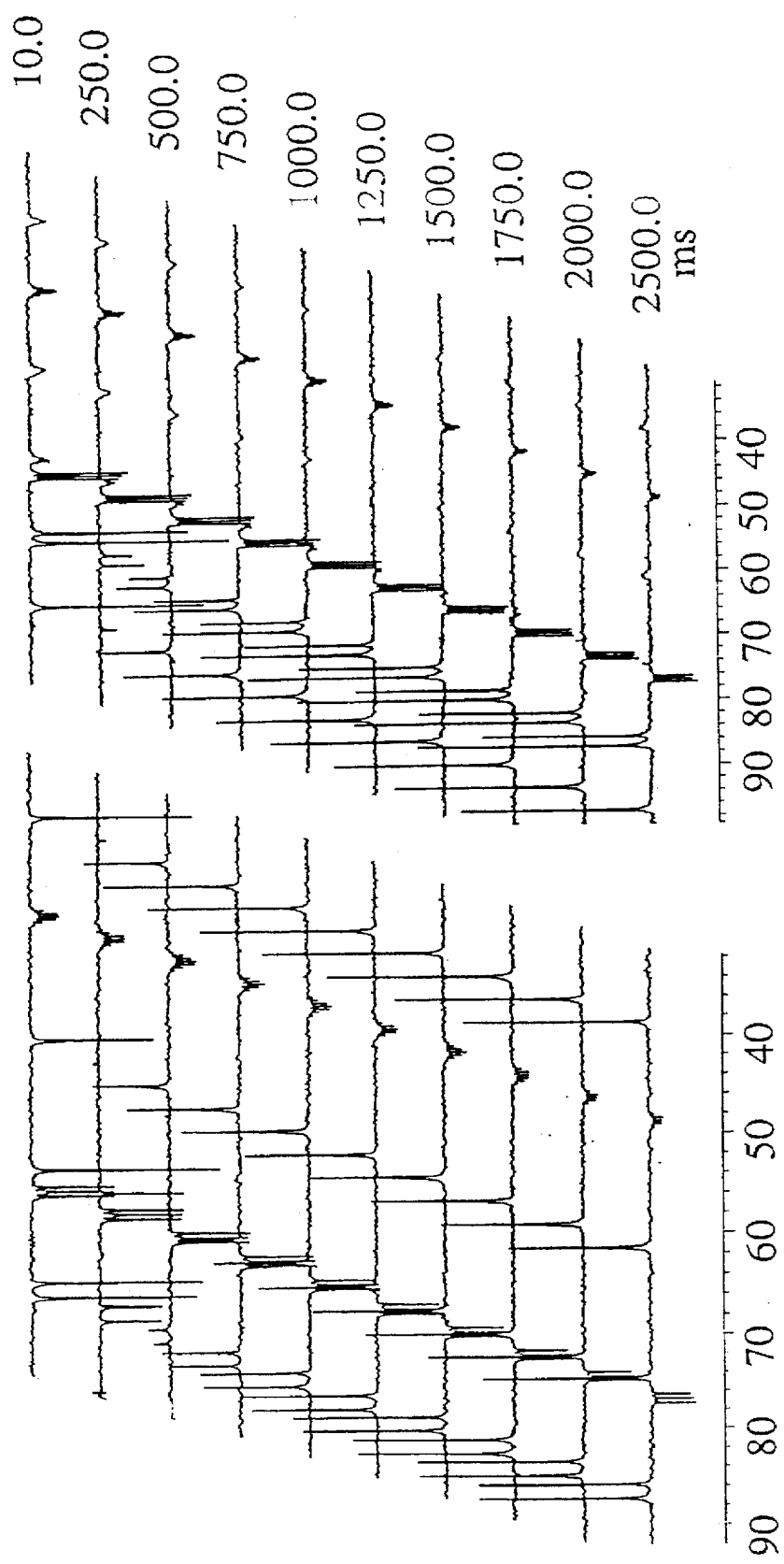

Scheme 2

Scheme 3  Fig. 36

Scheme 4

Route I:
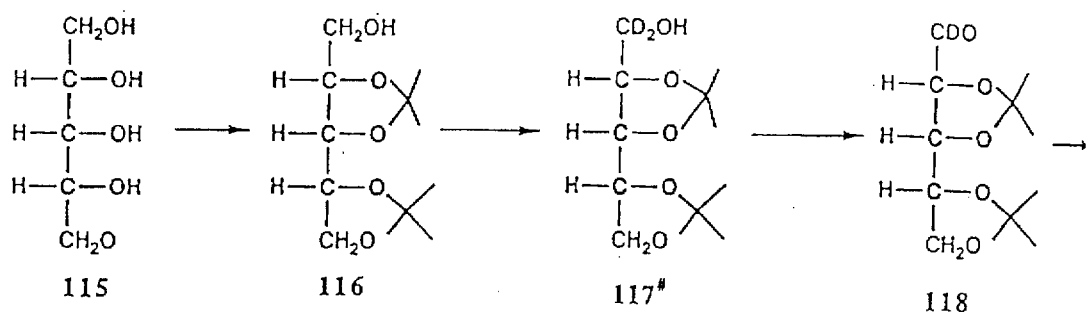
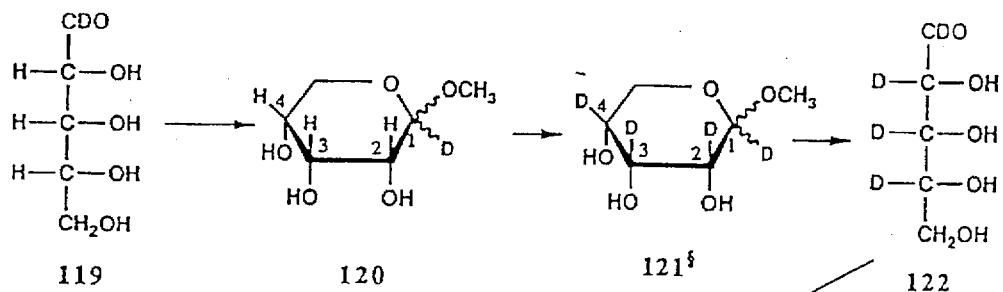
Route II:
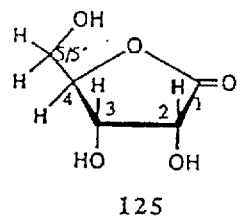
125
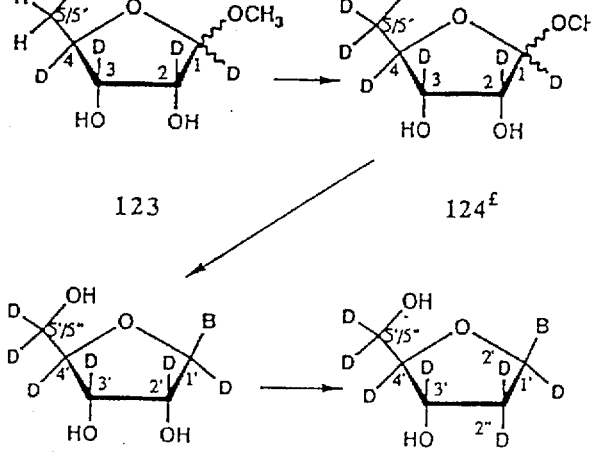
| 126: B = U | 131: B = C^Bz |
| 127: B = C^Bz | 132: B = A^Bz |
| 128: B = A^Bz | 133: B = G_Ac^DPC |
| 129: B = G_Ac^DPC | 134: B = T |
| 130: B = T | |
117#: >97 atom % ²H at C1; 121§: >97 atom % ²H at C1, C2, C3 & C4; 124£ >97 atom % ²H at C1, C2, C3, C4, C5 and C5'.
Scheme 5
Fig. 38

DEUTERATED NUCLEOSIDES

This application is filed under 35 USC 371 as a U.S. National Stage of International (PCT) application PCT/SE92/00450, filed 18 Jun. 1992.

The present invention relates to deuterated nucleosides and nucleotides in a first aspect.

The invention also relates to a process for chemical deuteration of furanosides in a second aspect, and to the preparation of deuterated nucleoside and nucleotide units based on said deuterated furanosides in a third aspect.

The invention additionally relates to a Raney Nickel catalyst useable for achieving sufficiently efficient deuteration.

The invention further relates to the use of said deuterated compounds in NMR applications, especially for the study of RNA and DNA by means of a technique designated as NMR-window technique.

BACKGROUND OF THE INVENTION

The importance of structure and dynamics of DNA and RNA in understanding the biological function has been investigated by a variety of physico-chemical techniques. Amongst these techniques, Nuclear Magnetic Resonance (NMR) spectroscopy has emerged as one of the most powerful tools[1] because it provides conformational information on the implication of variation of local structures and the dynamics under a biological condition. This has been possible due to extensive developments achieved both in hardware (increasing magnetic field, more powerful computers) and spectral editing methodologies (two[1f,2]/three[3a–c] or higher[3d]-dimensional NMR). With increasing magnetic field, the higher sensitivity reduces the amount of an oligomer needed to obtain a good quality spectrum, and increases the dispersion of resonance signals reducing the spectral complexity due to resonance overlap (from second order J couplings to first order). Homonuclear two-dimensional (2D) correlated spectroscopy (COSY) provides a direct proof of the existance of resolved scalar or dipolar couplings ($^3J_{HH}$), and correlate the chemical shifts of coupling partner through the single or multiple coherence transfer of nuclear spins from one transition to another (as in DQFCOSY) or by the migration of coherences in an oscillatory manner through the entire spin (TOCSY) which visualize the structure of the spin system in a most direct and informative manner[2,4]. On the other hand, 2D nuclear Overhauser enhancement (NOESY)[5] result from the transfer of magnetization due to motional processes causing cross relaxation of dipolar-coupled spins which fall off with the sixth power of the distance between two relaxing protons [$<r(t)^{-6}>^{-1/6}$], where r(t)=ensemble of distances due to interconversions of conformations when the NMR measurements were being made)[5b–5e]. Thus NMR has the capabilities of yielding both interproton distances and bond torsion angles which in conjunction of various computational methods (e.g. distance geometry, energy minimization and molecular dynamics) can give the solution structure of oligonucleotides (i.e. conformations of sugars, glycosidic bonds, phosphate backbone, H-bonding, stackings etc).[1d] In these efforts to collect conformational informations, it is ideal that each resonance line and cross-peak due to two interacting protons is clearly separated in homonuclear proton-proton, heteronuclear proton-carbon, proton-phosphorus, carbon-phosphorus, NOESY and ROESY experiments. Although such first order informations are possible to extract from the 2D and 3D NMR experiments of a smaller oligonucleotide, it is simply impossible to collect all of this information in a non-prejudicial manner from a large molecule bigger than 14–16 mer duplex DNA and 7–10 mer single stranded RNA. These problems are associated with spectral overlap which becomes more and more complex due to overcrowding of resonances particularly from the repeating pentose moieties with increasing chain length. It is clear that any technique that simplifies spectral complexities would have a considerable impact in future structural studies of larger DNA or RNA molecules that embody specific biological function. The problem due to severe spectral overlap of protons in absorption assignments and nOe volume measurements could partly be solved by chemical means by selective or complete suppression of absorptions arising from a chosen domain of an oligomer by substituting protons ($^1H$) with deuterons ($^2H$) while extracting necessary information arising from the nondeuterated part of the molecule. By incremental shift of the nondeuterated site ($^1H$-NMR window) in an oligo-DNA or RNA (see FIG. 34), one should be able to put together the total structural information of a much larger oligonucleotide than what is possible today. What is important in this concept is that two adjoining $^1H$-NMR windows in two different oligomers of two consecutive experiments should have at least an overlap of a proton with a specific chemical shift in order to be able to correlate other protons from both windows with respect to the reference point (i.e. same proton resonance in both NMR-windows).

In order to be able to employ the above "windowing" technique, it is essential that the level of deuteration of the "non-window" nucleotides has to be sufficently high in order to suppress stray resonances from the "non-window" part. Accordingly the present invention sets out to provide such compounds.

DISCUSSION OF PRIOR ART

Deuteration of organic compounds is a well established technique, and numerous publications disclose various deuteration methods. One can distinguish between two basic approaches, namely (1) enzymatic incorporation of deuterium, and (2) incorporation of deuterium by chemical (including catalytic) synthesis. Both approaches will be exemplified below.

Kondo et al[25b] disclose enzymatic incorporation of deuterium in dinucleoside monophosphates. They specifically state that the enzymatic approach is advantageous over the chemical one. However, for the purposes of the present invention, their enzymatic incorporation of deuterium is not at all sufficient, which is evidenced from their disclosed NMR spectra (see figures in said publication), wherein clearly residual resonances from the deuterated compound are visible, indicating substantial levels of hydrogen present in the deuterated portions.

Kondo et al[25c] further disclose studies on selectively deuterated trinucleoside diphosphate, wherein deuteration is achieved enzymatically. Also in this publication the NMR spectra (FIGS. 1A to 1F) reveal substantial residual hydrogen resonance peaks, indicating far from adequate deuteration for the purpose of the present application.

Catalytic hydrogen-deuterium exchange has been disclosed by among others Koch et al for alcohols (Canadian Patent 1,081,217), by the same workers for specific labeling of carbohydrates[27b], and by Angyal et al for i.a. methyl furanosides[27h]. In the latter case it is specifically noted (Table II in the publication) that the H-1, i.e. the hydrogen on the C1 in the furanoside was not exchanged for deuterium at all. The other exchange levels as disclosed are not adequate for the purpose of the present invention.

98 Atom % incorporation of deuterium at the C5'-position of thymidine was reported[10]. Dupre et al[9] reported 98 atom % deuteration at C5' of adenosine. The C4'-position of uridine and thymidine was reported to be deuterated to 98 atom %[12]. Deuterium was incorporated to 97 atom % at C3' of adenosine[13].

The above published methods all suffer from the disadvantage that they do not achive the high level of hydrogen-deuterium exchange in all C1'–C5'-positions required for the purpose of using the NMR-window technique.

Clearly, each position of the sugar residue can be selectively labeled, and some of these selectively deuterated nucleosides have indeed found their use in solid-state $^2$H-NMR studies on the internal motions of nucleosides[23] and oligonucleotides[24]. In the temperature dependent line-shape analysis in solid-state $^2$H-NMR spectroscopy, the stereoselectivity of 2' versus 2" labeling[24c] or the level of deuteration do not play a significant role. The use of specifically deuterium labeled nucleotides for the simplification of 1D and 2D $^1$H-NMR spectra in solution studies has not however attracted much attention. An early and so far most extensive use of deuteration in the 1D NMR studies was performed by Danyluk et al. These workers isolated perdeuterated $^2$H-labeled mononucleotides (~90 atom % $^2$H incorporation)[20] in a tedious manner from RNA digest of blue-green algae grown in $^2$H$_2$O. These perdeuterated nucleoside blocks were then used to obtain a wide variety of partially-deuterated dimers and trimers[25] for the purpose of resonance assignments in 1D $^1$H-NMR spectra (200–300 MHz). Synthesis of 4',5',5"-$^2$H$_3$-adenosine[26] was accomplished and coupled to appropriately blocked adenosine 3'-phosphite to give ApA* (pA*=4',5',5"-$^2$H$_3$-pA). This dimer allowed the unequivocal measurement of NOE difference between phosphorus and H-3'[26].

A powerful alternative method of stereospecific deuteration to give polydeuterated sugars employs exchange with deuterium for hydrogen bonded to hydroxyl bearing carbon in sugars (i.e. methylene and methine protons of hydroxyl bearing carbon) using deuterated Raney nickel catalyst in $^2$H$_2$O[27]. Detailed studies revealed structure dependent difference in exchange rates[27e,h], high level of epimerization[27d,g], significantly lower extent of deoxygenation[27h] and difficulties in the reproducibility of the level of deuteration[27h]. Despite these inherent problems in the deuterated Raney nickel-$^2$H$_2$O exchange reaction with the sugars, a number of deuterated nucleosides specifically labeled at 2',3' and 4' positions were prepared for the first time by our taking advantages of this method. Our procedure[28] consisted of deuteration at 2, 3 and 4 positions of methyl β-D-arabinopyranoside by Raney nickel-$^2$H$_2$O exchange reaction[27] followed by reductive elimination of 2-hydroxyl group by tributyltin deuteride[29] to give methyl β-D-2,2',3,4-$^2$H$_4$-2-deoxyribopyranoside which was converted to methyl α/β-D-2,2',3,4-$^2$H$_4$-2-deoxyribofuranoside and glycosylated to give various 2,2',3,4-$^2$H$_4$-nucleosides (97.6 atom % $^2$H incorporation for H3' & H4'; 93.8 atom % $^2$H incorporation for H2 and H2'). Recently methyl β-D-erythrofuranoside was treated with deuterated Raney Ni to afford after purification methyl β-D-2,3,4(S)-$^2$H$_3$-erythrofuranoside (~75 atom % $^2$H incorporation at C2 and C4(S) positions and 100 atom % $^2$H incorporation at C3)[27i]. This sugar was converted to D-3,4,5(S)-$^2$H$_3$-ribose from which the four ribonucleoside were prepared. These nucleosides were subsequently reduced to the corresponding 3',4', 5'(S)-$^2$H$_3$-2'-deoxynucleosides[27j].

During our 1D and/or 2D NMR studies on conformation of trimeric, tetrameric, pentameric, heptameric, nonameric and decameric branched RNAs[30a] and DNA duplexes[30b] we realized, that, though the assignment of given protons could be facilitated by low level selective deuteration at chosen sites of short oligomers, the substantial simplification of the crowded sugar domain could not be achieved in this manner. This promted us to reconsider the $^1$H-NMR window concept (FIG. 34) which in its most simple form has appeared in Danyluk and coworkers' publications[25] with low, unsatisfactory level of deuteration which suffice for the purpose of assignment of resonances only. But in the present concept of $^1$H-NMR window for the substantial simplification of the crowded sugar domain, we have set out to achieve a highest possible level of deuteration of nucleoside moieties in order to suppress stray proton resonances from these moieties as much as possible (creation of truely $^1$H-NMR invisible domain due to deuteration, see FIG. 34) to the $^1$H-NMR window for elucidation of conformations of DNA and RNA in conjunction with modern multidimensional NMR techniques.

We realized that the goal for high level of deuteriation of as many carbons as possible can be achieved only by synthetic chemistry since the published enzymatic method is known to give low unacceptable level of deuterium incorporation from deuterated blue green algae[20,53].

THE TECHNICAL PROBLEM

Thus, the technical problem that the invention sets out to solve, is to provide deuterated building blocks for the synthesis of specifically deuterated poly-/oligo-RNA and DNA, wherein the non-deuterated portion (NMR window) only is visible in NMR experiments, such as COSY, NOESY, ROESY, HOHAHA etc.

This problem is solved by incorporating high level of deuterium in the sugar moiety and subsequently coupling this, appropriately protected, furanoside compound with either of uracil, cytosine, adenine, guanine, thymine or derivatives of the latter bases.

Subsequent polymerization, i.e. synthesis of DNA/RNA-strands, of these nucleosidyl residues with each other and with at least one non-deuterated residue, provides an RNA/DNA oligomer having a said desired "window" in NMR experiments.

The deuteration level in the deuterated residues must be sufficiently high for the signals from the deuterated building blocks (i.e. nucleotidyl residues) not to disturb the NMR-spectrum from the non-deuterated part.

The present invention provides in a first aspect such deuterated nucleosides and nucleotides which are defined in claims 1–6.

The problem of achieving such sufficiently high level of deuteration in said building blocks is solved by the method of preparing deuterated methyl α/β-ribofuranoside, according to claim 8.

BRIEF DESCRIPTION OF THE DRAWINGS

The invention will now be described in detail with reference to the drawings, in which FIGS. 1(A) through 1(F): 500 MHz $^1$H-NMR spectra of deuterated D-ribofuranoses (>97 atom % $^2$H at C2, C3, C5/5'; ~85 atom % $^2$H at C4; ~20 atom % $^2$H at C1) and their natural-abundance counterparts (99.985 atom % $^1$H);. (A) shows the reaction mixture of deuterated Raney-Ni exchanged methyl-(α/β)-D-ribofuranoside (2) & (B) shows natural-abundance methyl-(α/β: ~3/10)-D-ribofuranoside (1). (C) shows 1-O-methyl-2,3,5-tri-O-(4-toluoyl)-(α/β: ~1/10)-

Figure 1A:
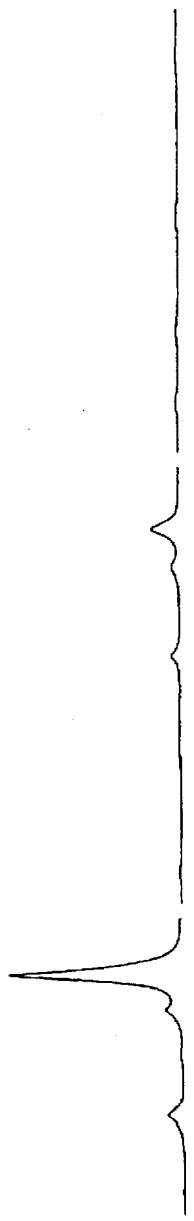

D-ribofuranoside (4) & (D) shows its natural-abundance counterpart. (E) shows 1-O-acetyl-2,3,5-tri-O-(4-toluoyl)-β-D-ribofuranoside (6) and (F) shows its natural-abundance counterpart. Note that only sugar protons are shown in the above subspectra.

FIGS. 2(A) through 2(F): 500 MHz $^1$H-NMR spectra of deuterated-β-D-nucleosides (>97 atom % $^2$H at C2', C3', C5'/5"; ~85 atom % $^2$H at C4' (C4'#); ~20 atom % $^2$H at C1' (C1'#)) and their natural-abundance counterparts (99.985 atom % $^1$H);. (A) shows 2',3',5'-O-tri-(4-toluoyl)-1'#,2',3', 4'#,5',5"-$^2$H$_6$-uridine (7); (B) shows natural-abundance counterpart; (C) shows 2',3',5'-O-tri-(4-toluoyl)-1'#,2',3',4'#, 5',5"-$^2$H$_6$-N$^4$-benzoylcytidine (8); (D) shows natural-abundance counterpart; (E) shows 2',3',5'-O-tri-(4-toluoyl)-1'#,2',3',4'#,5',5"-$^2$H$_6$-N$^6$-benzoyladenosine (9); (E) shows natural-abundance counterpart.

FIGS. 3(A) through 3(F): 500 MHz $^1$H-NMR spectra of deuterated-β-D-nucleosides (>97 atom % $^2$H at C2', C3', C5'/5"; ~85 atom % $^2$H at C4' (C4'#); ~20 atom % $^2$H at C1' (C1'#)) and their natural-abundance counterparts (99.985 atom % $^1$H) (A) shows 2',3',5'-O-tri-(4-toluoyl)-1'#,2',3',4'#, 5',5"-$^2$H$_6$-N$^2$-acetyl-O$^6$-diphenylcarbamoylguanosine (10); (B) shows natural-abundance counterpart; (C) shows 1-(2', 3',5'-O-tri-(4-toluoyl)-1'#,2',3',4'#,5',5"-$^2$H$_6$-β-D-ribofuranosyl)-thymine (11); (D) shows natural-abundance counterpart; (E) shows 1'#,2',3',4'#,5',5"-$^2$H$_6$-uridine (12); (F) shows natural-abundance counterpart; (G) shows the full height anomeric region of 1'#,2',3',4'#,5',5"-$^2$H$_6$-uridine (12) from subspectrum (E).

FIGS. 4(A) through 4(F): 500 MHz $^1$H-NMR spectra of deuterated-β-D-nucleosides (>97 atom % $^2$H at C2', C3', C5'/5"; ~85 atom % $^2$H at C4' (C4'#); ~20 atom % $^2$H at C1' (C1'#)) and their natural-abundance counterparts (99.985 atom % $^1$H). (A) shows 1'#,2',3',4'#,5',5"-$^2$H$_6$-N$^4$-benzoylcytidine (13); (B) shows natural-abundance counterpart; (C) shows 1'#,2',3',4'#,5',5"-$^2$H$_6$-N$^6$-benzoyladenosine (14); (D) shows natural-abundance counterpart; (E) shows 1'#,2',3',4'#,5',5"-$^2$H$_6$-N$^2$-acetyl-O$^6$-diphenylcarbamoylguanosine (15); (F) shows natural-abundance counterpart.

FIGS. 5(A) through 5(F): 500 MHz $^1$H-NMR spectra of deuterated-β-D-nucleosides (>97 atom % $^2$H at C2', C3', C5'/5"; ~85 atom % $^2$H at C4' (C4'#); ~20 atom % $^2$H at C1' (C1'#)) and their natural-abundance counterparts (99.985 atom % $^1$H). (A) shows 1-(1'#,2',3',4'#,5',5"-$^2$H$_6$-β-D-ribofuranosyl)-thymine (16); (B) shows natural-abundance counterpart; (C) shows 3',5'-O-(1,1,3,3-tetraisopropyldisiloxane-1,3-diyl)-1'#,2',2",3',4'#,5',5"-$^2$H$_7$-2'-deoxy-N$^4$-benzoylcytidine (37); (D) shows natural-abundance counterpart; (E) shows 3',5'-O-(1,1,3,3-tetraisopropyldisiloxane-1,3-diyl)-1'#,2',2",3',4'#,5',5"-$^2$H$_7$-2'-deoxy-N$^6$-benzoyladenosine (38); (F) shows natural-abundance counterpart.

FIGS. 6(A) through 6(F): 500 MHz $^1$H-NMR spectra of deuterated-β-D-nucleosides (>97 atom % $^2$H at C2', C3', C5'/5"; ~85 atom % $^2$H at C4' (C4'#); ~20 atom % $^2$H at C1' (C1'#)) and their natural-abundance counterparts (99.985 atom % $^1$H). (A) shows 3',5'-O-(1,1,3,3-tetraisopropyldisiloxane-1,3-diyl)-1'#,2',2",3',4'#,5',5"-$^2$H$_7$-2'-deoxy-N$^2$-acetyl-O$^6$-diphenylcarbamoylguanosine (39); (B) shows natural-abundance counterpart; (C) 3',5'-O-(1,1, 3,3-tetraisopropyldisiloxane-1,3-diyl)-1'#,2',2",3',4'#,5',5"-$^2$H$_7$-thymidine (40); (D) shows natural-abundance counterpart; (E) shows 1'#,2',2",3',4'#,5',5"-$^2$H$_7$-2'-deoxy-N$^4$-benzoylcytidine (41); (F) shows natural-abundance counterpart.

FIGS. 7(A) through 7(F): 500 MHz $^1$H-NMR spectra of deuterated-β-D-nucleosides (>97 atom % $^2$H at C2', C3', C5'/5"; ~85 atom % $^2$H at C4' (C4'#); ~20 atom % $^2$H at C1' (C1'#)) and their natural-abundance counterparts (99.985 atom % $^1$H). (A) shows 1'#,2',2",3',4'#,5',5"-$^2$H$_7$-2'-deoxy-N$^6$-benzoyladenosine (42); (B) shows natural-abundance counterpart; (C) shows 1'#,2',2",3',4'#,5',5"-$^2$H$_7$-2'-deoxy-N$^2$-acetyl-O$^6$-diphenylcarbamoylguanosine (43); (D) shows natural-abundance counterpart; (E) shows 1'#,2',2",3',4'#,5', 5"-$^2$H$_7$-thymidine (44); (F) shows natural-abundance counterpart.

FIGS. 8(A) through 8(F): $^1$H-NMR spectra of natural and partially deuterated diribonucleoside-(3'→5')-monophosphate in D$_2$O at 298K. (A): natural UpA, (B): UpA* where the 1'#,2',3',4'# and 5'/5" protons of the adenosine (pA*) residue are exchanged with $^2$H. (C): natural ApU, (D): ApU* where the 1'#,2',3',4'# and 5'/5" protons of the uridine (pU*) residue are exchanged with $^2$H. (E): natural CpG, (F): CpG* where the 1'#,2',3',4'# and 5'/5" protons of the guanosine (pG*) residue are exchanged with $^2$H. The H1'# appears as a singlet while the H4'# appears as a doublet due its coupling to the phosphorus of the 3"5' phosphate linkage.

FIGS. 9(A) through 9(F): $^1$H-NMR spectra of natural and partially deuterated diribonucleoside-(3'→5')-monophosphate and di(2'-deoxyribonucleoside)-(3'→5')-monophosphate in D$_2$O at 298K. (A): natural GpC, (B): GpC* where the 1'#,2',3',4'# and 5'/5" protons of the adenosine (pC*) residue are exchanged with $^2$H. (C): natural d(TpA), (D): d(TpA*) where the 1'#,2',3',4'# and 5'/5" protons of the adenosine (pA*) residue are exchanged with $^2$H. (E): natural d(ApT), (F): d(ApT*) where the 1'#,2',3',4'# and 5'/5" protons of the thymidine (pT*) residue are exchanged with $^2$H. The H1'# appears as a singlet while the H4'# appears as a doublet due its coupling to the phosphorus of the 3'→5' phosphate linkage.

FIGS. 10(A) through 10(F): $^1$H-NMR spectra of natural and partially deuterated di(2'-deoxyribonucleoside)-(3'→5')-monophosphate and 2,5A core in D$_2$O at 298K. (A): natural d(CpG), (B): d(CpG*) where the 1'#,2',3',4'# and 5'/5" protons of the guanosine (pG*) residue are exchanged with $^2$H. (C): natural d(GpC), (D): d(GpC*) where the 1'#,2',3',4'# and 5'/5" protons of the cytidine (pC*) residue are exchanged. (E) A$^1$(2'→5')A$^2$(2'→5')A$^3$, (F): A$^1$*(2'→5')A$^2$(2'→5')A$^3$* where the 1'#,2',3',4'# and 5'/5" protons of the 5'-terminal A$^1$ and 3'-terminal A$^3$ residues are exchanged with $^2$H. The H1'# of A$^1$* and A$^3$* residues appear as singlet. The H4'# of A$^1$* appears as a singlet while the H4'# of A$^3$* appears as a doublet due to its coupling to the phosphorus of the A$^2$(3'→5')A3 phosphate linkage.

Figure 11A:
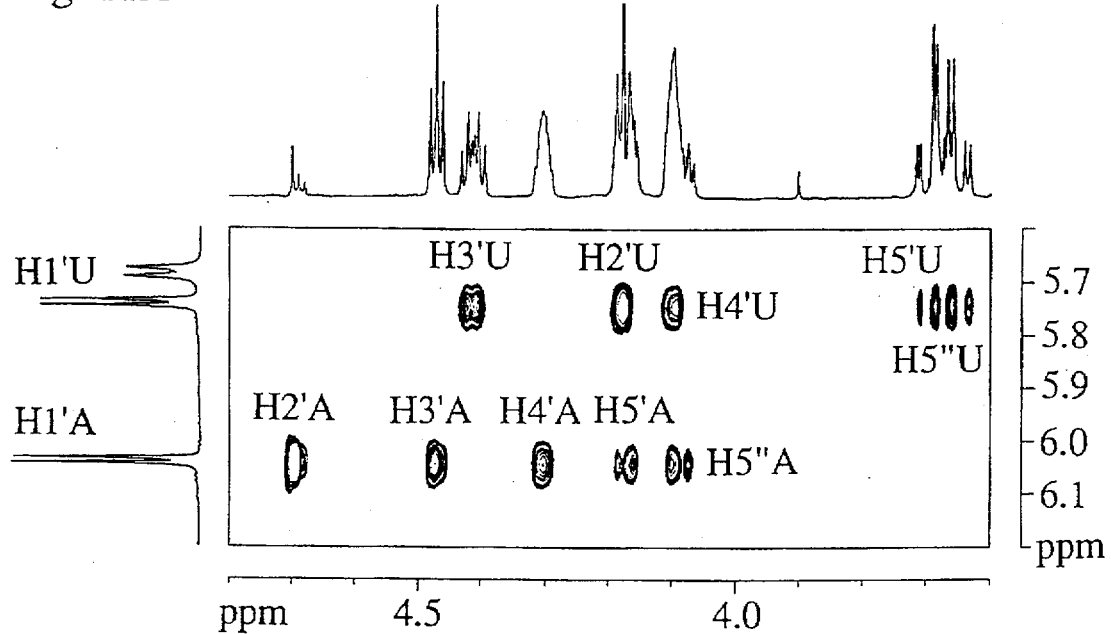
Figure 11B:
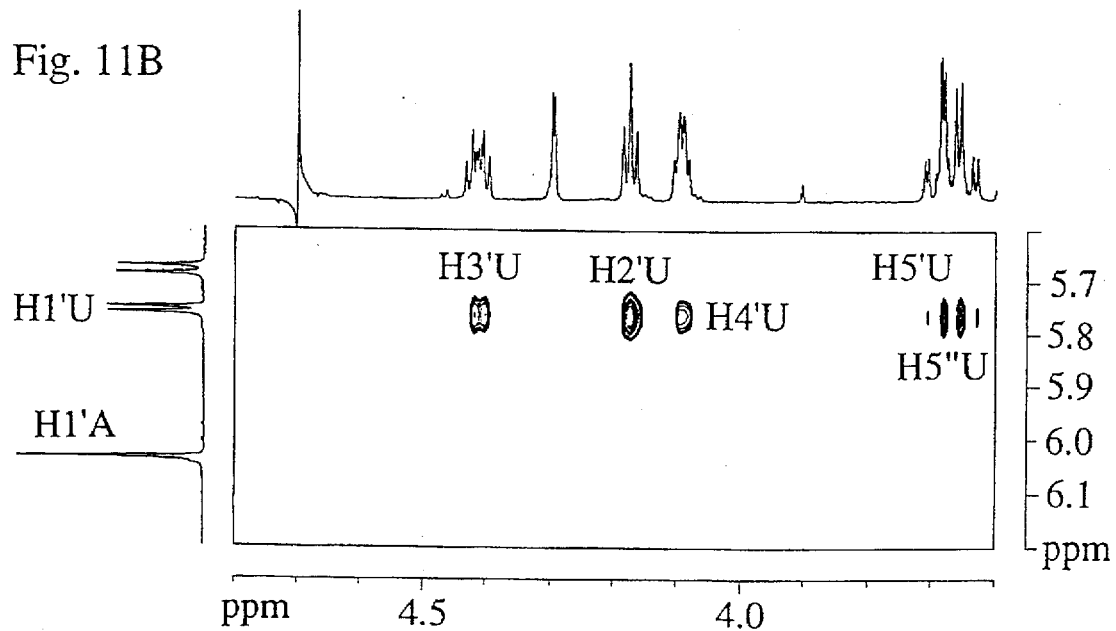

FIGS. 11(A) through 11(B): 2D homonuclear Hartmann Hahn (HOHAHA) spectra of the natural and partially deuterated Uridylyl-(3'→5')-adenosine (UpA) in D$_2$O at 298K. Panel A represents the 2D spectrum for the non-deuterated UpA. Panel B represents the 2D spectrum of the partially deuterated UpA* where the 1'#,2',3',4'# and 5'/5" protons of the adenosine (pA*) residue are exchanged. In the 1D spectrum, the H1' appears as a singlet at 6.05 ppm while the H4' appears as a doublet at 4.29 ppm due to its coupling to the phosphorus of the 3"5' phosphate linkage. In the 2D spectrum, the J-network for the 3'-terminal residue (pA*) has vanished.

Figure 12A:
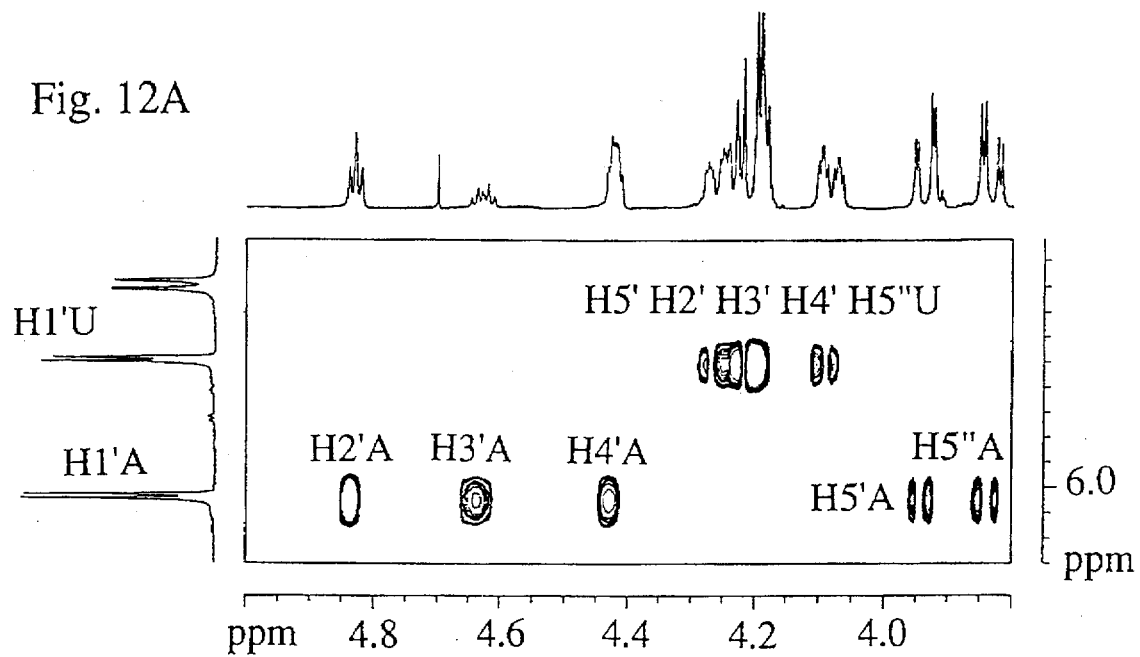
Figure 12B:
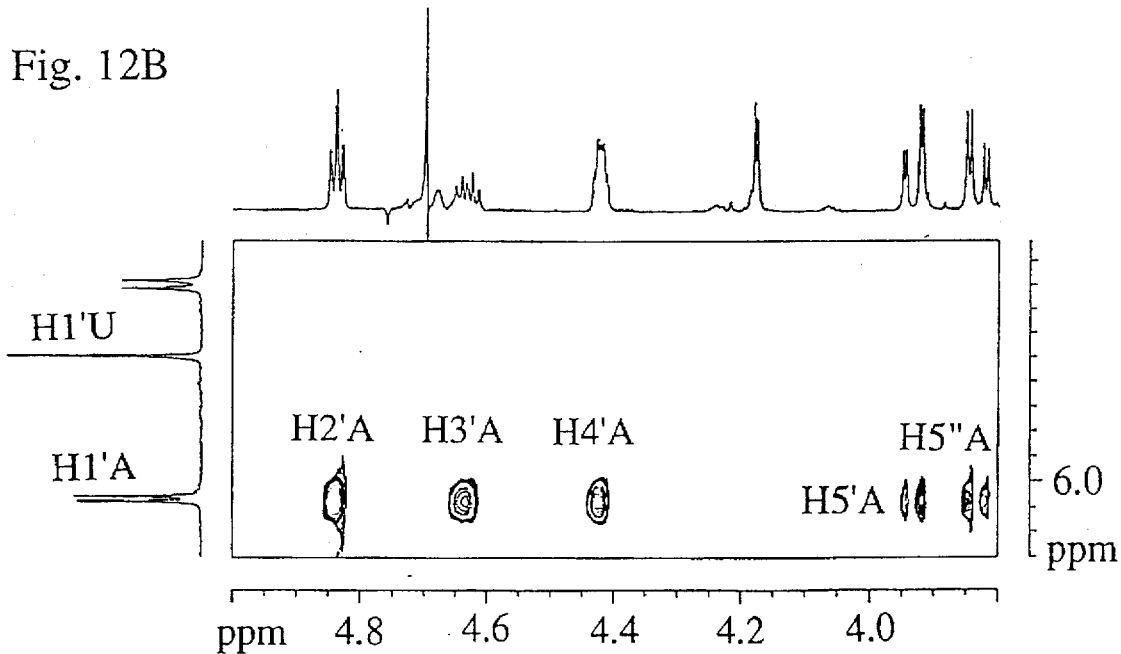

FIGS. 12(A) through 12(B): HOHAHA spectra of the natural and partially deuterated adenylyl-(3'→5')-uridine (ApU) in D$_2$O at 298K. Panel A represents the 2D spectrum for the non-deuterated ApU. Panel B represents the 2D spectrum of the partially deuterated ApU* where the 1'#,2', 3',4'# and 5'/5" protons of the uridine (pU*) residue are exchanged. In the 1D spectrum, the H1' appears as a singlet at 5.75 ppm while the H4' appears as a doublet at 4.15 ppm due to its coupling to the phosphorus of the 3"5' phosphate linkage. In the 2D spectrum, the J-network for the 3'-terminal residue (pU*) has vanished.

Figure 13A:
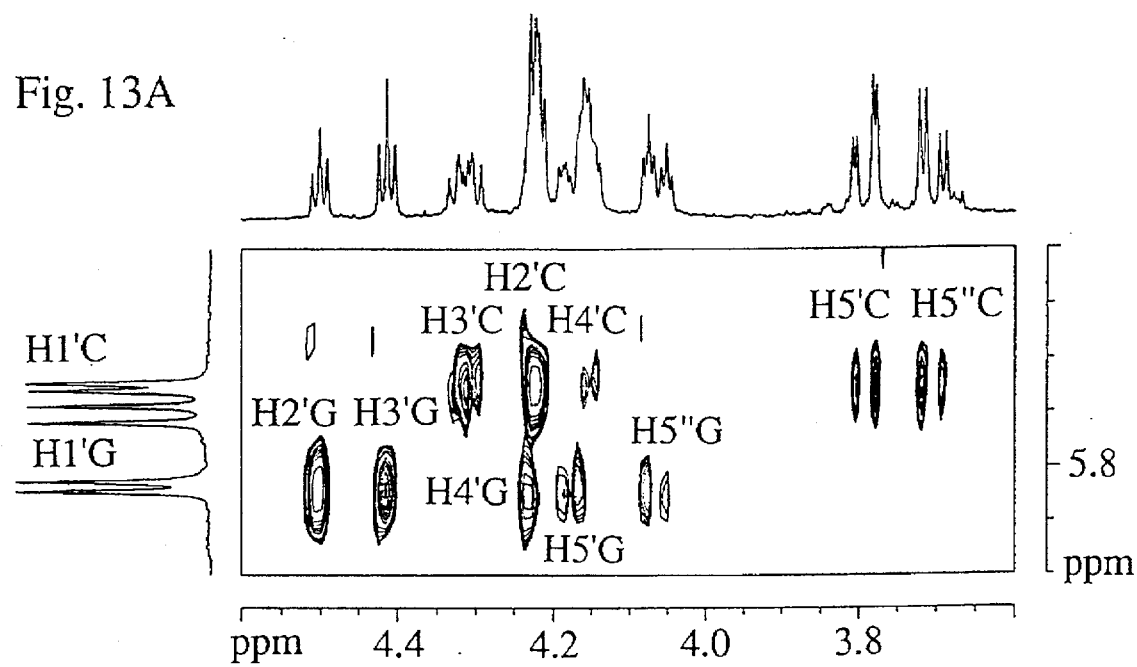
Figure 13B:
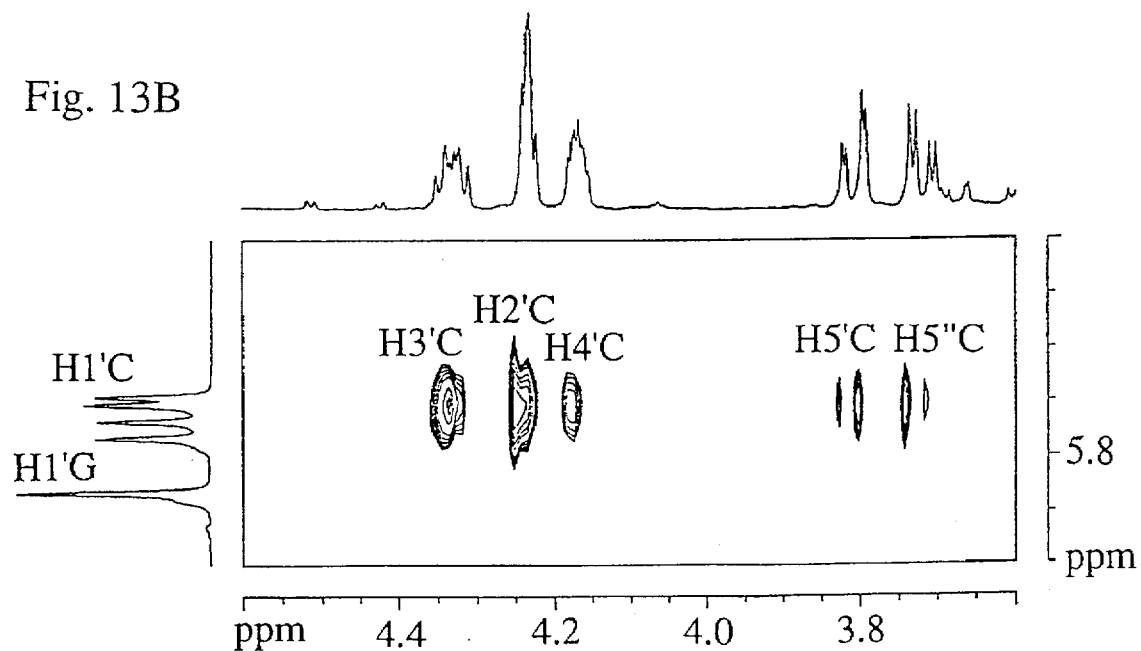

FIGS. 13(A) through 13(B): HOHAHA spectra of the natural and partially deuterated Cytidylyl-(3'→5')-guanosine (CpG) in $D_2O$ at 298K. Panel A represents the 2D spectrum for the non-deuterated CpG. Panel B represents the 2D spectrum of the partially deuterated CpG* where the 1'#,2',3',4'# and 5'/5" protons of the guanosine residue (pG*) are exchanged. In the 1D spectrum, the H1' appears as a singlet at 5.81 ppm while the H4' appears as a doublet at 4.2 ppm due to its coupling to the phosphorus of the 3"5' phosphate linkage. In the 2D spectrum, the J-network for the 3'-terminal residue has vanished.

Figure 14A:
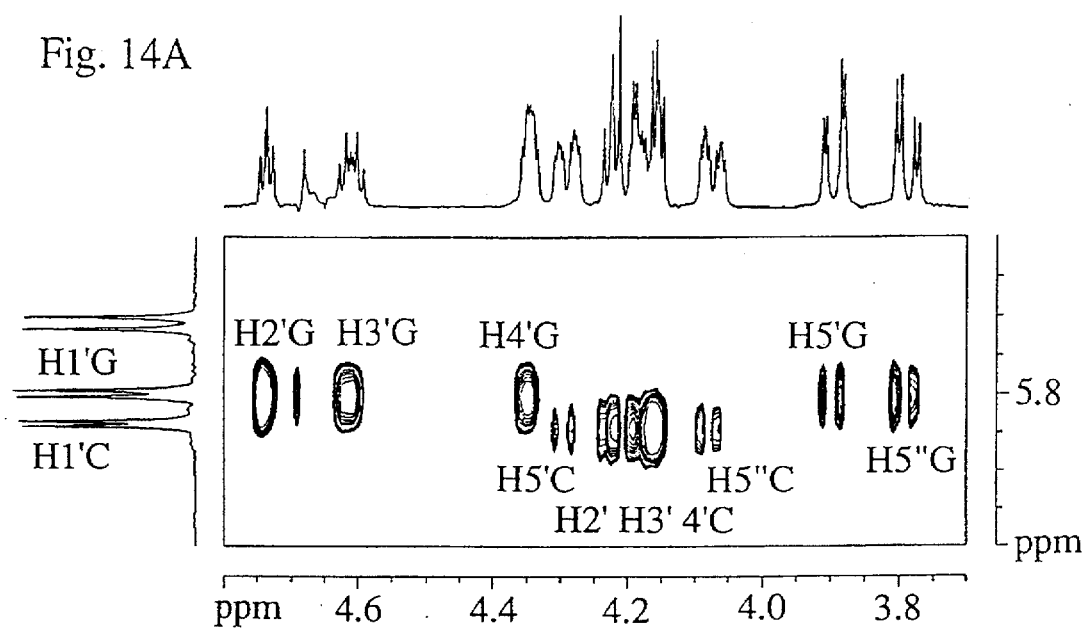
Figure 14B:
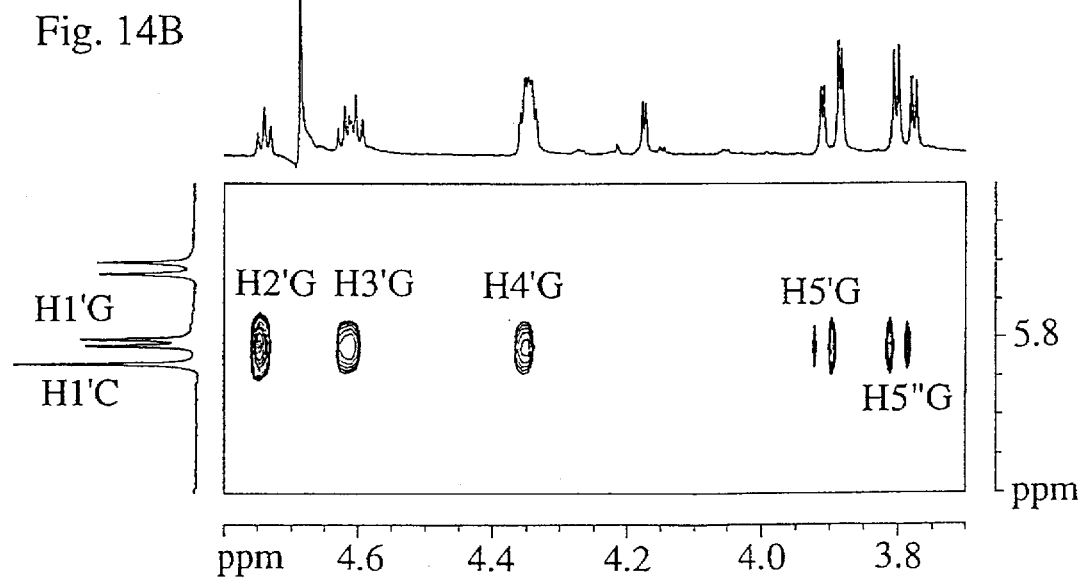

FIGS. 14(A) through 14(B): HOHAHA spectra of the natural and partially deuterated Guanylyl-(3'→5')-cytidine (GpC) in $D_2O$ at 298K. Panel A represents the 2D spectrum for the non-deuterated GpC. Panel B represents the 2D spectrum of the partially deuterated GpC* where the 1'#,2', 3',4'# and 5'/5" protons of the cytidine (pC*) residue are exchanged. In the 1D spectrum, the H1' appears as a singlet at 5.84 ppm while the H4' appears as a doublet at 4.2 ppm due to its coupling to the phosphorus of the 3"5' phosphate linkage. In the 2D spectrum, the J-network for the 3'-terminal residue has vanished.

Figure 15A:
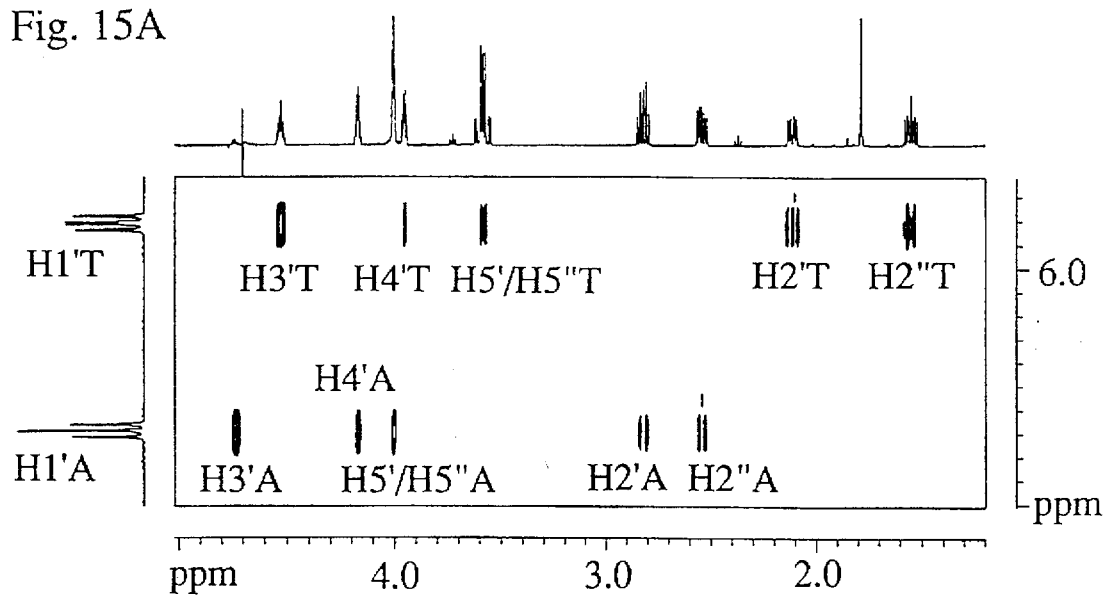
Figure 15B:
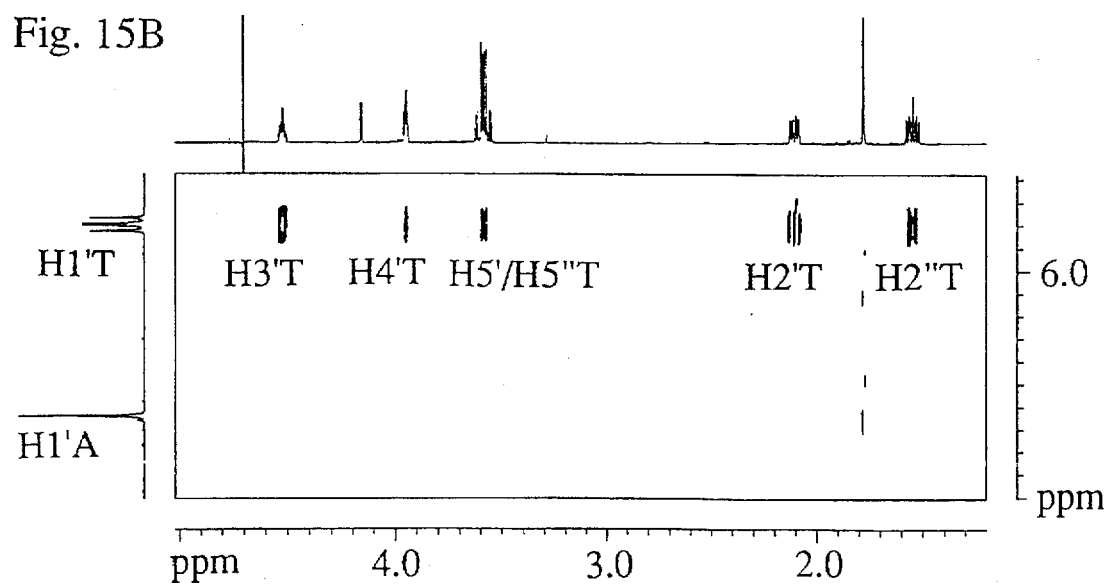

FIGS. 15(A) through 15(B): HOHAHA spectra of the natural and partially deuterated Thymidylyl-(3'→5')-2'-deoxyadenosine [d(TpA)] in $D_2O$ at 298K. Panel A represents the 2D spectrum for the non-deuterated d(TpA). Panel B represents the 2D spectrum of the partially deuterated d(TpA*) where the 1'#, 2', 2", 3', 4'# and 5'/5" protons of the adenosine (pA*) residue are exchanged. In the 1D spectrum, the H1' appears as a singlet at 6.38 ppm while the H4' appears as a doublet at 4.10 ppm due to its coupling to the 3"5' phosphorus of the phosphate linkage. In the 2D spectrum, the J-network for the 3'-terminal residue has vanished.

Figure 16A:
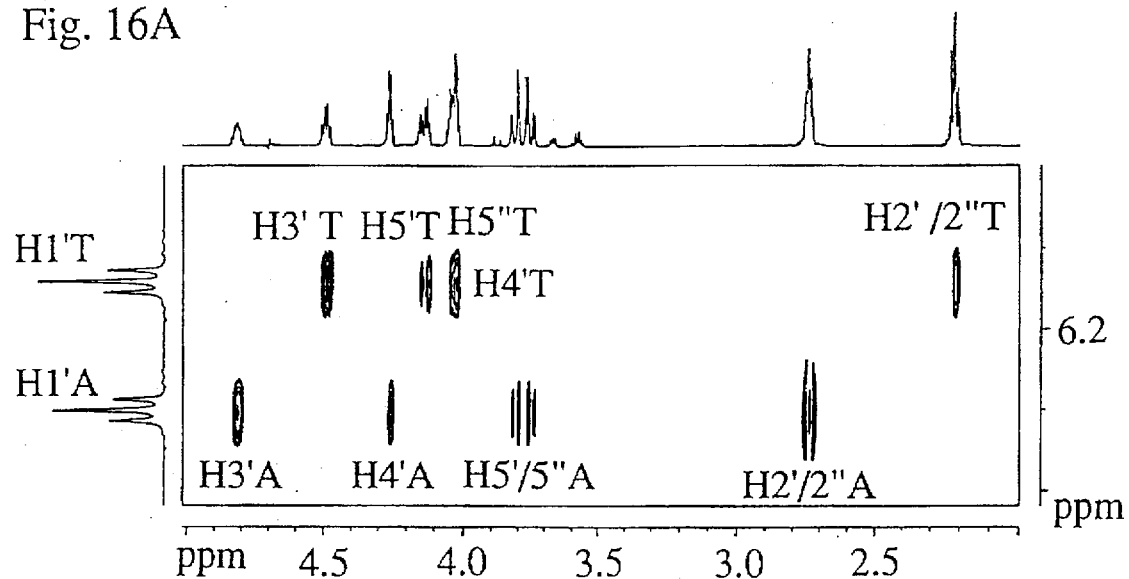
Figure 16B:
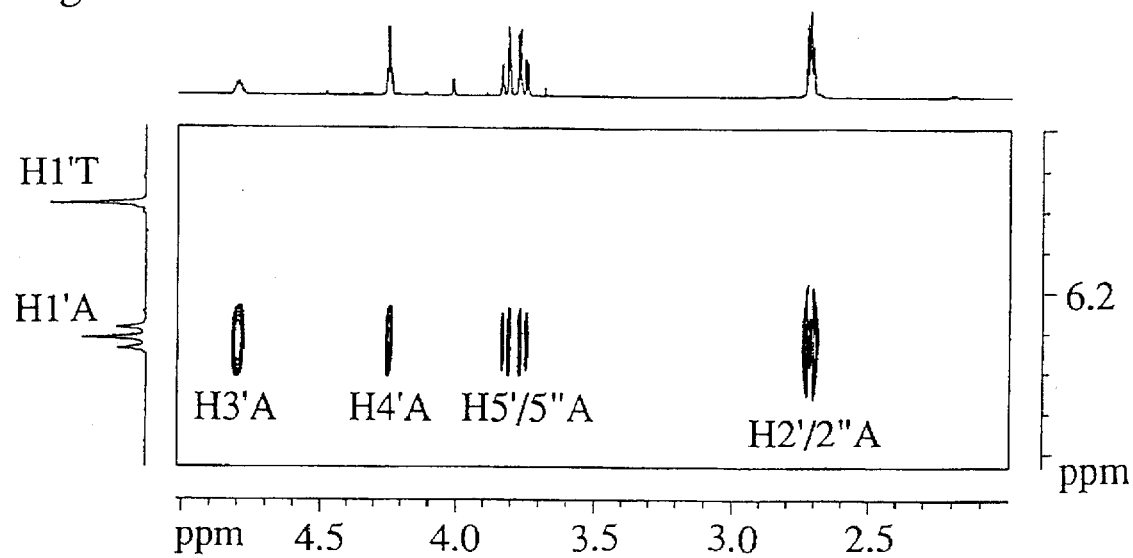

FIGS. 16(A) through 16(B): HOHAHA spectra of the natural and partially deuterated 2'-deoxyadenylyl-(3'→5')-thymidine [d(APT)] in $D_2O$ at 298K. Panel A represents the 2D spectrum for the non-deuterated d(ApT). Panel B represents the 2D spectrum of the partially deuterated d(ApT*) where the 1'#, 2', 2", 3', 4'# and 5'/5" protons of the thymidine (pT*) residue are exchanged. In the 1D spectrum, the H1' appears as a singlet at 6.15 ppm while the H4' appears as a doublet at 4.00 ppm due to its coupling to the phosphorus of the 3"5' phosphate linkage. In the 2D spectrum, the J-network for the 3'-terminal residue has vanished.

Figure 17A:
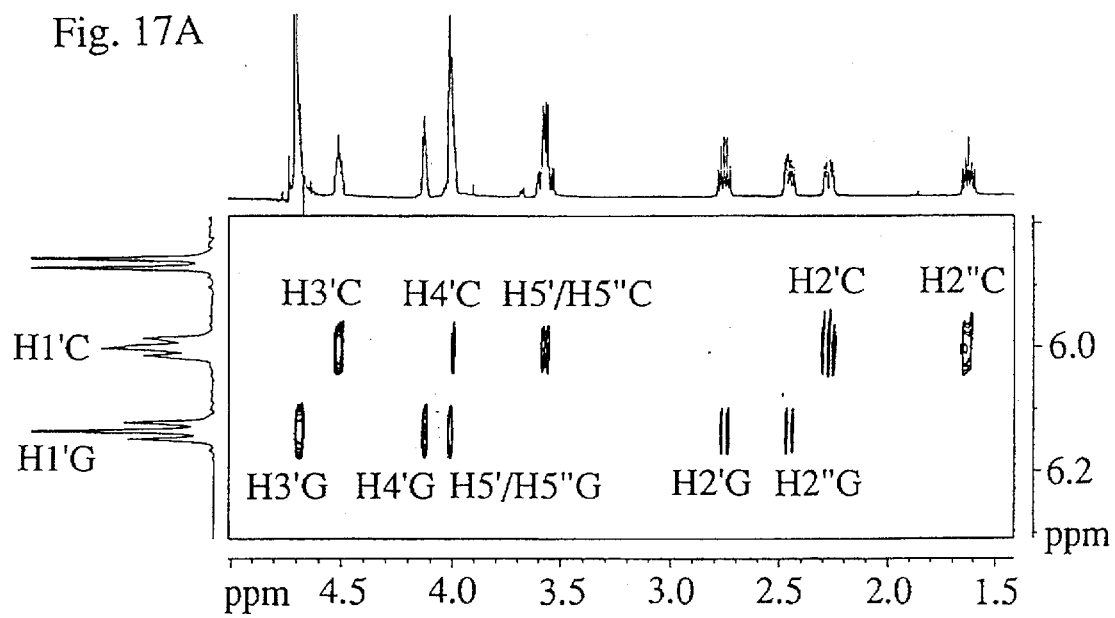
Figure 17B:
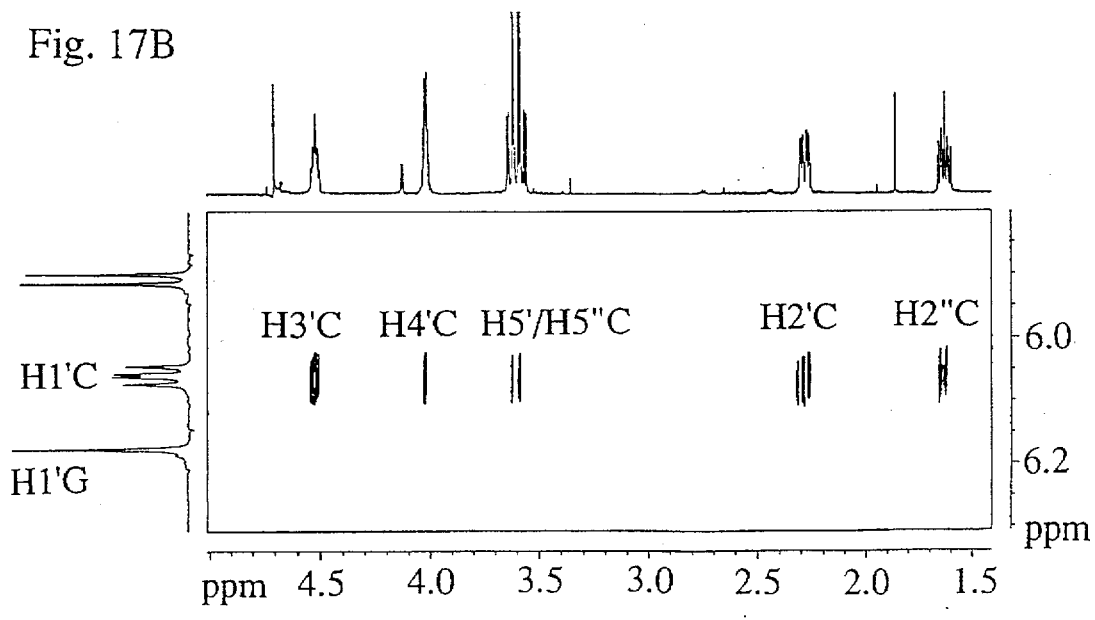

FIGS. 17(A) through 17(B): HOHAHA spectra of the natural and partially deuterated 2'-deoxycytidylyl-(3'→5')-2'-deoxyguanosine [d(CpG)] in $D_2O$ at 298K. Panel A represents the 2D spectrum for the non-deuterated d(CpG). Panel B represents the 2D spectrum of the partially deuterated d(CpG*) where the 1'#,2',3',4'# and 5'/5" protons of the guanosine (pG*) residue are exchanged. In the 1D spectrum, the H1' appears as a singlet at 6.19 ppm while the H4' appears as a doublet at 4.10 ppm due to its coupling to the phosphorus of the 3"5' phosphate linkage. In the 2D spectrum, the J-network for the 3'-terminal residue has vanished.

Figure 18A:
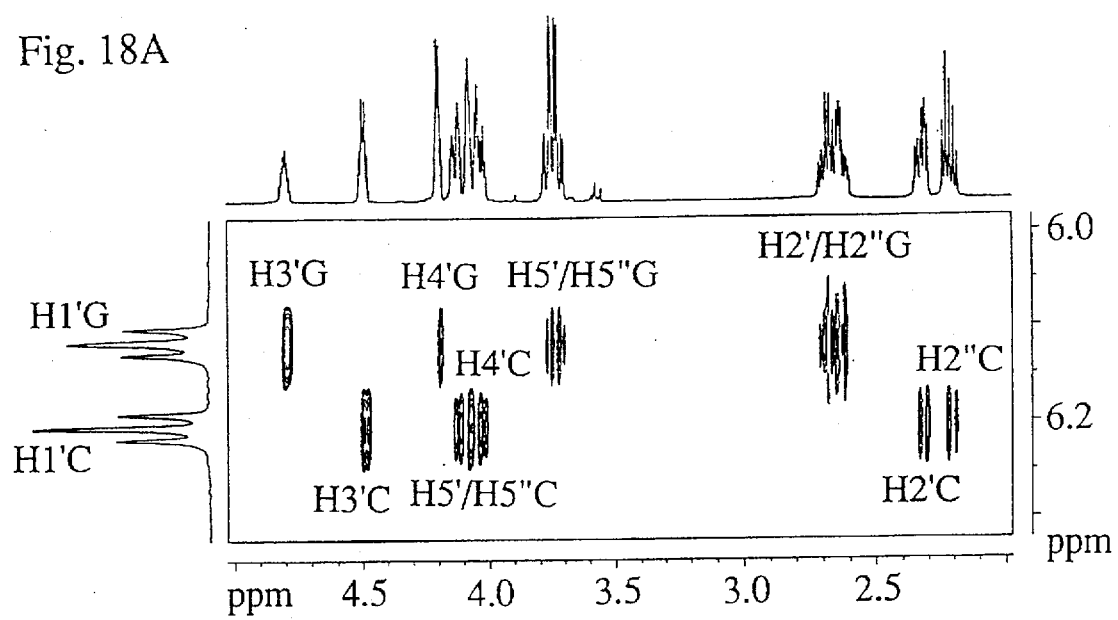
Figure 18B:
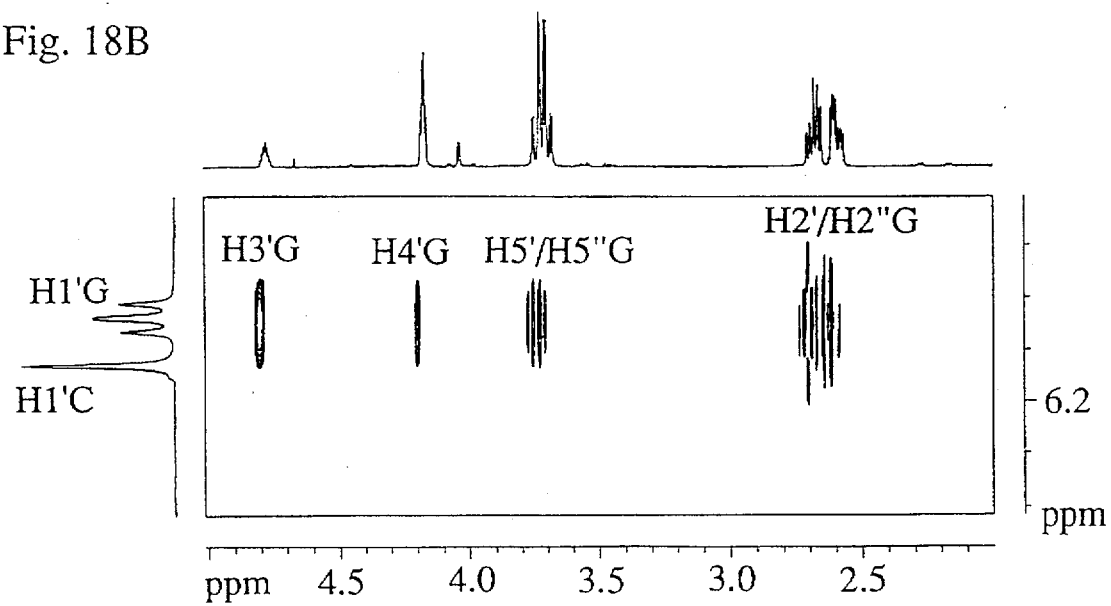

FIGS. 18(A) through 18(B): HOHAHA spectra of the natural and partially deuterated 2'-deoxyguanylyl-(3'→5')-2'-deoxycytidine [d(GpC)] in $D_2O$ at 298K. Panel A represents the 2D spectrum for the non-deuterated d(GpC). Panel B represents the 2D spectrum of the partially deuterated d(GpC*) where the 1'#, 2', 2", 3', 4'# and 5'/5" protons of the cytosine (pC*) residue are exchanged. In the 1D spectrum, the H1' appears as a singlet at 6.19 ppm while the H4' appears as a doublet at 4.1 ppm due to its coupling to the phosphorus of the 3"5' phosphate linkage. In the 2D spectrum, the J-network for the 3'-terminal residue has vanished.

Figure 19A:
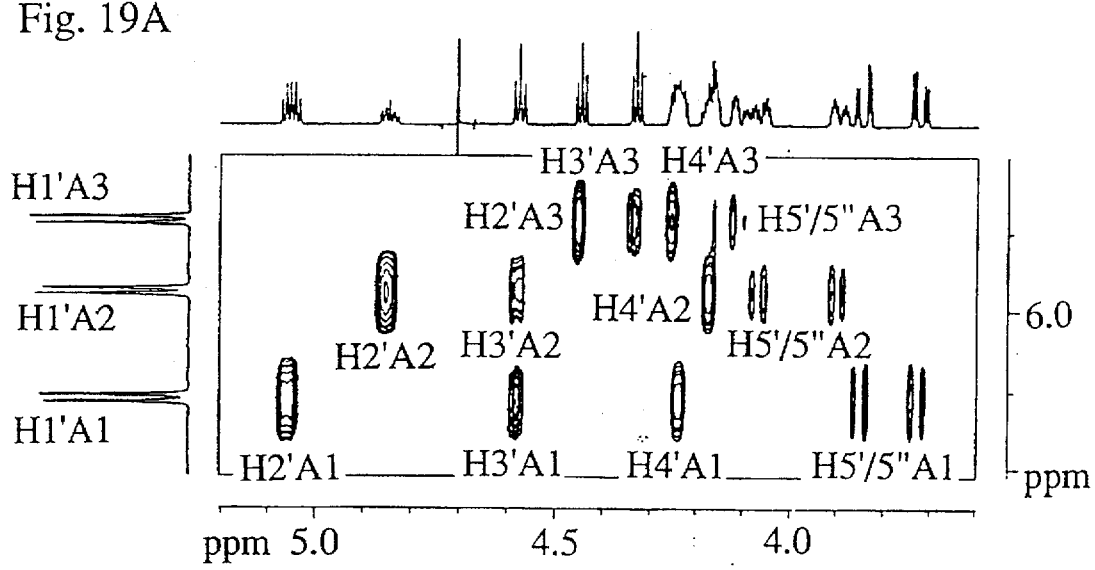
Figure 19B:
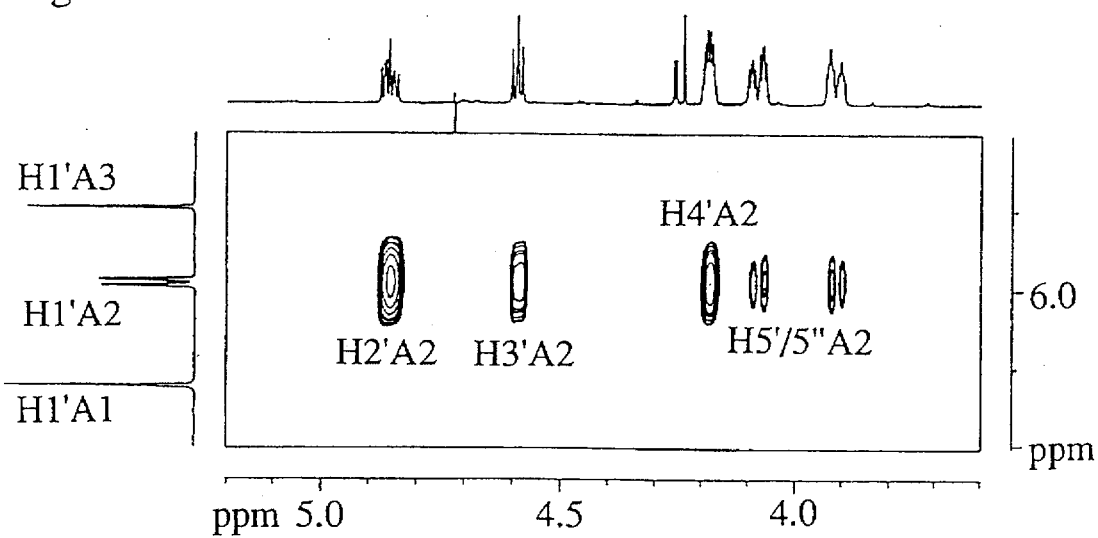

FIGS. 19(A) through 19(B): HOHAHA spectra of the natural and partially deuterated 2,5A core $A^1(2'→5')A^2(2'→5')A^3$ in $D_2O$ at 308K. Panel A represents the 2D spectrum for the non-deuterated $A^1(2'→5')A^2(2'→5')A^3$. Panel B represents the 2D spectrum of the partially deuterated $A^{1*}(2'→5')A^2(2'→5')A^{3*}$ where the 1'#,2',3',4'# and 5'/5" protons of the $A^{1*}$ and $A^{3*}$ residues are exchanged. In the 1D spectrum, the H1' of $A^{1*}$ and $A^{3*}$ appears as a singlet at 6.1 and 5.9 ppm respectively. The H4' of $A^{1*}$ appears as a singlet at 4.2 ppm while the H4' of $A^{3*}$ appears as a doublet at 4.25 ppm due to its coupling to the phosphorus of the $A^2(3'→5')A^3$ phosphate linkage. In the 2D spectrum, the J-network for the 5'-terminal residue $A^{1*}$ and 3'-terminal residue $A^{3*}$ has vanished.

FIGS. 20(A) through 20(B): 2D $^{31}P$-$^1H$ chemical shift correlation spectra of the natural and partially-deuterated 2,5A core $A^1(2'→5')A^2(2'→5')A^3$ in $D_2O$ at 308K. Panel A represents the 2D spectrum for the non-deuterated $A^1(2'→5')A^2(2'→5')A^3$. The $A^1(2'→5')A^2$ phosphorus shows a cross peak with the H2'$A^1$ and H5'/H5"$A^2$. The $A^2(2'→5')A^3$ phosphorus shows a cross peak with the H2'$A^2$ and H5'/H5"$A^3$. Panel B represents the 2D spectrum of the partially deuterated $A^{1*}$ $(2'→5')A^2(2'→5')A^{3*}$ where the 1'#,2',3',4'# and 5'/5" protons of the $A^{1*}$ and $A^{3*}$ residues are exchanged. The cross peaks between the $A^{1*}$ $(2'→5')A^2$ phosphorus and H2'$A^{1*}$ and between the $A^2(2'→5')A^{3*}$ phosphorus and H5'/H5"$A^{3*}$ have vanished.

FIGS. 21(A) through (F) DQF-COSY spectra of the natural and partially deuterated Uridylyl-(3'→5')-adenosine (UpA) in $D_2O$ at 298K. Panel A: 2D spectrum of the natural UpA. The cross peaks used for the determination of the vicinal $^3J_{HH}$ coupling constants are shown in the numbered boxes: (1) H1'U-H2'U, (2): H2'U-H3'U, H3'U-H4'U cross peaks, and H4'A-H5'A, H4'A-H5"A, (3) H4'U-H5'U, H4'U-H5"U, (4) H1'A-H2'A, (5) H3'A-H4'A, (6) H2'A-H3'A. Panel B; Expansion of the cross peak in box 2. Panel C: Vertical slice through the cross peak at the site indicated by an arrow. The determination of the J-couplings is complicated due to the overlap of the H2'U-H3'U with the H4'A-H5'A cross peaks. Similarly, The H3'U-H4'U cross peak overlap with the H4'A-H5"A cross peak. Panel D: 2D spectrum of UpA* where the 1'#,2', 3', 4'# and 5'/5" of A* have been exchanged with deuterium. The empty boxes show that all cross peaks involving the adenosine residue have vanished. Panel E: Expansion of the cross peak in box 2. Panel F: Vertical slice through the cross peak at the site indicated by an arrow, which now contains only the H2'U-H3'U and H3'U-H4'U allowing an easy extraction of the coupling constants.

Figure 22A:
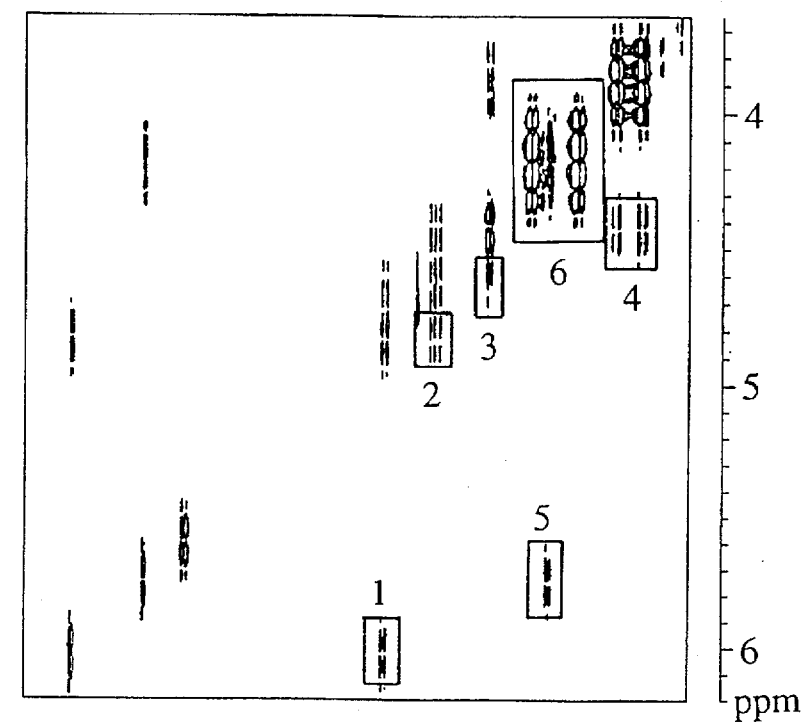
Figure 22B:
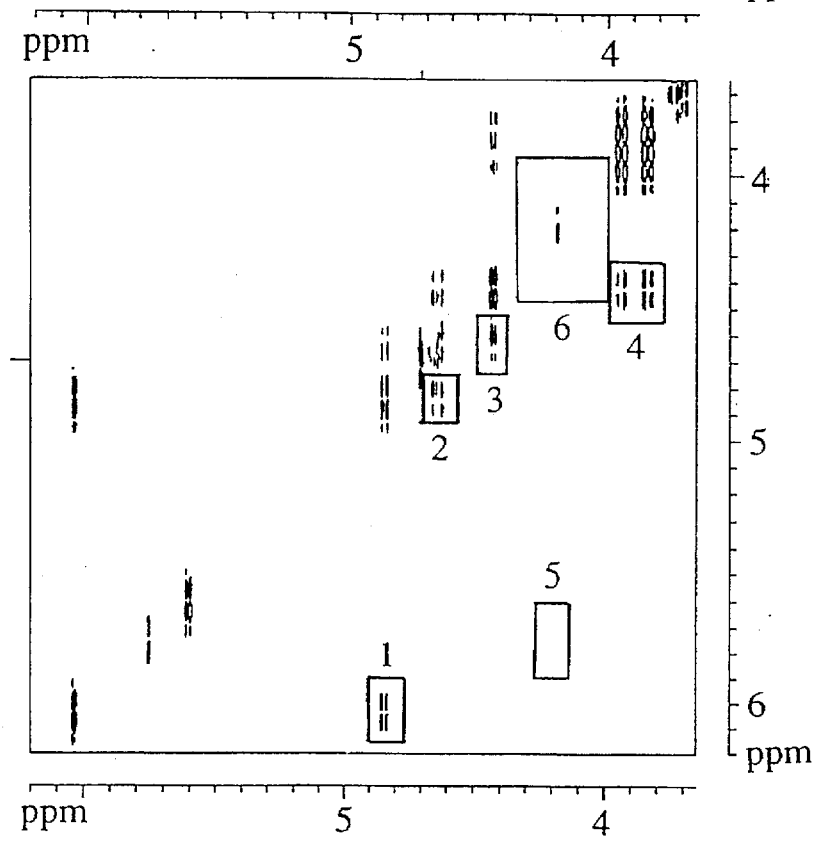

FIGS. 22(A) and 22(B): DQF-COSY spectra of the natural and partially deuterated adenylyl-(3'→5')-uridine (ApU) in $D_2O$ at 298K. Panel A: 2D spectrum of the natural ApU. The cross peaks used for the determination of the vicinal $^3J_{HH}$ coupling constants are shown in the numbered boxes: (1) H1'-H2'A, (2) H2'-H3'A, (3) H3'-H4'A, (4) H4'-H5'A, H4'-H5"A, (5) H1'-H2'U, (6) H2'-H3', H3'-H4', H4'-H5' and H4'-H5"U. Panel B: 2D spectrum of ApU* where the 1'#,2', 3', 4'# and 5'/5" of pU* have been exchanged with deuterium. The empty boxes show that all cross peaks involving the pU* residue have vanished.

FIGS. 23(A) and 23(B): DQF-COSY spectra of the natural and partially deuterated Guanylyl-(3'→5')-cytidine (GpC) in $D_2O$ at 298K. Panel A: 2D spectrum of the natural GpC. The cross peaks used for the determination of the vicinal $^3J_{HH}$ coupling constants are shown in the numbered boxes: (1) H1'C-H2'G, (2): H3'C-H4'G, (3) H, (4) H4'-H5', H4'-H5"G, (5) H1'-H2'C, H2'-H3'C, H3'-H4'C, H4'-H5'C and H4'-H5"C. Panel B: 2D spectrum of GpC* where the 1'#,2', 3', 4'# and 5'/5" of pC* have been exchanged with deuterium. The empty boxes show that all cross peaks involving the pC* residue have vanished.

FIGS. 24(A) and 24(B): DQF-COSY spectra of the natural and partially deuterated Cytidylyl-(3'→5')-guanosine (CpG) in $D_2O$ at 298K. Panel A: 2D spectrum of the natural CpG. The cross peaks used for the determination of the vicinal $^3J_{HH}$ coupling constants are shown in the numbered boxes: (1) H1'C-H2'C, (2): H3'C-H4'C, (3) H2'C-H3'C, (4) H4'C-H5'C and H4'C-H5"C, (5) H1'G-H2'G, (6) H2'G-H3'G, (7) H3'G-H4'G, (8) H4'G-H5'G. Panel B: 2D spectrum of CpG* where the 1'#,2',3',4'# and 5'/5" of pG* have been exchanged with deuterium. The empty boxes show that all cross peaks involving the pG* residue have vanished.

Figure 25A:
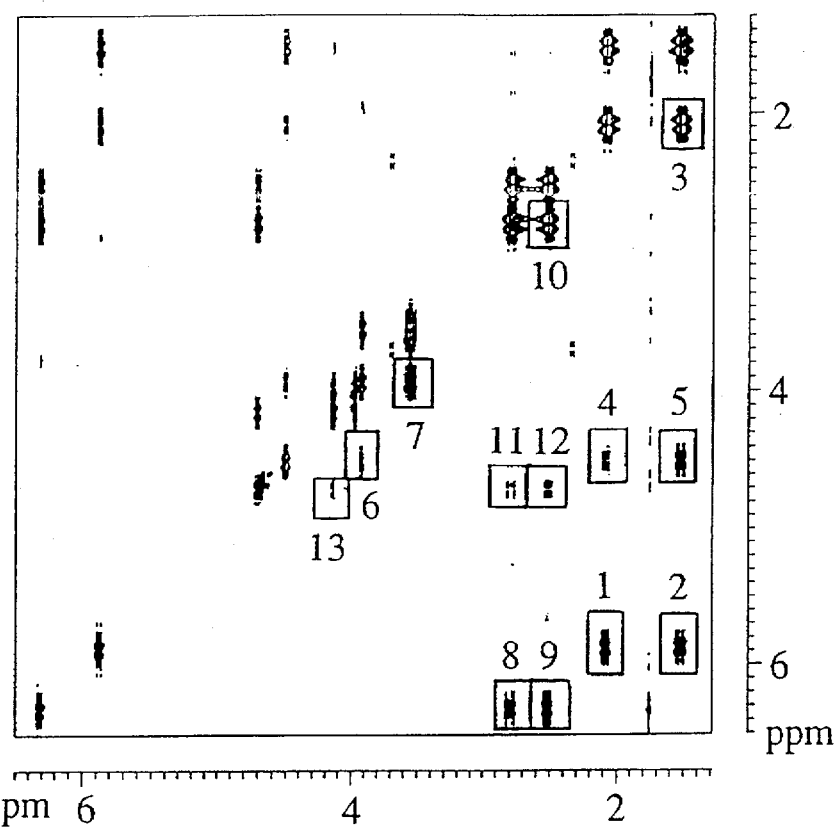
Figure 25B:
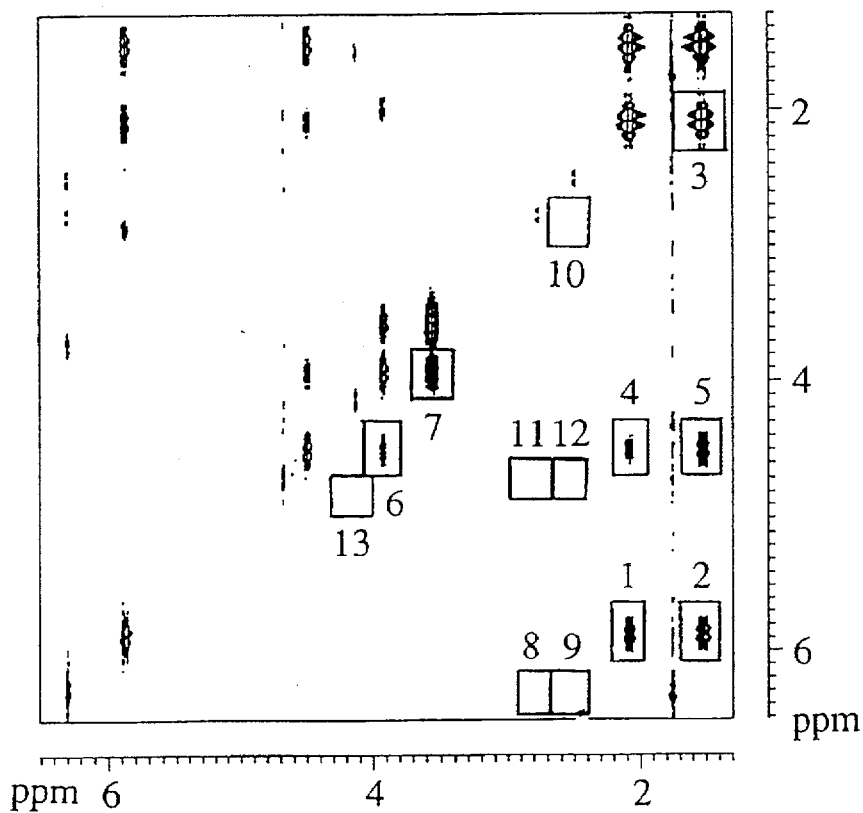

FIGS. 25(A) and 25(B): DQF-COSY spectra of natural and partially deuterated Thymidylyl-(3'→5')-2'-deoxyadenosine [d(TpA)] in $D_2O$ at 298K. Panel A: 2D spectrum of the natural d(TpA). The cross peaks used for the determination of the vicinal $^3J_{HH}$ coupling constants are shown in the numbered boxes: (1) H1'-H2"T (2) H1'-H2'T, (3) H2'-H2"T (4) H2"-H3'T, (5) H2'-H3'T, (6) H3'-H4'T, (7) H4'-H5'T, H4'-H5"T, (8) H1'-H2'A (9) H1'-H2"A (10) H2'-H2"A, (11) H2'-H3'A (12) H2"-H3'A, (13) H3'-H4'A. Panel B: 2D spectrum of d(TpA*) where the 1'#,2',3',4'# and 5'/5" of pA* have been exchanged with deuterium. The empty boxes show that all cross peaks involving the pA* residue have vanished.

Figure 26A:
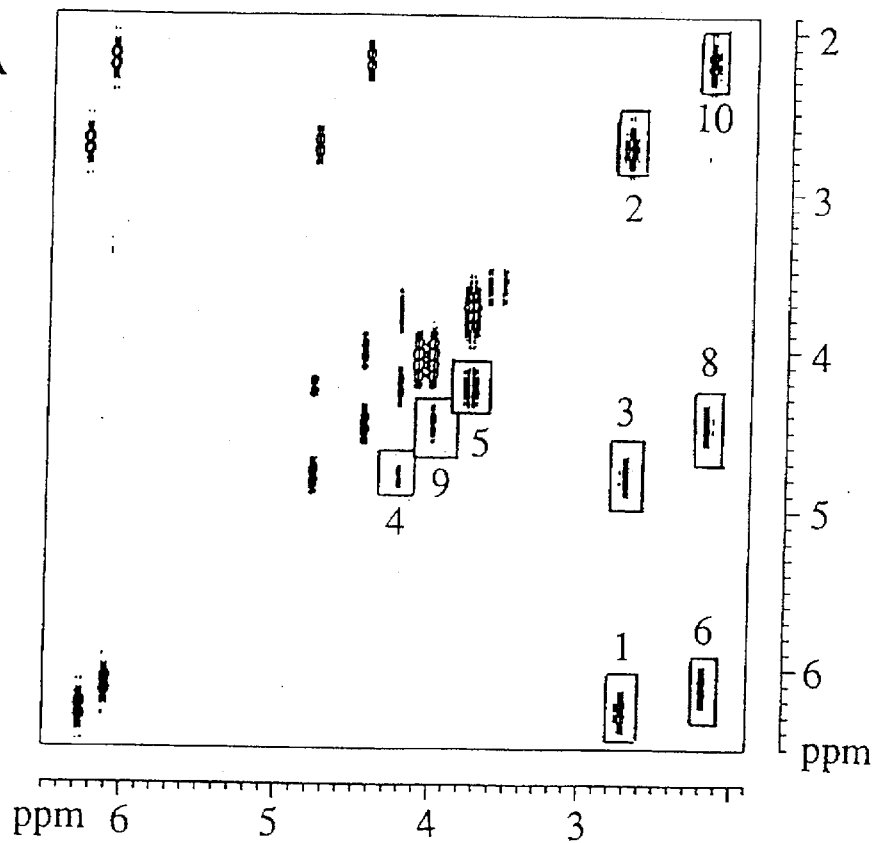
Figure 26B:
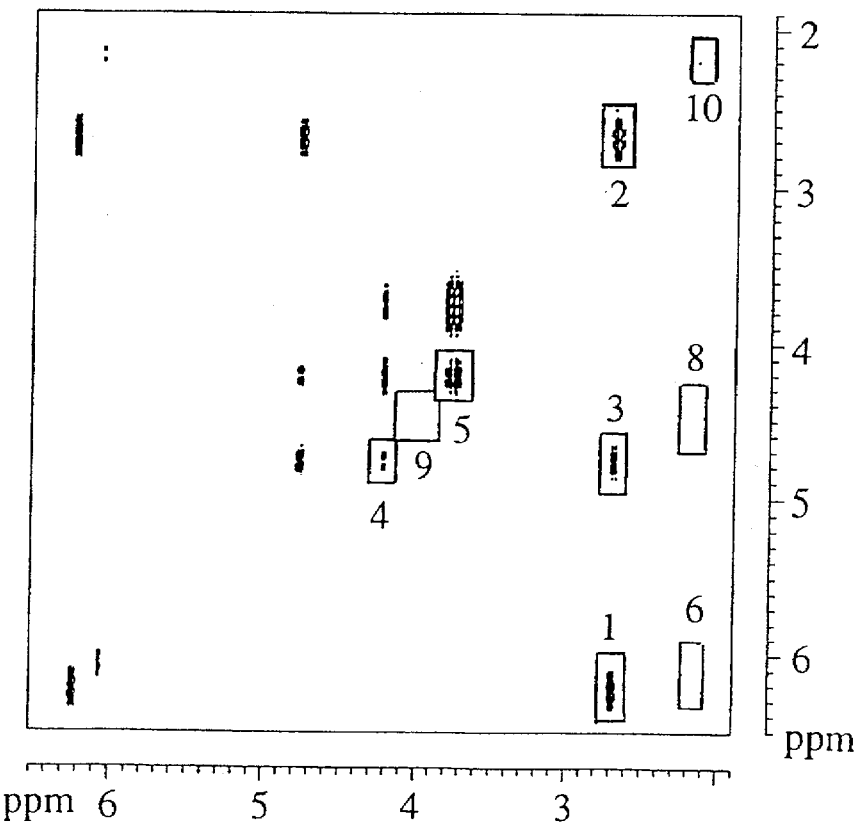

FIGS. 26A and 26(B): DQF-COSY spectra of natural and partially deuterated 2'-deoxyadenylyl-(3'→5')-thymidine [d(APT)] in $D_2O$ at 298K. Panel A: 2D spectrum of the natural d(ApT). The cross peaks used for the determination of the vicinal $^3J_{HH}$ coupling constants are shown in the numbered boxes: (1) H1'-H2'A, H1'-H2"A, (2) H2'-H2"A (3) H2'-H3'A, H2"-H3'A (4) H3'-H4'A , (5) H4'-H5'A, H4'-H5"A (6) H1'-H2'T, H1'-H2"T, (7) H2'-H2"T, (8) H2'-H3'T, H2"-H3'T, (9) H3'-H4'T. Panel B: 2D spectrum of d(ApT*) where the 1'#,2',3',4'# and 5'/5" of pT* have been exchanged with deuterium. The empty boxes show that all cross peaks involving the pT* residue have vanished.

Figure 27A:
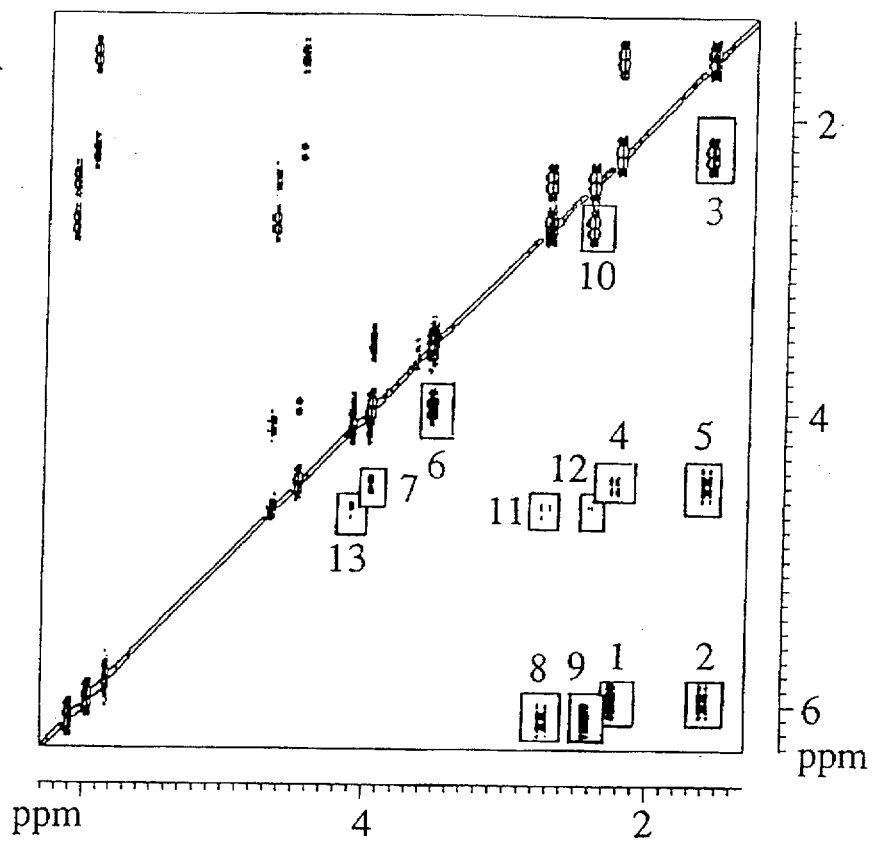
Figure 27B:
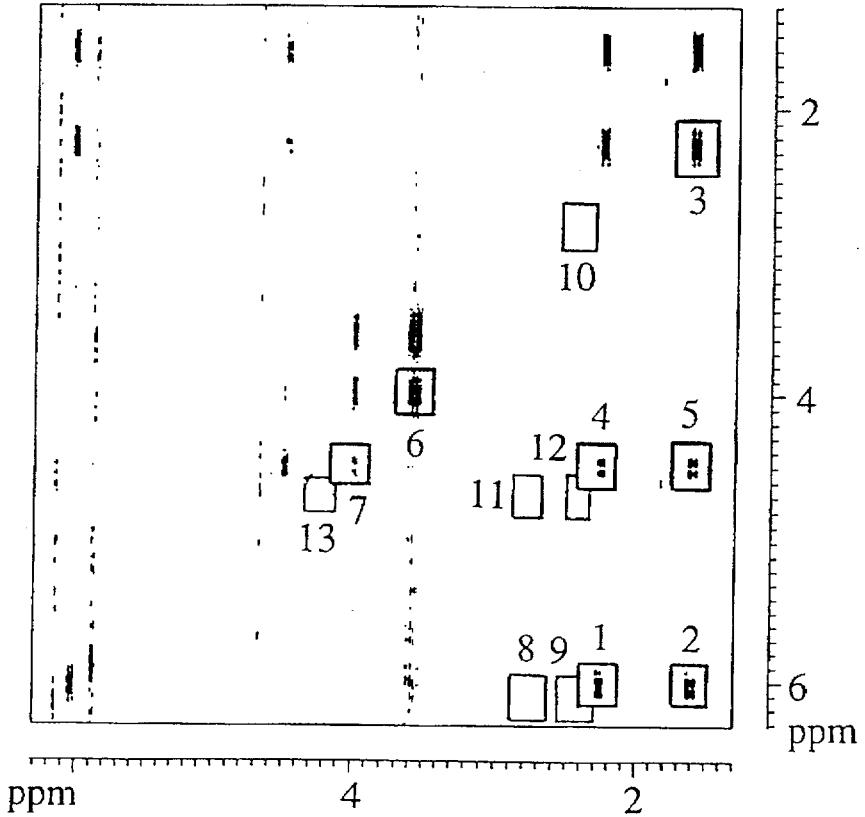

FIGS. 27(A) and 27(B): DQF-COSY spectra of natural and partially deuterated 2'-deoxycytidylyl-(3'→5')-2'-deoxyguanosine [d(CpG)] in $D_2O$ at 298K. Panel A: 2D spectrum of the natural d(CpG). The cross peaks used for the determination of the vicinal $^3J_{HH}$ coupling constants are shown in the numbered boxes: (1) H1'-H2'C, (2) H1'-H2"C (3) H2'-H2"C, (4) H2'-H3'C, (5) H2"-H3'C, (6) H4'-H5', H4'-H5"C, (7) H3'-H4'C, (8) H1'-H2'G, (9) H1'-H2"G (10) H2'-H2"G, (11) H2'-H3'G, (12) H2"-H3'G, (13) H3'-H4'G. Panel B: 2D spectrum of d(CpG*) where the 1'#,2',3',4'# and 5'/5" of G* have been exchanged with deuterium. The empty boxes show that all cross peaks involving the pG* residue have vanished.

Figure 28A:
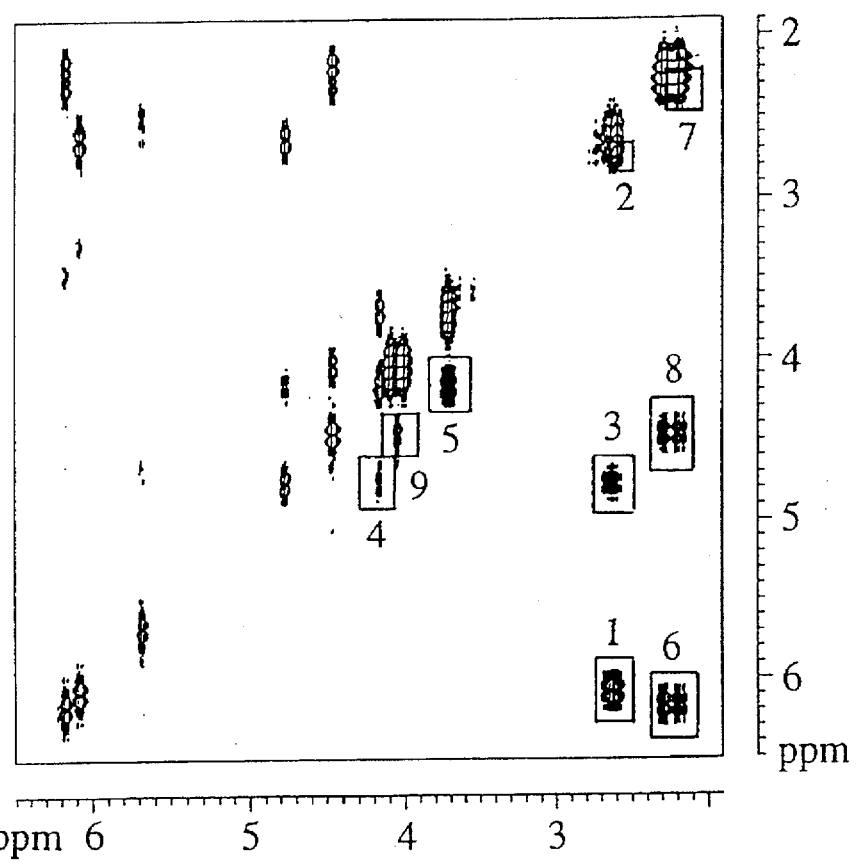
Figure 28B:
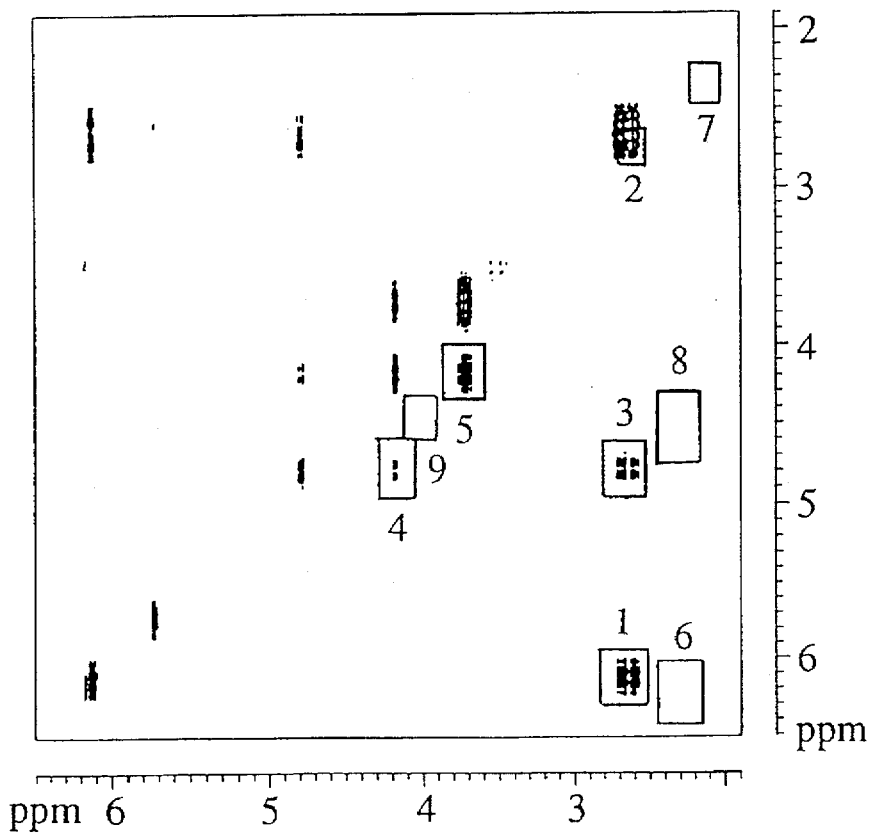
Figure 32B:
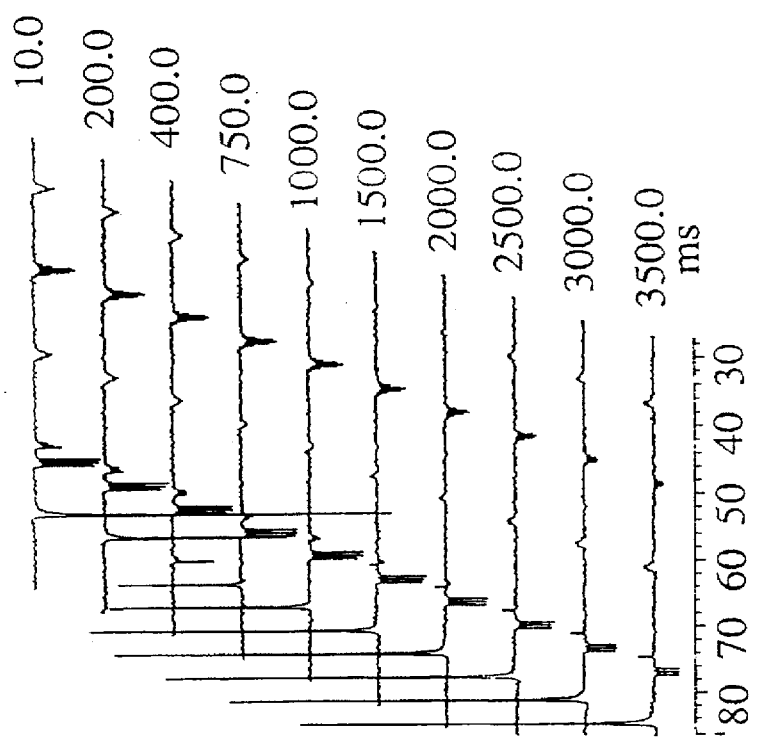
Figure 32A:
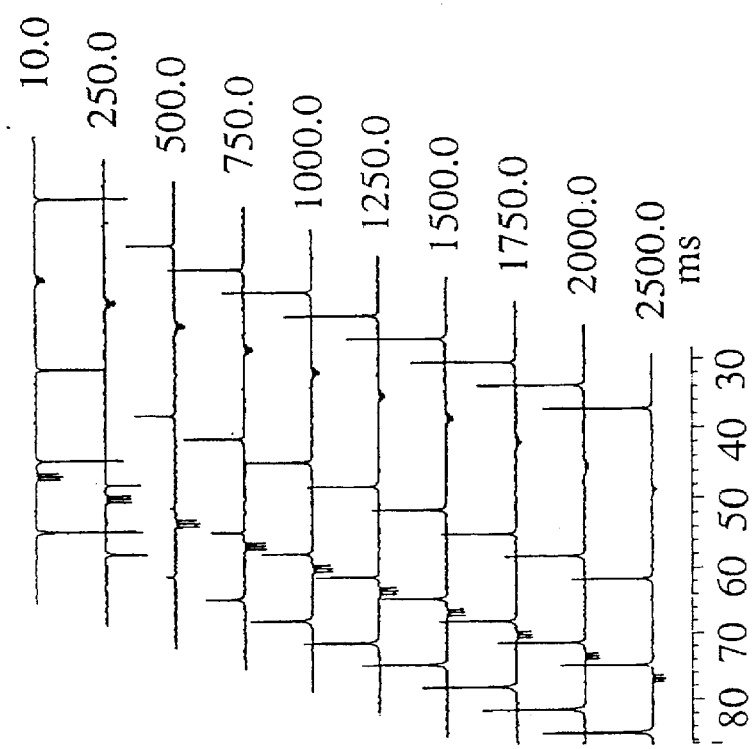
Figure 32D:
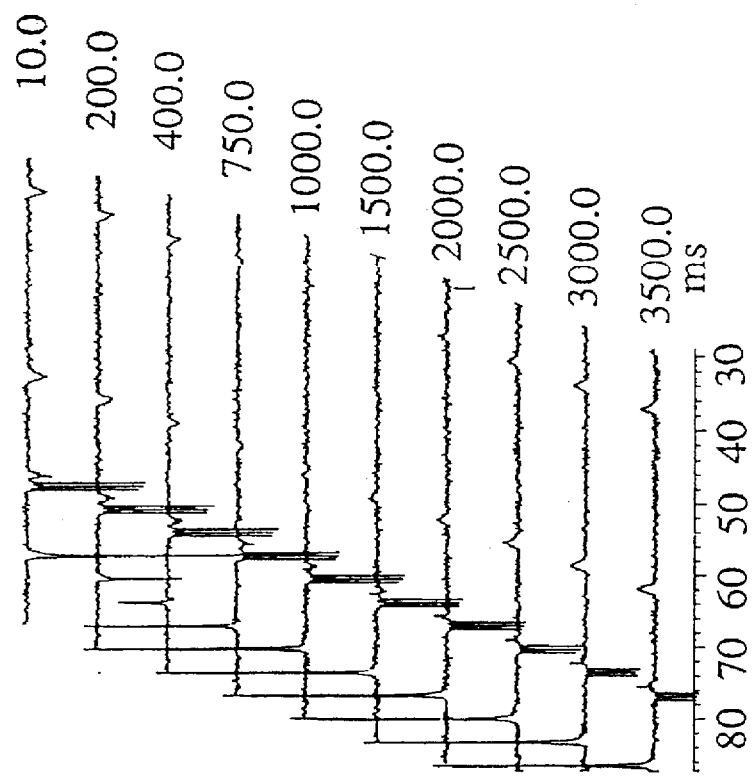
Figure 32C:
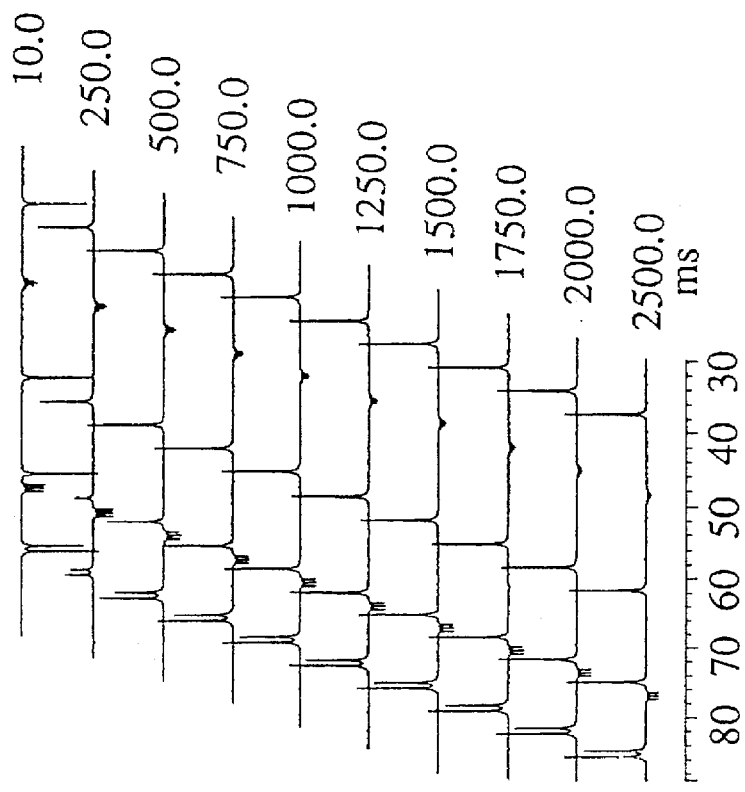
Figure 33B:
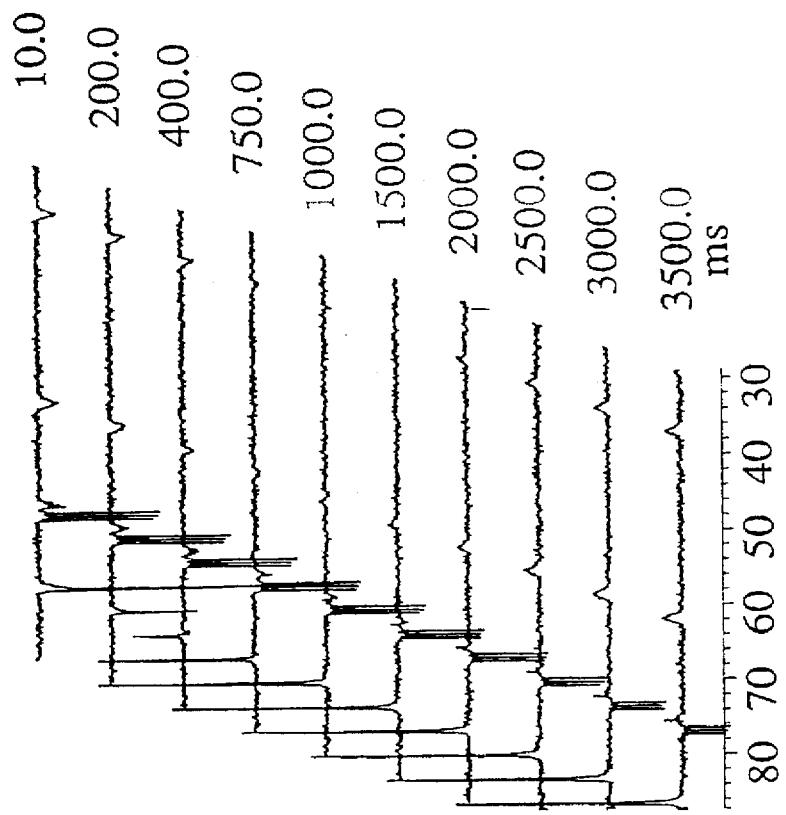
Figure 33A:
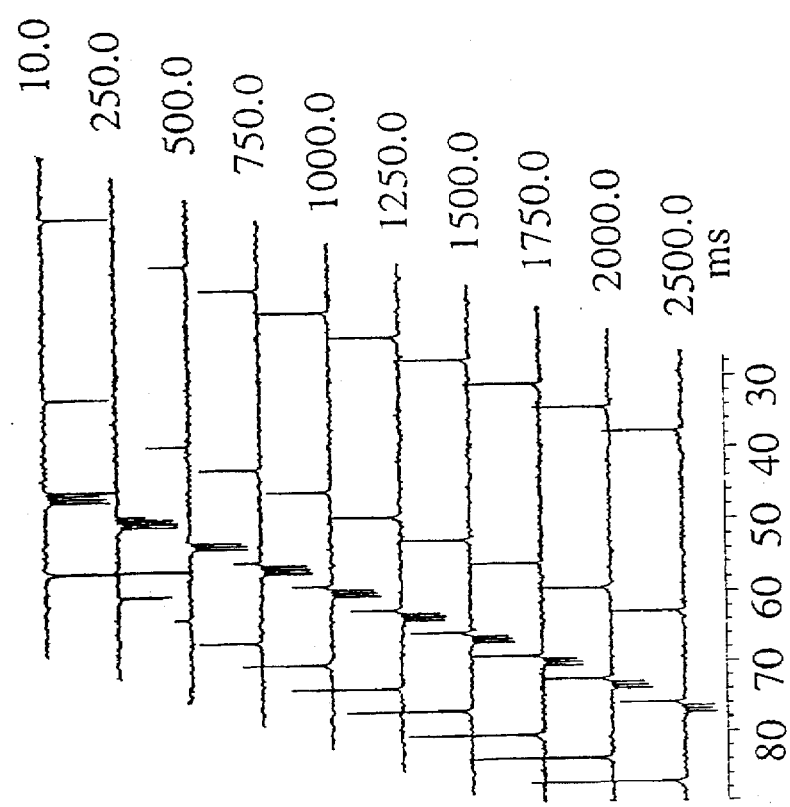

FIGS. 28(A) and 28(B): DQF-COSY spectra of natural and partially deuterated 2'-deoxyguanylyl-(3'→5')-2'-deoxycytidine [d(GpC)] in $D_2O$ at 298K. Panel A: 2D spectrum of the natural d(GpC). The cross peaks used for the determination of the vicinal $^3J_{HH}$ coupling constants are shown in the numbered boxes: (1) H1'-H2'G, H2"-H3'G, (2) H2'-H2"G, (3) H2'-H3'G, H2"-H3'G, (4) H3'-H4'G, (5) H4'-H5'G, H4'-H5"G, (6) H1'-H2'C, H1'-H2"C, (7) H2'-H2"C, (8) H2'-H3'C, H2"-H3'C, (9) H3'-H4'C. Panel B: 2D spectrum of d(GpC*) where the 1'#,2',3',4'# and 5'/5" of pC* have been exchanged with deuterium. The empty boxes show that all cross peaks involving the pC* residue have vanished.

FIGS. 29(A) and 29(B): DQF-COSY spectra of natural and partially deuterated 2,5A core $A^1(2'→5')A^2(2'→5')A^3$ in $D_2O$ at 308K. Panel A represents the 2D spectrum for the non-deuterated $A^1(2'→5')A^2(2'→5')A^3$. The cross peaks used for the determination of the vicinal $^3J_{HH}$ coupling constants are shown in the numbered boxes: (1) H1'-H2'A$^1$, (2) H2'-H3'A$^1$, (3) H3'-H4'A$^1$, (4) H4'-H5'A$^1$, (5) H4'-H5"A$^1$, (6) H1'-H2'A$^2$, (7) H2'-H3'A$^2$, (8) H3'-H4'A$^2$, (9) H4'-H5'A$^2$, (10) H4'-H5"A$^2$, (11) H1'-H2'A$^3$, (12) H2'-H3'A$^3$, (13) H3'-H4'A$^3$, (14) H4'-H5', H4'-H5"A$^3$, Panel B represents the 2D spectrum of the partially deuterated A$^1$* (2'→5')A$^2$(2'→5')A$^3$* where the 1'#,2',3',4'# and 5'/5" of A$^1$* and A$^3$* have been exchanged with deuterium. The empty boxes show that all cross peaks involving the A$^1$* and A$^3$* residues have vanished.

FIGS. 30(A1)–30(A2), 30(B1)–30(B2), 30(C1)–30(C2), 30(D1)–30(D2): $^{13}C$ INEPT NMR spectra of natural and partially deuterated deoxynucleosides at 298K in CDCl$_3$. (A$_2$): Natural 2'-deoxycytidine [dC], (A$_1$): Deuterated 2'-deoxycytine [dC*], (B$_2$): Natural 2'-deoxyadenosine [dA], (B$_1$): Deuterated 2'-deoxyadenosine [dA*], (C$_2$): Natural 2'-deoxyguanosine [dG], (C$_1$): Deuterated 2'-deoxyguanosine [dG*], (D$_2$): Natural thymidine (T), (D$_1$): Deuterated thymidine [T*]. In dC*, dA*, dG* and T*, the 2', 2", 3', 5' and 5" protons have been exchanged with deuterium (>97% $^2$H). The H1' is ~20% deuterated while the H4' is ~85% deuterated. In dC*, dA*, dG* and T*, the transfer of polarization from $^1$H to $^{13}$C arises only for the C1' and C4' carbons. The resonances of the carbons covalently bonded to deuterium, C2', C3' and C5', are effectively eliminated.

FIGS. 31(A1)–31(A2), 31(B1)–31(B2), 31(C1)–31(C2), 31(D1)–31(D2): $^{13}C$ {$^1$H} INEPT NMR experiments of natural and partially deuterated deoxynucleosides at 298K in CDCl$_3$. (A$_2$): Natural 2'-deoxycytidine [dC], (A$_1$): Deuterated 2'-deoxycytine [dC*], (B$_2$): Natural 2'-deoxyadenosine [dA], (B$_1$): Deuterated 2'-deoxyadenosine [dA*], (C$_2$): Natural 2'-deoxyguanosine [dG], (C$_1$): Deuterated 2'-deoxyguanosine [dG*], (D$_2$): Natural thymidine [T], (D$_1$): Deuterated thymidine [T*]. In dC*, dA*, dG* and T*, the 2', 2", 3', 5' and 5" protons have been exchanged with deuterium (>97% $^2$H). The H1' is ~20% deuterated while the H4' is ~85% deuterated. In dC*, dA*, dG* and T*, the transfer of polarization from $^1$H to $^{13}$C arises only for the C1' and C4' carbons. The resonances of the carbons covalently bonded to deuterium, C2', C3' and C5', are effectively eliminated.

FIGS. 32(A) through 32(D): $T_1$ measurements by inversion recovery experiments ($^{13}$C-NMR) of natural and partially deuterated deoxynucleosides. (A): natural Thymidine (T), $T_1$: C1' (d 84.9)=0.7s, C2' (d 37.2)=0.41s, C3' (d 74.8)=0.71s, C4' (d 84.8)=0.65s, C5' (d 61.6)=0.36s, (B): Deuterated Thymidine [T*, where the 2', 2", 3', 5' and 5" protons have been exchanged with deuterium (>97% $^2$H). The 1'# is ~20% deuterated while the 4'# is ~85% deuterated], $T_1$: C1'=0.7s, C2'=1.82s, C3'=1s, C4'=0.66s, C5'=1.58s, (C): natural 2'-deoxyguanosine (dG), $T_1$: C1' (d 85.6)=0.61s, C2' (d 39.7)=0.4s, C3' (d 75.4)=0.62s, C4' (d 84.8)=0.62s, C5' (d 62.9)=0.31s, (D): Deuterated 2'-deoxyguanosine [dG*, where the 1'#, 2', 2", 3', 4'#, 5' and 5" protons have been exchanged with deuterium], $T_1$ C1'= 0.6s, C2'=1.3s, C3'=1.1s, C4'=0.6s, C5'=1.6s.

FIGS. 33(A) through 33(D): $T_1$ measurements by inversion recovery experiments ($^{13}$C-NMR) of natural and partially deuterated deoxynucleosides. (A): Natural 2'-deoxyadenosine [dA], $T_1$: C1' (d 87.1)=0.65s, C2' (d 37.6)=0.39s, C3' (d 75.8)=0.71s, C4' (d 87.1)=0.65s, C5' (d 62.8)=0.33s, (B): Deuterated 2'-deoxyadenosine [dA* where the 2', 2", 3', 5' and 5" protons have been exchanged with deuterium (>97% $^2$H). The 1'# is ~20% deuterated while the 4'# is ~85% deuterated], $T_1$ C1'=0.6s, C2'=1.76s, C3'=1.5s, C4'=0.6s, C5'=2.1s, (C): natural 2'-deoxycytidine [dC], $T_1$: C1' (d 87.3)=0.66s, C2' (d 38.7)=0.41s, C3' (d 74.8)=0.68s, C4' (d 85.9)=0.62s, C5' (d 61.6)=0.35s, (D): deuterated 2'-deoxycytidine [dC*, where the 1'#, 2', 2", 3', 4'#, 5' and 5" protons have been exchanged with deuterium], $T_1$ C1'= 0.61s, C2'=1.1s, C3'=1.2s, C4'=0.6s, C5'=2.53s.

Figure 34:
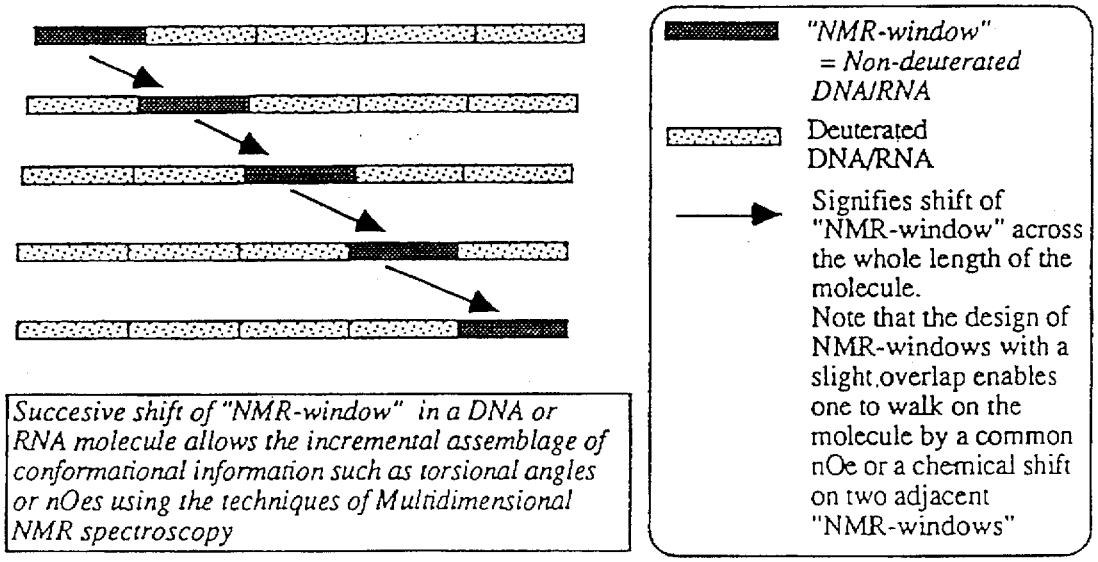

FIG. 34 shows the successive shift of an NMR-window in a DNA or RNA molecule.

Figure 35:
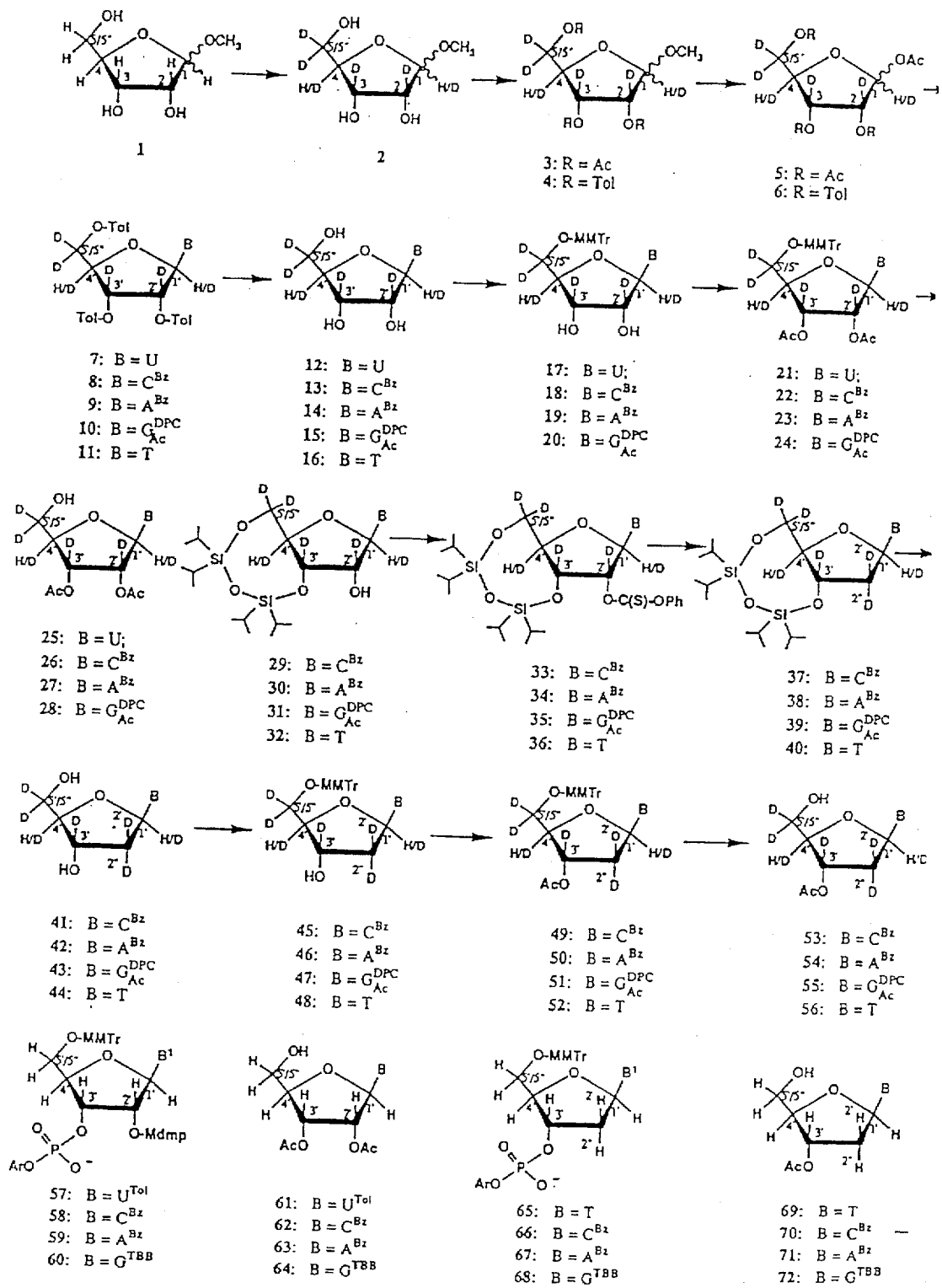

FIG. 35 shows deuterated nucleotides and nucleosides according to the present invention.

Figure 36:
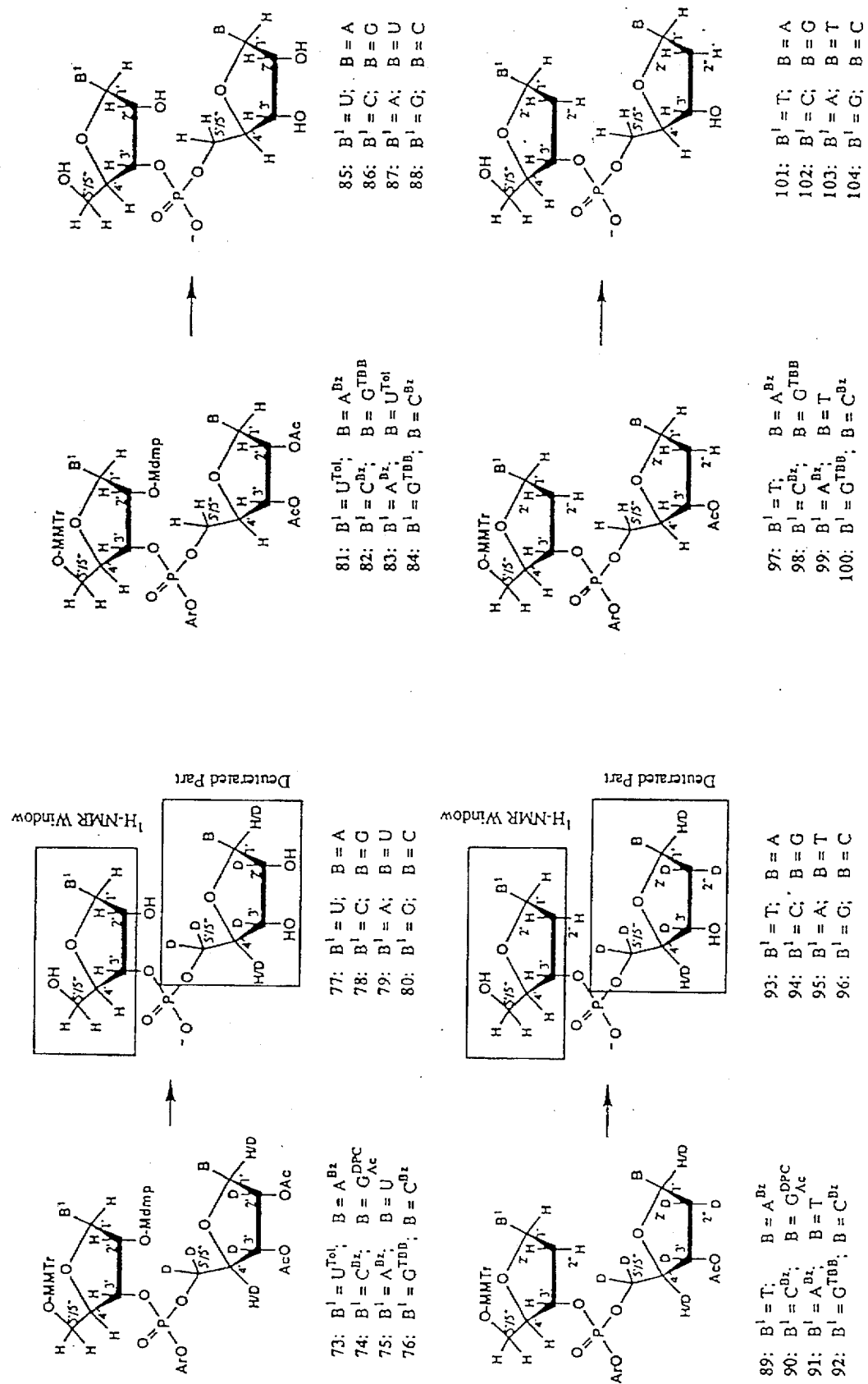

FIG. 36 shows the deuterated moieties and the NMR windows of nucleosides according to the present invention.

Figure 37:
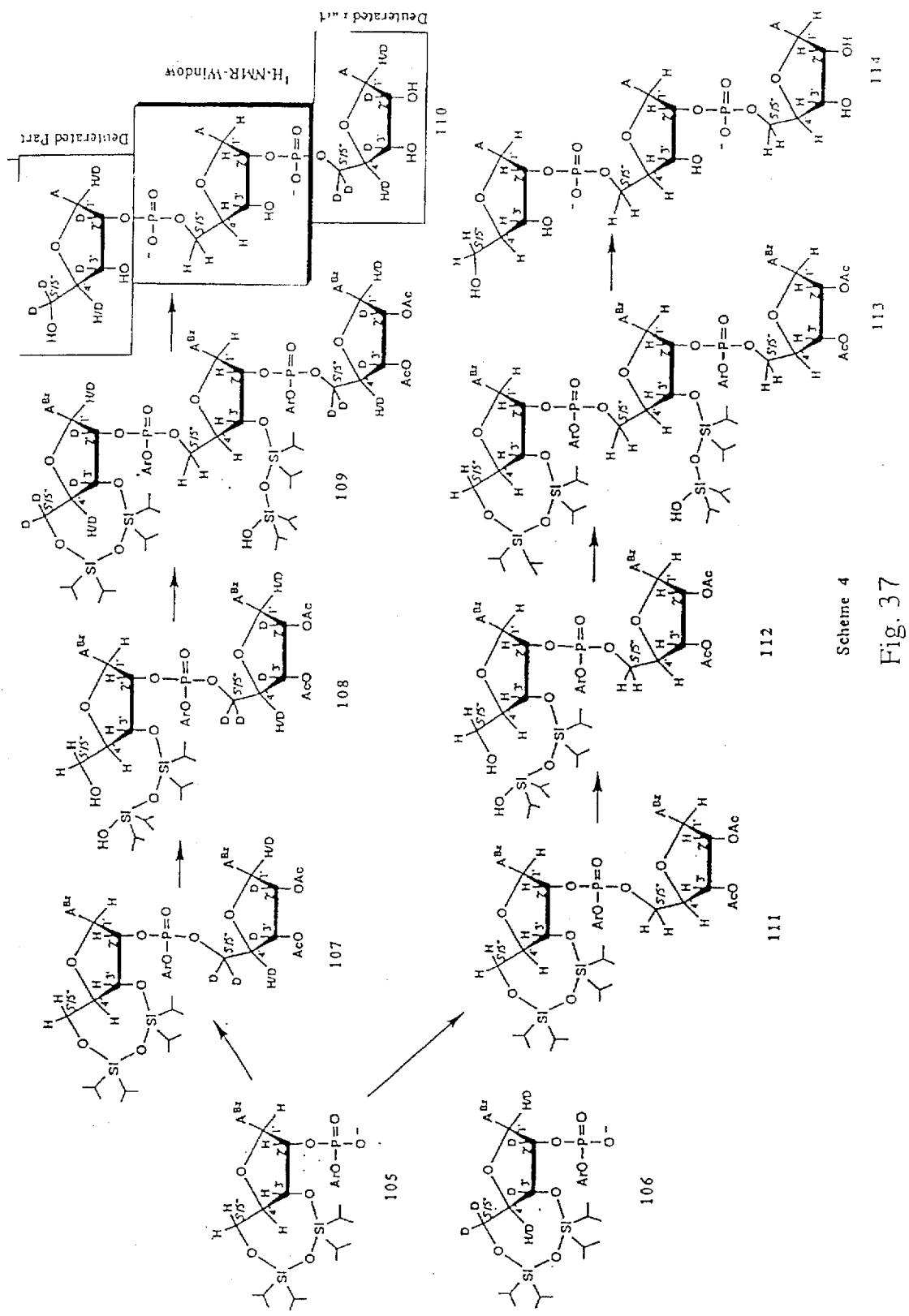

FIG. 37 shows the deuterated moieties and the NMR windows of nucleosides according to the present invention.

FIG. 38 illustrates preparation of the compounds according to the present invention.

The use of deuterium exchange for the spectral assignment of nucleosides and oligonucleotides is a well established technique[6,16,25,26i,j]. The deuteration of the nucleobase residue has been described (e.g. exchange of protons at C8-purine and C5-cytosine with deuterioammonium bisulfite at pD 7.8 in deoxyoligomers[6a] gave 90–95 atom % $^2$H incorporation, and platinum-catalyzed exchange at C5-methyl of thymidine in $^2$H$_2$O[6b] afforded 94 atom % $^2$H incorporation) and its effect on 1D and 2D $^1$H-NMR spectra was studied. In general, most attention has been however given to the possible simplification of the most crowded sugar part of the NMR spectra which holds important informations regarding the dynamics of both local and global conformation of the molecule. A large variety of enzymatic[20,25] and chemical methods[7–19,21–23,26–27] have been devised for deuterium incorporation at both sugar[8,15–22,26i–j,27] or nucleoside[7,9–14,25] levels which have the potential to provide monomeric building blocks deuterated at specific carbon center(s)[7–22,26i–j,27] or perdeuterated[25]. Enzyme promoted incorporation of deuterium has been found to be rather low (~90%)[20] and unsatisfactory for NMR work because of the stray resonances arising from the low level of deuteration[25,52] and cumbersome isolation of deuterated mononucleotide blocks. 5',5"-Adenosine was prepared from 2',3'-O-isopropylideneadenosine-5'-carboxylic acid[7]. Essentially, the same level of $^2$H enrichment was achieved starting from methyl-2,3-isopropylidene-β-D-ribofuranosiduronic acid[8]. The mixtures of diastereoisomers of 5'-deuterioadenosine[9] and 5'-deuteriothymidine (98 atom % $^2$H incorporation)[10] were obtained via the reduction of the appropriate 5'-aldehydes by sodium borodeuteride or lithium aluminium deuteride. The 5'-aldehyde derivative of 2'-deoxyguanosine was converted to 5' or 4'-deuterio-2'-deoxyguanosine[11] by heating the aldehyde in $^2$H$_2$O/pyridine mixture (1:1) followed by reduction of the aldehyde with NaBH$_4$. 4'-Deuterium labeled uridine and thymidine (98 atom % $^2$H) was obtained upon NaBD$_4$ addition to the protected 4',5'-unsaturated nucleoside followed by oxidation[12]. Deuterium was incorporated at C3' (97 atom % $^2$H) of adenosine at sugar level upon stereoselective reduction of 1,2:5,6-di-O-isopropylidene-α-D-hexofuranos-3-ulose to 1,2:5,6-di-O-isopropylidene-3-deuterio-α-D-ribohexofuranose[13] using sodium borodeuteride. Recently, more than 95 atom % $^2$H incorporation has been accomplished at C3' of adenosine with virtually complete stereoselecivity upon reduction of the 2'-O-tert-butyldimethylsilyl (TBDMS)-3'-ketonucleoside by sodium borodeuteride in acetic acid[14]. Specifically 2'-monodeuterated(R or S)-2'-deoxycytidines were synthesized[15] from specifically 2-monodeuterated-2-deoxy-D-riboses[16] obtained upon stereospecific reduction of a 2,3-dehydro-hexopyranose with lithium aluminium deuteride and oxidation of the resulting glycal. Syntheses of 2'-deoxy-2'(S)-deuterio-uridine and cytidine were carried out by the use of 1-methyl-2-deoxy-2(S)-deuterioribofuranoside[17]. 2-Deoxy-1-deuterio-D-erythro-pentose, 2-deoxy 2(S)-deuterio-D-erythro-pentose and 2-deoxy-1,2(S)-dideuterio-D-erythro-pentose were obtained from D-arabinose by a reaction sequence involving the formation and LiAlD$_4$ reduction of ketene dithioacetal derivatives[18]. Detailed method was published by us about the stereospecific synthesis of all eight 2' or 2"-deuterio-2'-deoxynucleosides by reductive opening of appropriate methyl 2,3-anhydro-α-D-ribo or β-D-lyxofuranosides with LiAlD$_4$[19]. 2',2"-Dideuterio-2'-deoxyguanosine and thymidine were prepared from 2-deoxyribose. 5-phosphate using 2-deoxyribose 5-phosphate aldolase enzyme in $^2$H$_2$O achieving some 90 atom % deuteration[20]. The synthesis of all 2',2"-dideuterio-2'-deoxynucleosides was achieved in this laboratory with deuterium incorporation at both nucleoside and sugar levels (oxidation of C2', subsequent reduction with NaBD$_4$ or LiAlD$_4$ followed by deoxygenation by tributyltin deuteride)[21]. Greater than 99 atom % $^2$H incorporation at C1 of 2'-deoxyribose has been reported[22] recently by reduction of 3,5-bis-O-TBDMS-2-deoxyribonolactone by Dibal-D. On the other hand, the same reaction performed on the 2,2'-dideuterated ribonolactone obtained upon base-catalyzed H/D exchange at C2 of 2-deoxy-ribonolactone (~95% and ~85% deuteration at 2 and 2'-position, respectively) gave 1,2,2'-trideuterio-2'-deoxyribose[22].

We envisioned at the outset that the preparation of a simple 2',3',5',5"-$^2$H$_4$-nucleoside with >97 atom % $^2$H incorporations should serve well for the purpose of creating $^1$H-NMR window because of the fact that it would have H1' vicinal to $^2$H-2', and H4' would be flanked by vicinal $^2$H-3',5',5" which should block the propogation of J relays in the 2D spin-spin correlated spectroscopy such as DQF-COSY or TOCSY experiments. This means that although H1' and H4' would be detectable in 1D $^1$H-NMR experiments but would be completely undetectable in 2D COSY, DQF-COSY or TOCSY experiments thus simplifying the spectra for assignment purposes allowing the extraction of coupling constants and nOe volume informations from the protonated part of the molecule. It was clear to us at this stage that the H4' of 2',3',5',5"-$^2$H$_4$-nucleotide would show a cross peak due to its coupling with the 5'-phosphorous in 1D $^1$H-NMR experiments but this will be indetectable because of the reasons said above.

Figure 1B:
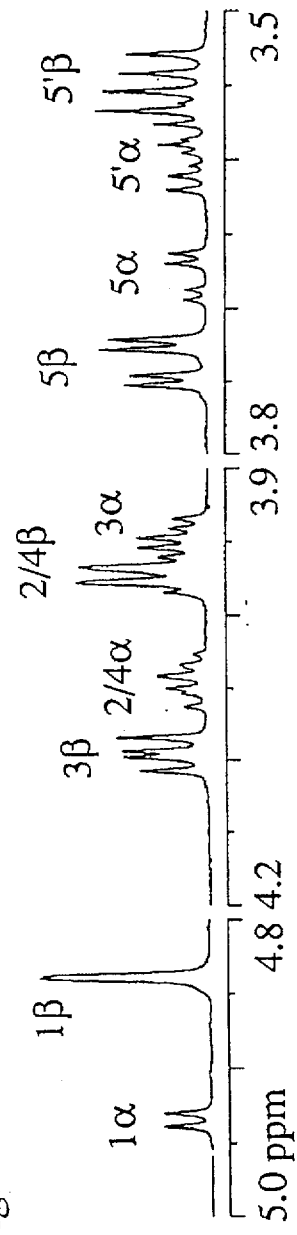
Figure 1C:
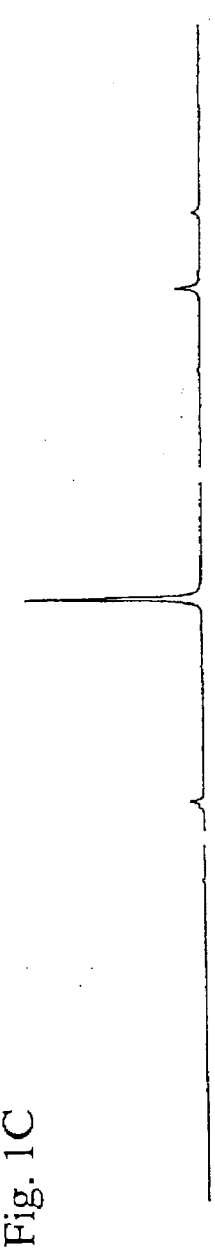
Figure 2A:
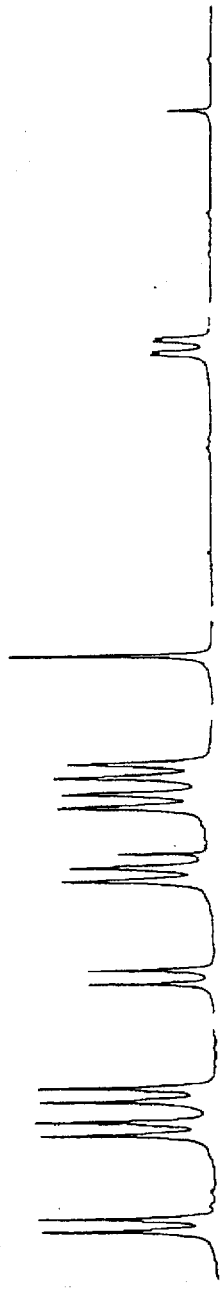
Figure 2B:
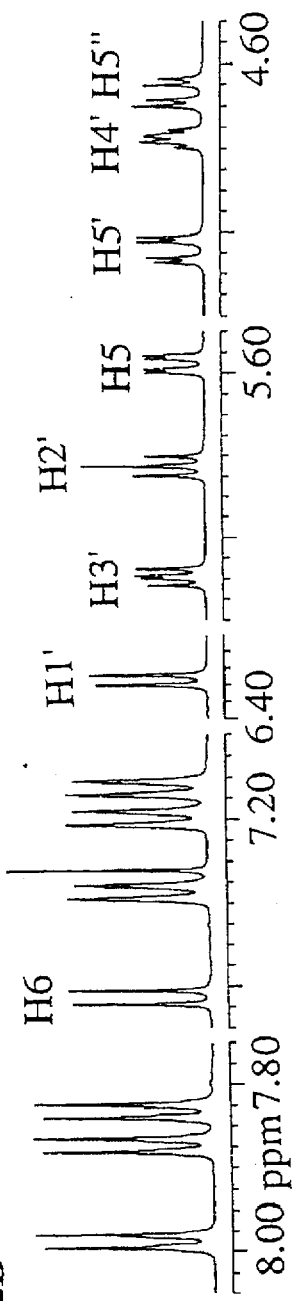
Figure 2C:
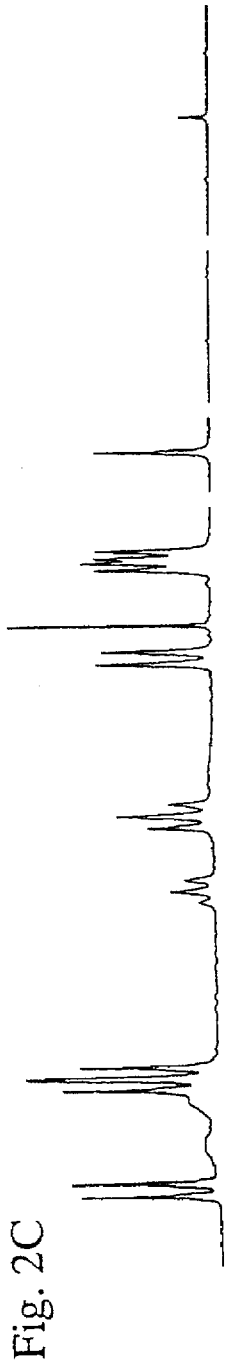
Figures 2D, 2E, 2F:
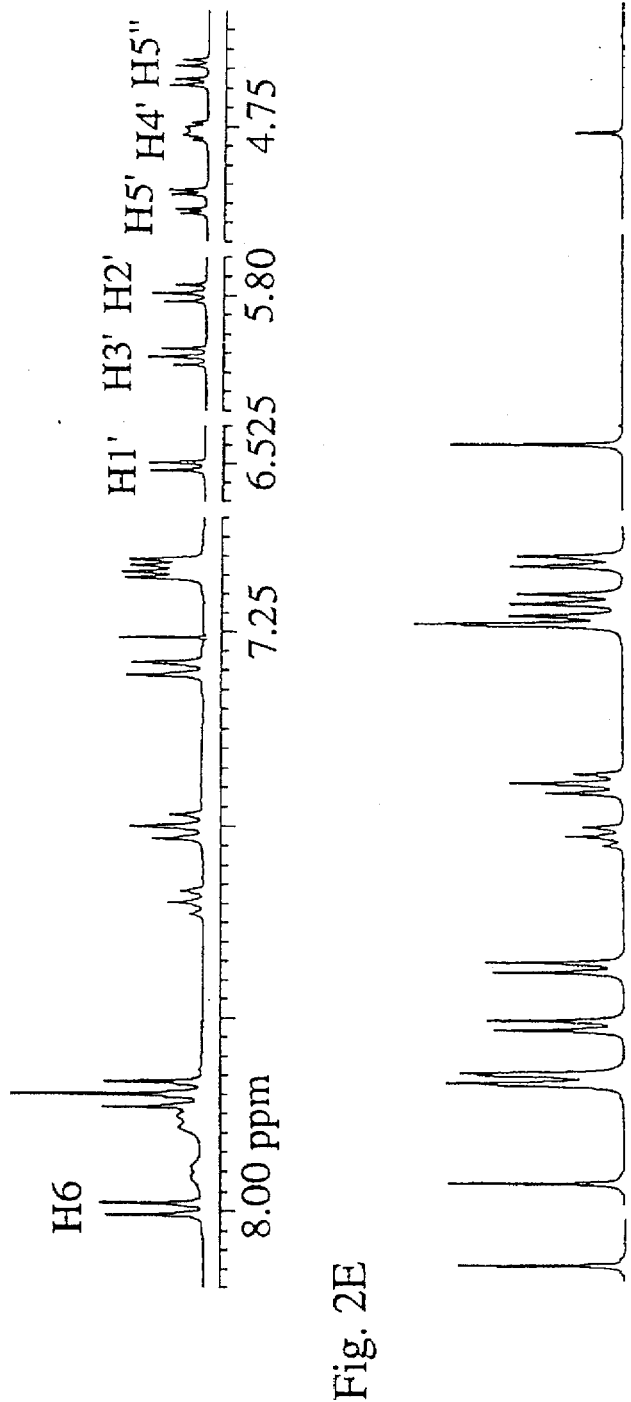
Figure 4A:
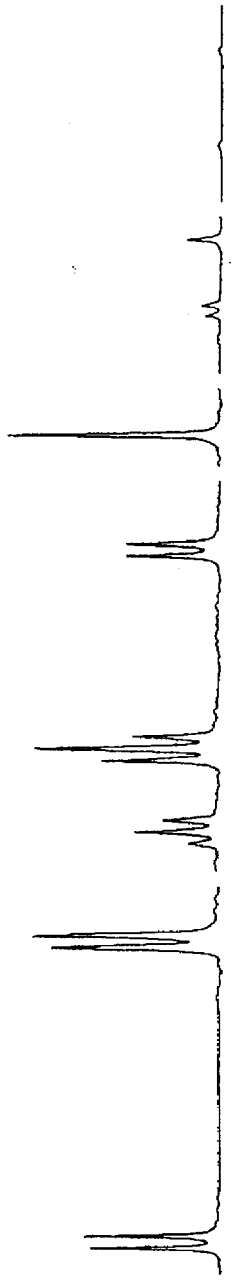
Figure 4B:
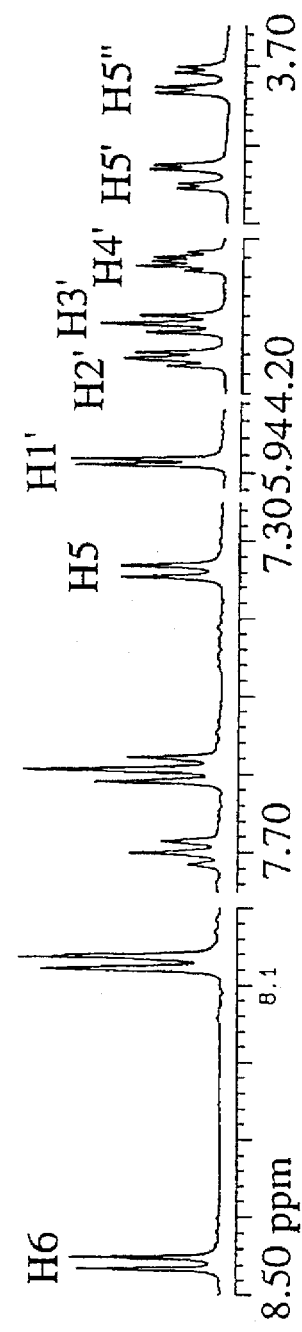
Figure 4C:
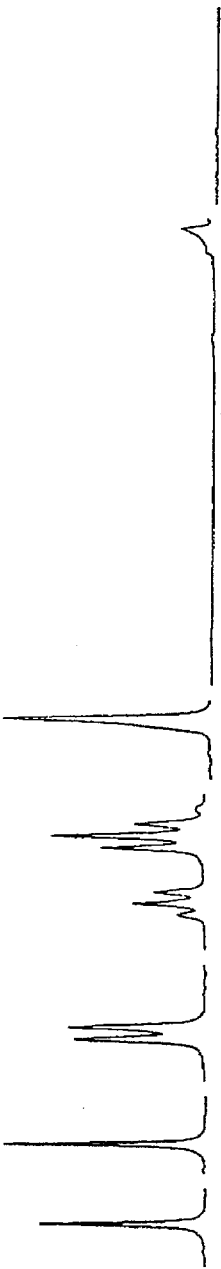
Figure 5A:
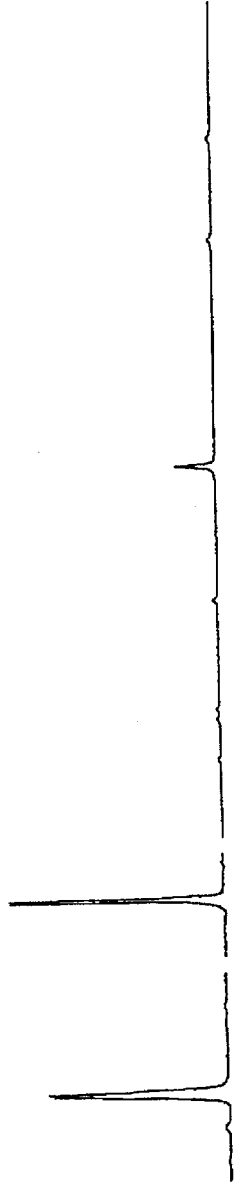
Figure 5B:
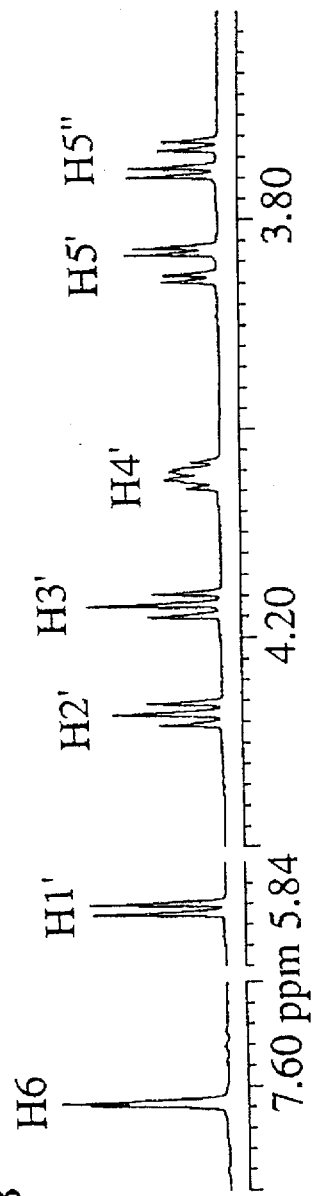
Figure 5C:
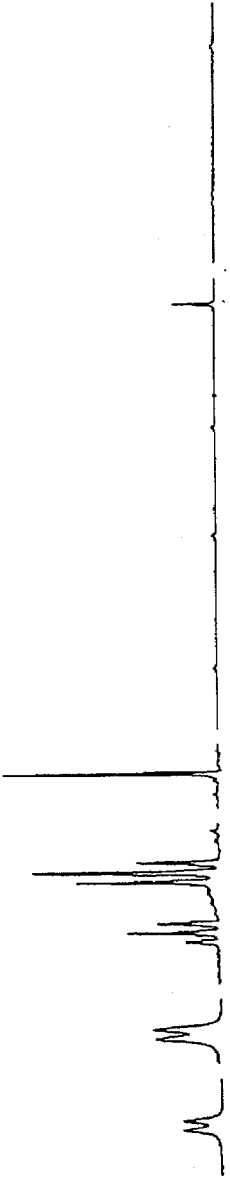
Figures 5D, 5E, 5F:
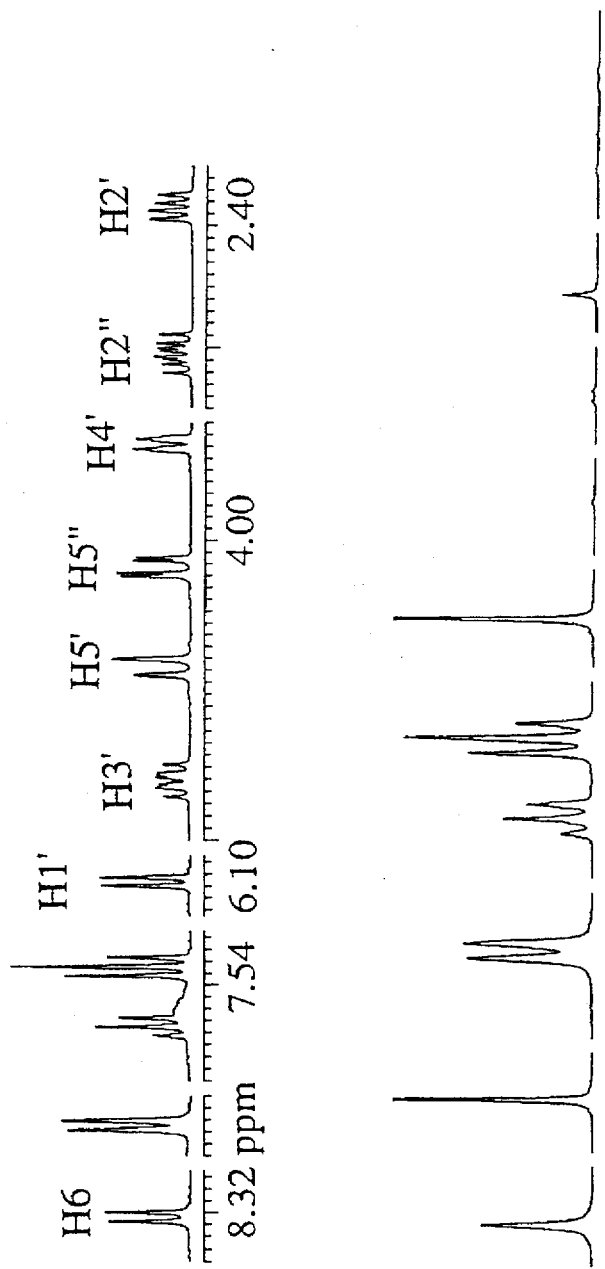
Figures 6D, 6E, 6F:
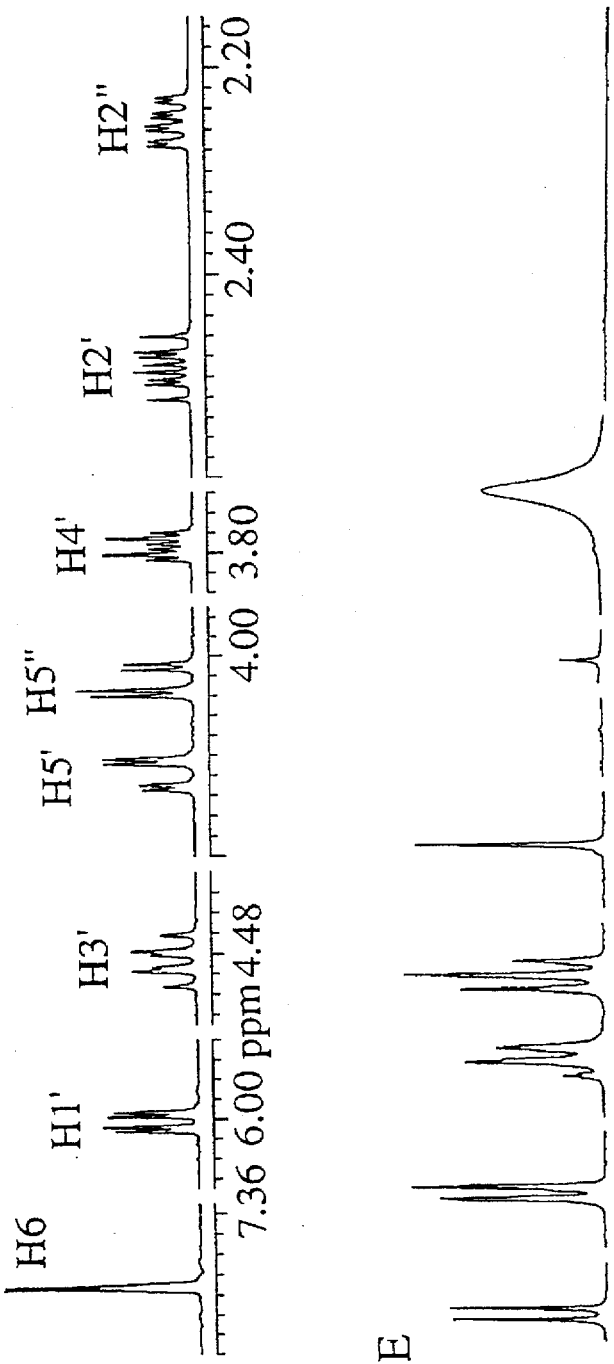
Figure 7A:
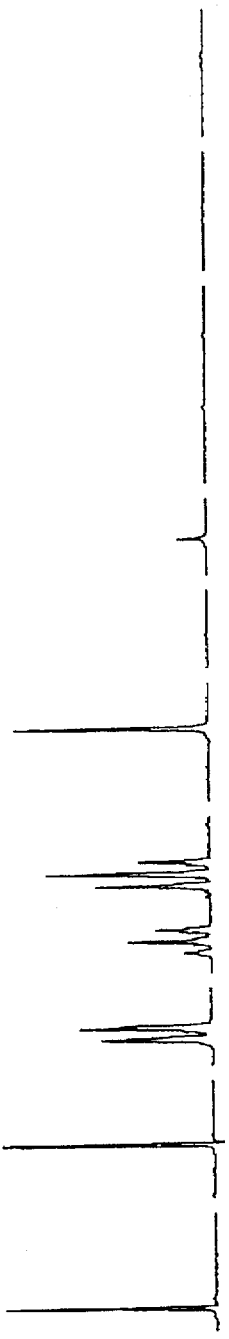
Figure 7B:
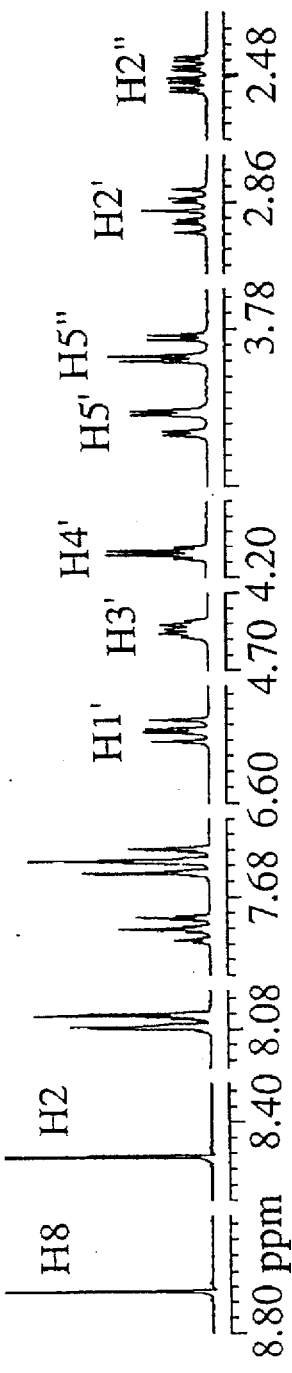
Figure 7C:
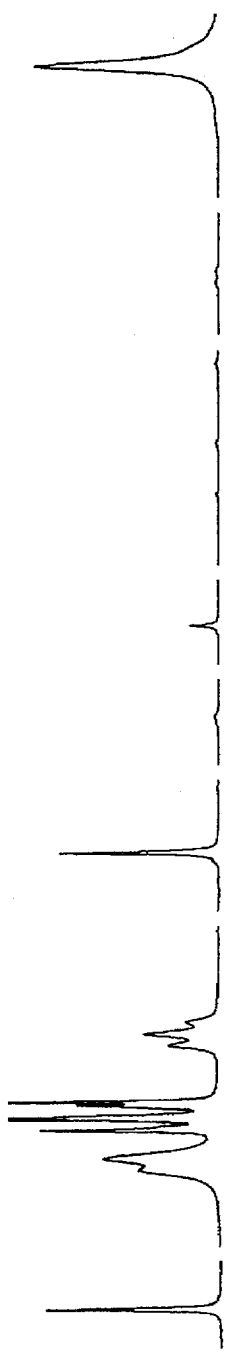
Figures 7D, 7E, 7F:
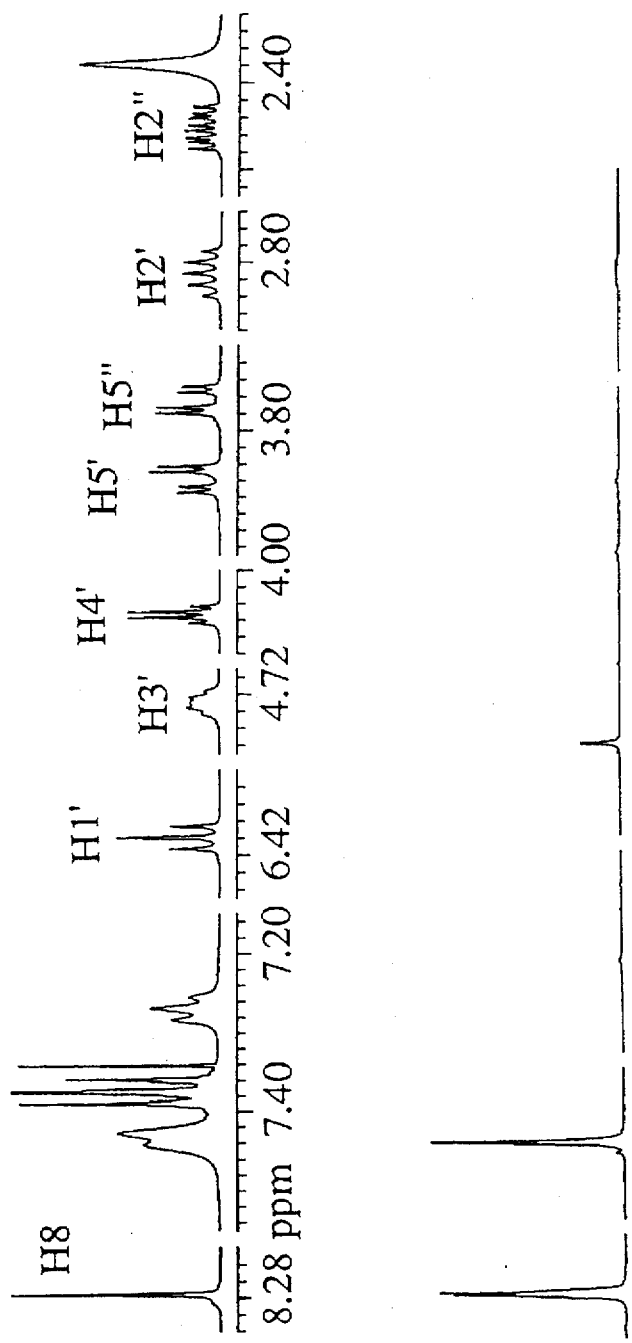
Figure 8B:
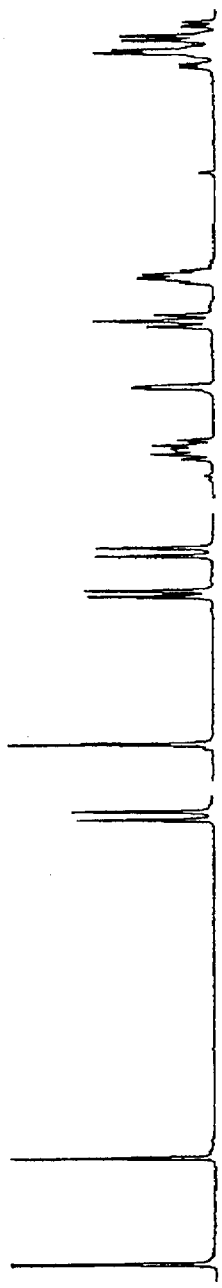
Figure 8A:
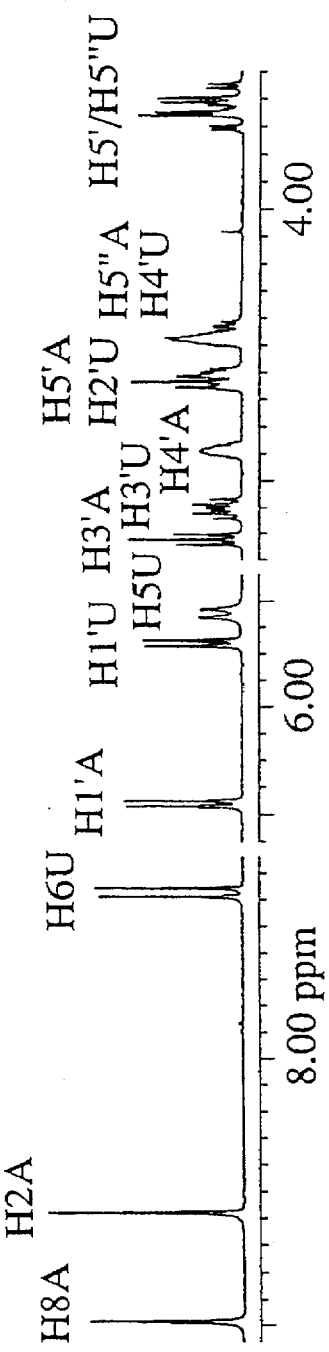
Figure 8D:
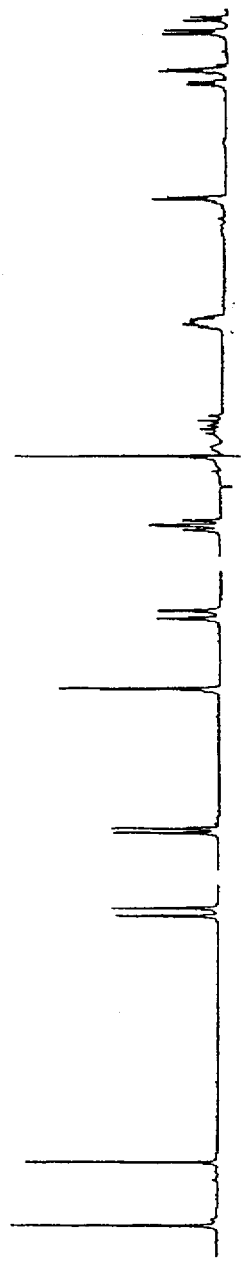
Figure 8C:
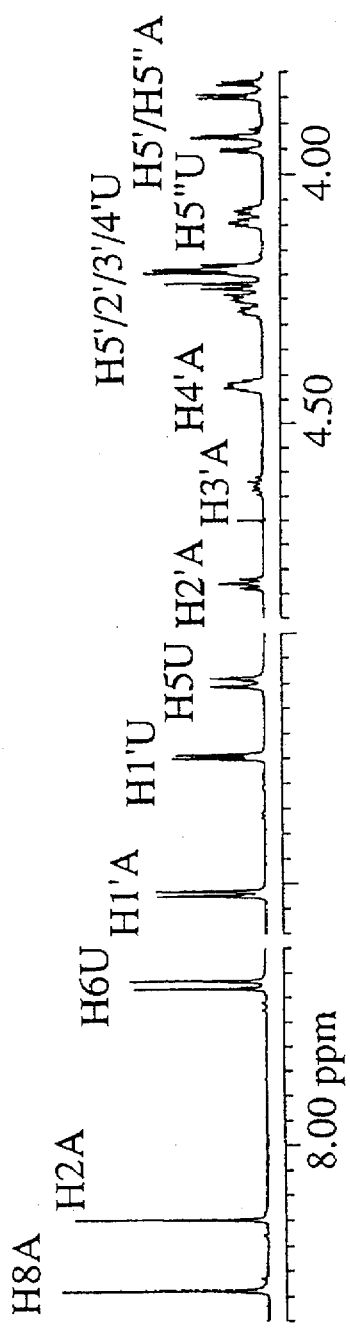
Figure 8F:
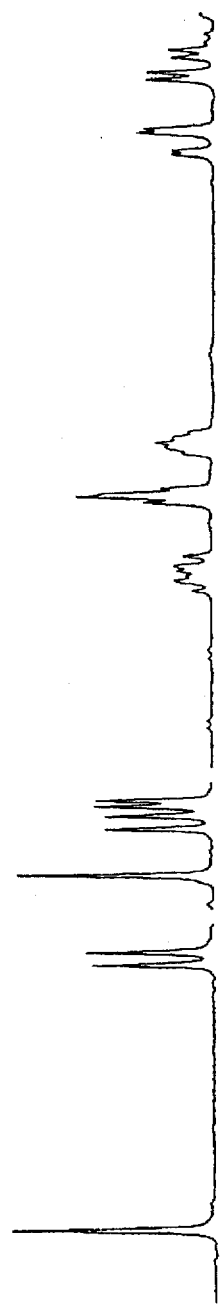
Figure 8E:
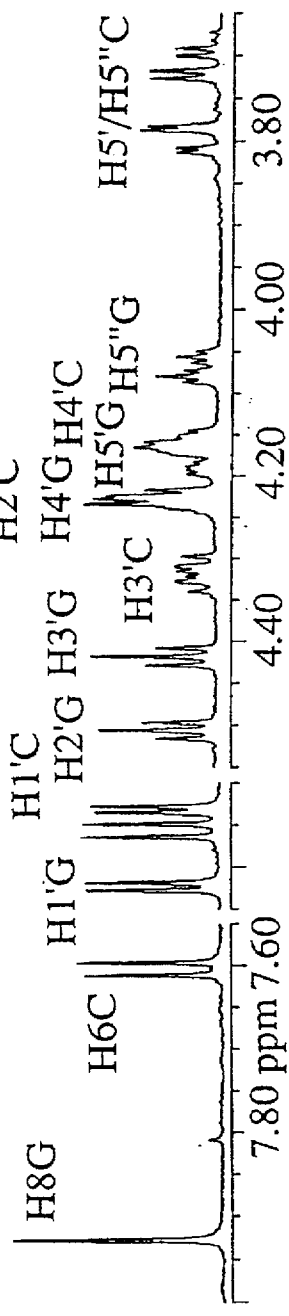
Figure 9B:
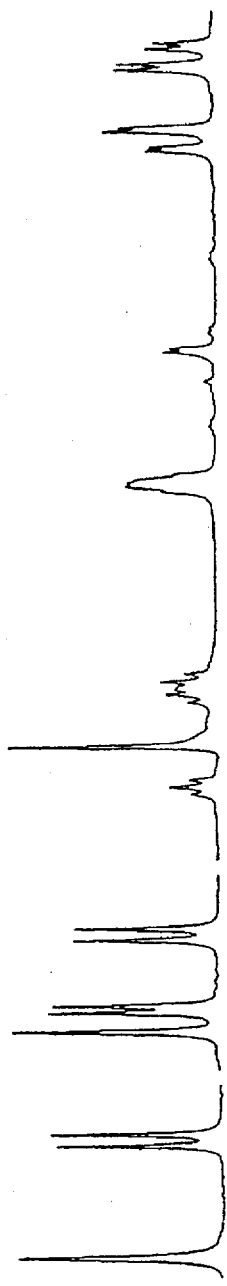
Figure 9A:
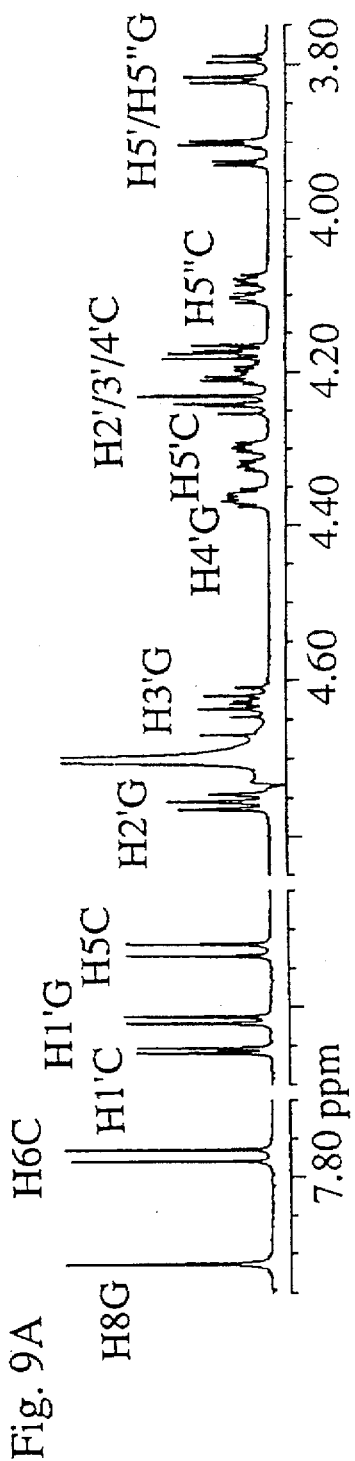
Figure 9D:
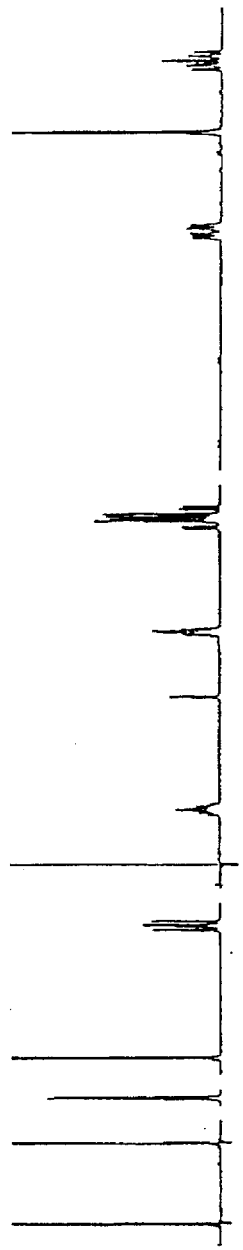
Figure 10B:
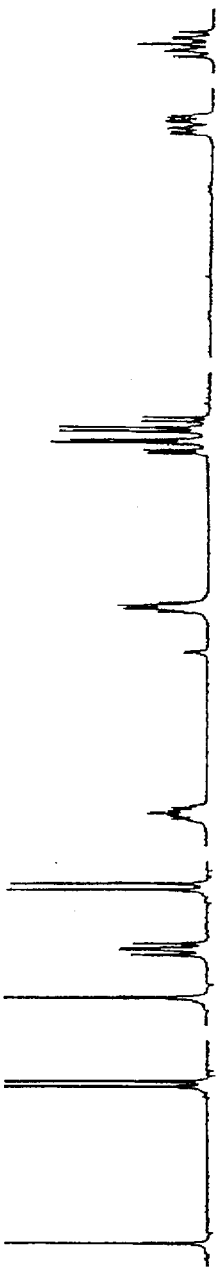
Figure 10A:
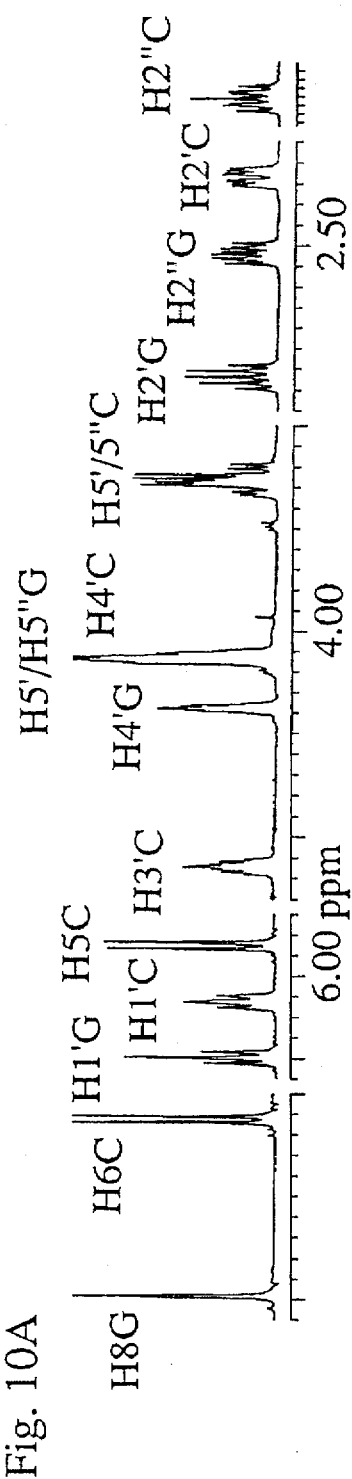
Figure 10D:
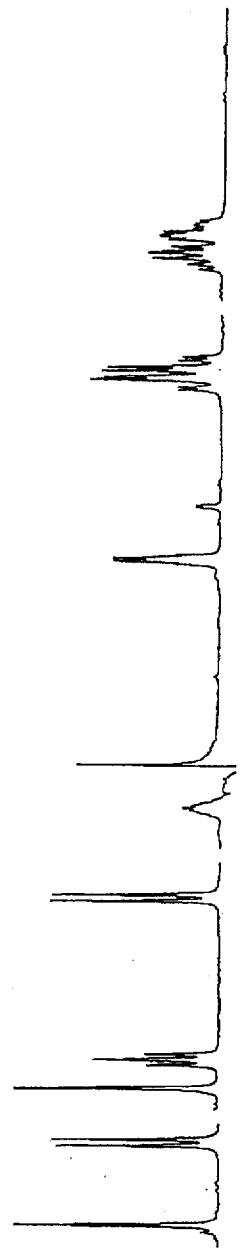

Since the glycosylation reaction of a nucleobase with the α/β mixture of sugar derivative 5 or 6 gives β-D-nucleoside in a stereospecific manner owing to the intermediacy of carboxonium ion formed by the 2'-O-acyl protecting group[31a], we decided to start our Raney nickel-$^2$H$_2$O exchange reaction on a crude mixture of methyl α/β-D-ribofuranoside (see FIG. 35). A mixture of methyl α/β-D-ribofuranoside (~3:10) 1 was obtained in 98% yield upon treatment of D-ribose with concentrated sulfuric acid in dry methanole[32] at ~4° C. for 24 h, followed by neutralization upon a passage through a column of Amberlist A-21 (OH⁻ form) ion exchange resin. This epimeric mixture of sugars 1, $^2H_2O$ and deuterated Raney nickel were heated under reflux with exclusion of atmospheric moisture (see experimenatal). The site specific exchange (rates C5>C3=>C2>>C4) competes with slower epimerization reactions at C2 and C3[27]. It has been shown that complete deuteration at C5 and 30–50% deuteration at C2 and C3 could be achieved within 6 h upon boiling a mixture of methyl a or β-D-ribofuranoside in $^2H_2O$ with deuterated Raney nickel. In the early stage of our work, the generally applied W-2 type Raney nickel[33] was used with moderate reaction time (3–4 days). In our experiments, however, we wished to drive the deuteration exchange reactions to as high deuterium atom content as possible for suppressing all stray resonances (monitored by 500 MHz $^1H$-NMR). An acceptable level of deuterium incorporation (>97 atom % $^2H$) even at the realatively slowly exchanged C2 required at least 4–7 days of boiling under reflux (see experimental) giving a higher level of deuterium exchange at the expense of lower yield (60–80%) of the desired methyl 1#,2,3,4#,5,5'-$^2H_6$-α/β-D-ribofuranoside 2 (>97 atom % $^2H$ at C2, C3, C5/5'; ~85 atom % $^2H$ at C4 (C4'#); ~20 atom % $^2H$ at C1(C1'#)). The $^1H$-NMR spectra of this crude sugar derivative 2 at 500 MHz revealed the presence of products due to side reactions[27d,g,h] (see anomeric region in Panel A in FIG. 1, Panel B shows natural-abundance methyl-(α/β: ~3/10)-D-ribofuranoside 1). Subsequent acetylation of this crude product 2 with acetic anhydride in dry pyridine resulted in 1-O-methyl-2,3,5-tri-O-acetyl-α/β-D-1#,2,3,4#,5,5'-$^2H_6$-ribofuranoside 3 in 82% yield, which was converted to 1,2,3,5-tetra-O-acetyl-α/β-D-1#,2,3,4#,5,5'-$^2H_6$-ribofuranoside 5 by a treatment with sulfuric acid in acetic acid-acetic anhydride for 12 h at room temperature (RT) (97%). Neither compound 3 or 5 was possible to purify by chromatographic means. Compound 5 was therefore coupled with silylated N-protected nucleobases[31] and purified chromatographically. The examination of $^1H$-NMR spectra of the chromatograpically pure reaction product revealed that the the required β-D-nucleoside was the major component (90–95%) which was contaminated with insepa-rable by-products. This impurity content slowly diminished during the run through the synthetic sequences and purification steps giving pure 5'-hydroxy blocks 25–28 and 53–56. Another striking finding was the highly variable level of deuterium exchange (~98% down to ~70%) depending upon the given batch of the deuterated Raney-Ni catalyst used in the isotope exchange reaction. This problem could partially be solved by repetition of the deuteration reaction one more time without any further loss of yield of 2 due to isomerization reactions. This is because of the fact that right at the first cycle of deuteration exchange for 4–7 days gave the thermodynamic mixture of epimers which did not alter in the second cycle of deuteration exchange. In the course of synthesis of RNA dimers it turned out, that 95–96% incorporation is sufficient for the suppression of cross peaks in DQF-COSY and TOCSY spectra. On the contrary, the same level of deuteration was not sufficient to suppress the cross peaks in the DNA dimers because of more effective J relays due to the larger J couplings through the 2'-deoxy protons. These findings clearly indicated the need for (i) a reliable deuterium exchange method to attain a consistent deuterium enrichment in the sugar in different batches, and (ii) since such deuterium exchange reaction will inherently produce epimeric xylo and arabino sugars as main by-products[27g], therefore the purification of the methyl α/β-D-1#,2,3,4#,5,5'-$^2H_6$-ribofuranoside 2 from the exchange reaction should be achieved. In the pursuit for a more active catalyst, we tried to use W-5 type Raney nickel[34], which is prepared at higher temperature (~55° C.) and with more extensive washings (see experimental). With these modifications and by the use of at least 20 ml $^2H_2O$/g of sugar, it was possible to achieve a reproducible >97 atom % deuterium incorporation at C2, C3 and C5 positions in 2. It was also noted that C1 and C4 could be consistently deuterium enriched by ~20 and ~85%, respectively. As it turns out from Table 1, the extent of exchange at C1 and C4 increases slowly depending on the length of reflux (~10 atom % $^2H$ at C1 and ~78 atom % $^2H$ at C4 after boiling at reflux for 4 days, and ~17 atom % $^2H$ at C1 and ~85 atom % $^2H$ at C4 after boiling at reflux for 7 days) whereas the deuteration levels at C2, C3 and C4 practically do not change. In order to obtain pure starting material for the coupling reactions with the N-protected nucleobases, we decided to apply 4-toluoyl protection for the hydroxyls, which made the UV detection possible facilitating the separation procedure. The toluoylation was carried out in dry pyridine (5 ml/mmol sugar) at RT overnight[35] to give after a careful separation on a column of silica gel the desired practically pure 1-O-methyl-2,3,5-tri-O-(4-toluoyl)-α/β-D-1#,2,3,4#,5,5'-$^2H_6$-ribofuranoside 4 in 48% yield (Panel C in FIG. 1, Panel D shows natural-abundance counterpart). The conversion of C1 to O-acetyl provided a second opportuinity for purification. The reaction, performed in acetic acid-acetic anhydride mixture by adding sulfuric acid, gave the 1-O-acetyl-2,3,5-tri-O-toluoyl-α/β-D-1#,2,3,4#,5,5'-$^2H_6$-ribofuranoside 6 (Spectrum E in FIG. 1, Panel F shows natural-abundance counterpart) in a substantially higher yield (82%) after purification than the previous one, indicating that the most important separation was really achieved after the toluoylation reaction.

Compound 6 was condensed with silylated uracil, $N^4$-benzoylcytosine[36], $N^6$-benzoyladenine[36] $N^2$-acetyl-$O^6$-diphenylcarbamoylguanine[37] and thymine using trimethylsilyl trifluoromethanesulfonate as Lewis acid catalyst[31b,37] to prepare the corresponding 1'#,2',3',4'#,5',5"-$^2H_6$-β-D-ribonucleoside derivatives 7, 8, 9, 10, 11 in 75, 85, 60, 73 and 91% yields, respectively. The isomeric purities of these products are found to be excellent as evident through their 500 MHz $^1H$-NMR spectra (FIG. 2: (A)–(E); FIG. 3: (A)–(D)). For further work the OH protecting groups were removed in the following manner: the fully protected nucleosides were dissolved in pyridine-ethanol (2:3 ml/mmol) followed by addition of ethanolic NaOH (6.4 ml of ethanol and 6.4 ml of 2N NaOH/mmol)[39], and stirred for 5 min. This gave the crude deuterated nucleosides 12, 13, 14, 15 and 16 in 99, 98, 105, 79 and 99% yields, respectively, after neutralization by Dowex cation exchange resin (H⁺ form). 500 MHz $^1H$-NMR spectra of purified deuterated nucleosides 12, 13, 14, 15 and 16 (80–90%) are shown in FIGS. 3–5 (FIG. 3: (E)–(G); FIG. 4: (A)–(F); FIG. 5: (A)–(B). Crude 12–15 were treated with 4-methoxytriphenylmethyl (MMTr) chloride in dry pyridine overnight to give the 5'-O-MMTr-1'#,2',3',4#',5',5"-$^2H_6$-nucleosides 17, 18, 19 and 20 in 53, 78, 72 and 78% yields, respectively. These derivatives were acetylated by acetic anhydride treatment in dry pyridine to afford the 5'-O-MMTr-2',3'-di-O-acetyl-1'#,2',3',4'#,5',5"-$^2H_6$-nucleosides 21, 22, 23 and 24 in 85, 97, 92 and 78% yields, respectively. After removal of the 5'-O-MMTr group by a treatment with 80% aqueous acetic acid at RT overnight, the 5'-hydroxy blocks 25, 26, 27 and 28 were obtained in 95, 81, 94 and 58% yields, respectively, which were used for dimer syntheses.

For the conversion of our deuterated ribonucleosides 13–16 to the corresponding 2'-deoxynucleosides 41–44, the convenient route devised by Robins et al. was chosen[30,21,28]. Treatment of compounds 13–16 with 1,3-dichloro-1,1,3,3-tetraisopropyldisiloxane[40] in dry pyridine resulted in 3',5'-O-(1,1,3,3-tetraisopropyldisiloxane-1,3-diyl(TPDS))-1'#,2', 3', 4'#,5',5"-$^2H_6$-nucleosides 29, 30, 31 and 32 in 85, 77, 83 and 66% yields, respectively. Treatment of these derivatives in dry dichloromethane using 1-methylimidazole as catalyst gave the corresponding 2'-phenoxythiocarbonate derivatives 33, 34, 35 and 36 in 87, 88, 89 and 89% yields, respectively. 2'-Deoxygenation of these compounds by tributyltin deuteride in precence of azoisobutyronitrile (AIBN) in dry toluene at 75° C. proceeded without any problem to give compounds 37, 39 and 40 in 75, 96 and 95% yields respectively, except for the adenosine derivative 34, in which case simultaneous partial loss of benzoyl group had occured as it was revealed by the $^1$H-NMR spectra. The re-benzoylation of the 3',5'-O-TPDS-1'#,2',2",3',4'#,5',5"-$^2H_7$-2'-deoxyadenosine was done easily to give an additional crop of the desired derivative increasing the original 77% yield to 92%. The deuterium incorporation at the 2" was >97.5% as evidenced by integration of $^1$H-NMR spectra of the residual proton resonance, which is consistent with the isotope content of LiAlD$_4$ (98 atom % $^2$H) used in the reduction of tributyltin chloride[41] to tributyltin deuteride which was used as the reagent. After removal of TPDS protection by a treatment with tetrabutylammonium fluoride in dry tetrahydrofuran, the 1'#,2',2",3',4'#,5',5"-$^2H_7$-2'-deoxynucleosides 41, 42, 43 and 44 were obtained in 88, 93, 80 and 83% yields, respectively. These compounds were further transformed to the 5'-O-MMTr derivatives 45, 46, 47 and 48 (87, 90, 84 and 88%, respectively), followed by acetylation of the 3'-hydroxyls as documented above for the ribo compounds to afford the fully protected heptatadeuterio nucleosides 53, 54, 55 and 56 in 89, 77, 94 and 83% yields, respectively, except for the fact, that acetylation of 2'-deoxyadenosine derivative 46 was carried out at 4° C. with 1.3 equiv acetic anhydride[42]. Removal of 5'-O-MMTr group was achieved by a short treatment with 2% benzenesulfonic acid in dichloromethane-methanol (7:3, v/v) mixture to give the 5'-hydroxy blocks 53, 54, 55 and 56 in 86, 90, 78 and 69% yields, respectively.

Preparation of Partially Deuterated Dinucleotides & Trinucleotide. In order to investigate the effect of deuteration on 1D and 2D $^1$H-NMR such as DQF-COSY, HOHAHA and NOESY, two sets of dimers were synthesized using phosphotriester chemistry[43]. The 5'-OH group of 1'#,2',3',4'#,5',5"-$^2H_6$-ribonucleoside blocks 25, 26, 27 and 28 as well as the nondeuterated 61, 62, 63 and 64 were coupled to the triethylammonium salt of 2'-O-(3-methoxy-1,5-dicarbomethoxypentane-3-yl (MDMP))-5'-O-MMTr-ribonucleoside 3'-(2-chlorophenyl)-phosphates[43–46] 57, 58, 59 and 60 according to the reaction schemes 2 & 3 in dry pyridine in the presence of 1-mesitylenesulfonyl-3-nitro-1, 2,4-triazole (MS-NT)[45] to give the fully protected partially-deuterated dimers UpA* (* denotes for deuterated nucleoside moiety) 73 (72%), CpG* 74 (95%), ApU* 75 (7.9%), GpC* 76 (40%), and their natural counterparts UpA 81 (91%), CpG 82 (84%), ApU 83 (65%) and GpC 84 (84%) after saturated sodium hydrogen carbonate work-up and column chromatography. The deprotection of the dimers above was carried out using a well established literature procedure[44a,46] and subsequent purification on Sephadex A-25 culumn using a linear gradient of ammonium bicarbonate to obtain the deprotected partially deuterated dimers UpA* 77 (53%), CpG* 78 (49%), ApU* 79 (77%), GpC* 80 (49%), and their nondeuterated natural counterparts UpA 85 (76%), CpG 86 (76%), ApU 87 (56%) and GpC 88 (85%), which were lyophylised from $^2$H$_2$O before they were subjected to NMR studies. The 5'-OH group of 1'#,2',2",3',4'#, 5',5"-$^2H_7$-2'-deoxyribonucleoside blocks 53–56 and the non-deuterated 69–72 were coupled with the 3'-phosphotriester blocks 65–68 as described above[43–46] to give the fully protected partially deuterated 2'-deoxy dimers d(TpA*) 89 (86%), d(CpG*) 90 (75%), d(ApT*) 91 (77%), d(GpC*) 92 (80%), and their natural counterparts d(TpA) 97 (86%), d(CpG) 98 (83%), d(ApT) 99 (90%) and d(GpC) 100 (89%). Subsequently, the deprotected partially deuterated 2'-deoxiribonucleotide dimers d(TpA*) 93 (62%), d(CpG*) 94 (92%), d(ApT*) 95 (78%), d(GpC*) 96 (80%), and their natural counterparts d(TpA) 101 (80%), d(CpG) 102 (90%), d(ApT) 103 (89%) and d(GpC) 104 (71%) were obtained after deprotection and purification procedures reported for the ribo dimers[43–46].

In order to further evaluate the actual NMR simplification that has taken place in the $^1$H-NMR window part as a result of specific deuterium incorporation we decided to prepare the shortest oligomer which can hold a nondeuterated unit ($^1$H-NMR window) flanked by deuterated units, i.e. a trinucleotide. An obvious choice was the 2–5A core (A2'p5'A2'p5'A) and its partially deuterated counterpart (A*2'p5'A2'p5'A*) because it mimics the antiviral properties of interferon[47], and the detailed structural studies of the 2–5A core have been performed by $^1$H-NMR spectroscopy[48]. In the present synthesis of A2'p5'A2'p5'A 114 and its partially deuterated counterpart A*2'p5'A2'p5'A* 110, we have employed the same strategy which was devised earlier[49] in this laboratory, and based on the use of simultaneous 5' & 3' protection by the 1,3-dichloro-1,1,3,3-tetraisopropyl-disiloxane[49b] (Scheme 4).

These eight partially deuterated dinucleotides and trinucleotides were subsequently compared with the corresponding natural counterparts to evaluate the actual NMR simplifications achieved in the $^1$H-NMR window part as a result of specific deuterium incorporation (FIGS. 8A–33D).

In order to completely eliminate the cross peaks which arise in 2D NOESY experiments as a consequence of the interaction of protons of the nucleobases and H1' of sugar moieties of an oligomeric DNA or RNA, synthetic routes (Scheme 5) were devised for the chemical perdeuteration of the methyl α/β-D-ribofuranoside[55–59]. Isopropylidenation of the commercially available ribitol 115 in dry acetone with 2,2-dimethoxypropane in the presence of p-toluenesulfonic acid[55] gave 1,2:3,4-di-O-isopropylidene-ribitol 116. After catalytic hydrogene/deuterium exchange with W-5 deuterated Raney nickel-D$_2$O of the C5 hydrogens, the primary alcohol was oxydised to aldehyde using dicyclohexyl-carbodiimide (DCC) in dry DMSO[56] to give 2,3:4,5-di-O-isopropylidene-D-ribose-1-$^2$H$_1$ 118 with >97 atom % $^2$H incorporation at C1. Removal of isopropylidene protection was achieved upon a treatment with 80% aqueous acetic acid, followed by the conversion of the free D-ribose-1-$^2$H$_1$ 119 to anomeric mixture of methyl α/β-D-ribopyranoside-1-$^2$H$_1$ 120 by an identical treatment as described for compound 1, but boiling at reflux[57] for 12 h, to obtain the thermodynamically more stable six membered pyranose derivatives. Treatment of this mixture with deuterated Raney nickel in the usual way provided methyl α/β-D-ribopyranoside-1,2,3,4-$^2$H$_4$ 121 analogously to methyl α/β-D-arabinopyranoside reported by us[28]. Compound 121 was converted to methyl α/β-D-ribofuranoside-1,2,3,4-$^2$H$_4$ 123 by hydrolysis of the pyranoside with diluted hydrochloric acid[28] followed by glycosylation in dry methanol at 4 C. The 5' hydrogens were exchanged to deuterium upon a final Raney-nickel treatment to give after purification the α/β-D-ribofuranoside-1,2,3,4,5,5'-$^2$H$_6$ 124 with >97 atom % deuterium incorporation at C1, C2, C3, C4 and C5. The deuteration of C1 was also accomplished by the reduction of the ribonolactone 125 with sodium amalgam in $^2$H$_2$O giving the D-ribose-1-$^2$H$_1$ 119 in one step[58] which was subsequently converted to α/β-D-ribofuranoside-1,2,3,4,5,5'-$^2$H$_6$ 124. Compound 124 was converted to β-D-ribonucleosides-1',2',3',4',5',5"-$^2$H$_6$ 126–130 using a procedure described for 12–16. These β-D-ribonucleosides-1',2',3',4',5',5"-$^2$H$_6$ 127–130 were subsequently converted to 2'-deoxy-β-D-ribonucleosides-1',2',3',4',5',5"-$^2$H$_6$ 131–134 using an identical procedure described for 41–44.

Experimental Section

Materials and Methods. $^1$H-NMR spectra were recorded with a Jeol FX 90 Q and Bruker AMX 500 spectrometer at 90 and 500 MHz, respectively, using TMS (0.0 ppm) or acetonitrile peak for $^2$H$_2$O solutions (set at δ=2.0 ppm) as the internal standards. $^{13}$C-NMR spectra were taken with a Jeol FX 90 Q maschine at 27.7 MHz with TMS as internal reference for solutions other than $^2$H$_2$O in case of which CH$_3$CN (set at δ=1.3 ppm) was used as internal reference. $^{31}$P-NMR spectra were recorded at 36 MHz and 202 MHz in the same solvent as for $^1$H-NMR spectra using 85% phosphoric acid (0.0 ppm) or cAMP (−2.1 ppm) as external standard. Chemical shifts are reported in ppm (d scale). The two-dimensional NMR experiments were performed on a BRUKER AMX-500 MHz spectrometer. The DQF-COSY and Hartmann-Hahn spectra were recorded in pure-phase absorption mode with the time proportional incrementation method (TPPI) and with low power preirradiation of the residual HDO peak during the relaxation delay. The DQF-COSY[52] spectra were acquired with 4096 complex data points in t$_2$ and 256 points in t$_1$. The data were zero filled to give a 4096×1024 point matrix and a sine-square bell window was applied in both directions before Fourier transformation. The Hartmann-Hahn[53] spectra were acquired with 2048 complex data points in t$_2$ and 256 points in t$_1$. The data were zero filled to give a 2048×1024 point matrix and a sine-square bell window was applied in both directions before Fourier transformation. The $^1$H-$^{31}$P chemical shift correlation experiment[54] was performed in the absolute magnitude mode. A 1024×128 matrix data set was zero filled to 1024×512 data points a sine-square bell multiplication was applied in both directions before Fourier transformation. The $^{13}$C NMR INEPT experiments with and without proton decoupling and the $^{13}$C NMR inversion recovery experiments were performed on a JEOL GX 270 MHz spectrometer operating at 67.8 MHz for carbon. IR absorption spectra were recorded with a Perkin-Elmer 298 spectrometer.

The "usual work-up" refers to pouring the reaction mixture into saturated aqueous sodium hydrogen carbonate solution which was extracted with dichloromethane (3×~70 ml), pooled organic phases were dried over MgSO$_4$, filtered and evaporated.

Tri-n-butyltin deuteride was prepared via a modified literature method[41]. $^{13}$C-NMR (neat): 30.20 C-b (taken as reference[50]); 27.38 C-g; 13.79 C-d; 8.15 C-a. IR (neat): n$_{Sn-D}$=1298 cm$^{-1}$ (litr.[51]: n$_{Sn-D}$=1300 cm$^{-1}$).

Methyl α/β-D-ribofuranoside (1) was prepared according to a modified literature method[32] on a scale of 8 g. The reaction mixture was neutralized by passage through a bed of Amberlyst A-21 (OH$^-$ form) (300 g) resin pre-washed with distilled methanol to give the crude mixture of title compound 1 [α/β=~3:10] as a thick syrup. Yield: 8.57 g (98%). $^1$H-NMR (D$_2$O): 4.92 (d, J$_{1,2}$=3.2 Hz, 1H) H-1 (α-anomer); 4.83 (s, 1H) H-1 (β-anomer), 4.04-3.28 (m, 5H) H-2, H-3, H-4 & H-5 (a+b-anomer), 3.36 (s, 3H) OMe (α-anomer) 3.33 (s, 3H) OMe (β-anomer). $^{13}$C-NMR (α-anomer): 103.5 (C-1); 84.9 (C-4); 71.5 (C-2); 70.0 (C-3); 61.9 (C-5); 55.8 (OCH$_3$): (β-anomer) 108.3 (C-1); 83.2 (C-4); 74.6 (C-2); 71.2 (C-3); 63.2 (C-5); 55.5 (OCH$_3$).

Preparation of the Raney-nickel catalyst. A one-liter Erlenmeyer flask containing a five-centimeter long teflon-coated magnet, was placed in a plastic beaker on top of a magnetic stirrer. A thermometer (up to 100° C.) was fixed along the inner wall of the flask. The flask was filled with deionized-water (192 ml) and when slowly stirring NaOH-pellets (51.2 g) were added in one portion. After all pellets had dissolved, some ice-water was filled into the plastic beaker letting the temperature decrease to 50° C. Addition Ni-Al-alloy was started keeping the temperature at 50°±4° C. The total amount of Ni-Al-alloy (40.0 g) should be added within approximately 30 min. starting with small portions and ending with up to 1 ml per portion. The temperature is adjusted by the cooling-rate and by the addition speed. After completion of the addition, the flask was heated in an oil-bath at 50° C. for approximately 60 min. The flask was left for one hour to cool down to room temperature. Deionized-water (3×1l) was added and decanted. The particles were transferred to a 250 ml filtering flask with hose connection. A 20-cm long PVC-tube was connected on the hose of the flask. The flask was placed on a magnetic stirrer and the tube ended freely over a one liter beaker (for safety if too many particles are washed out). While stirring slowly, water (totally 4 l) was added slowly through the funnel, while liquid containing very small particles went into the beaker, and the flask could be left overnight, for continued washing the next day. Washing was continued for a whole day (using totally 20 l of water, during the last 10 l, a funnel was put into the filtering flask).In the beginning stirring was used between the washings while in the end stirring was used continously. After the washing the pH was checked in the following manner: most of the liquid was decanted from the flask, the particles were standing in a small volume of water for 10 min, then the pH of the remaining water in the flask was measured. If the pH was 6.5–7.0 and the liquid was almost clear, then the deuteration of the catalyst could be started.

Preparation of the deuterated Raney-nickel catalyst. The catalyst particles were transferred to a 50 ml serum bottle containing a two-centimeter long teflon-coated magnet. The bottle was sealed using a rubber stopper and the suspension was stirred for one minute, then after settling of the particles, water was removed with a pasteurpipette. After repeating this procedure a few times, deuteriumoxide (approximately 1.5 ml) was added, the bottle was flushed with nitrogen whereafter it was stoppered and sealed with parafilm. Stirring was maintained for 30 min ("1st wash"). The liquid was removed as before, $^2$H$_2$O was added (same amount), the bottle was flushed again with nitrogen, sealed with parafilm and stirred for half an hour. (At this stage the bottle could be left without stirring overnight, "2nd wash"). This washing procedure was repeated a few times. From the 4th wash to the 16th wash a twofold amount of $^2$H$_2$O was used with stirring for at least one hour if at daytime, or add a threefold amount without stirring if overnight. Usually 3–4 overnight washes were used. Gas evolved during the washes and during the last washes a strong white color appeared. After the 16th wash the catalyst was ready for use (total $^2H_2O$ used ~50 ml).

Methyl α/β-D-ribofuranoside-1#,2,3,4#,5,5'-$^2H_6$ (2) (# denotes partial deuteration). To a mixture of methyl α/β-ribofuranoside (1.4 g, 8.5 mmol) coevaporated two times with deuterium oxide (99.8% atom D, ~6 ml each) and dissolved in the same solvent (28 ml) deuterated Raney-Ni (settled volume: 14.5 ml) was added using a graduated pipette and after bubbling nitrogen through the mixture for 10 min, it was refluxed with good stirring at 110° C. in an oil bath for 7 days in an atmosphere of nitrogen. The mixture was filtered through a bed of celite, washed with water, and the combined aqueous phases were evaporated to give a syrup. Yield: 0.84 g (82%). $^1$H-NMR ($D_2O$) of main components 2 [α/β=~3:7]: (α-anomer): 4.92 (s, 1H) H-1; 4.02 (s, 0.3H) H-4; 3.37 (s, 3H) $OCH_3$; (β-anomer): 4.83 (s, 1H) H-1; 3.93 (s, 0.7H) H-4; 3.33 (s, 3H) $OCH_3$. $^{13}$C-NMR ($D_2O$) (α-anomer): 103.5 (C-1); 84.9 (C-4); 55.8 ($OCH_3$); (β-anomer): 108.3 (C-1); 83.1 (C-4); 55.52 ($OCH_3$). MS: ($FAB^-$) $(M-H)^-$ Calc. for $C_6H_7{}^2H_4O_5{}^-$: 167.0858 found 167.0840 (19%); for $C_6H_6{}^2H_5O_5{}^-$: 168.0921 found 168.0902 (65%); for $C_6H_5{}^2H_6O_5{}^-$: 169.0983 found 167.0967 (15%).

1-O-Methyl-2,3,5-tri-O-(4-toluoyl)-α/β-D-ribofuranoside -1#,2,3,4#,5,5'-$^2H_6$ (4). Methyl α/β-D-ribofuranoside-2,3,4#,5',5"-$^2H_4$ (2) (1.49 g, 8.8 mmol) was coevaporated with dry pyridine 5 times to get a dry thick syrup which subsequently was dissolved in dry pyridine (44 ml). This solution was cooled to 0° C. in an ice-bath, then toluoyl chloride (7 ml, 53 mmol) was added in one portion with stirring. Stirring was maintained for 20 min at bath temperature, then at room temperature overnight, when Tlc showed complete consumption of starting sugar. After addition of methanol and additional 5 min's stirring, usual work-up resulted in an oily residue which was subjected to short column chromatography. First column (120 g silica) was packed, loaded and washed with 75% petroleum ether in $CH_2Cl_2$ until complete removal of reagent residue then the polarity was increased, Mixed fractions were re-chromatographed starting with 20% petroleum ether in dichloromethane followed by sequential increase of polarity (a series of similar colums was necessary on mixed fractions). After four columns sufficiently pure compound 4 was obtained as a thick syrup. Yield: 2.19 g (48%). $^1$H-NMR ($CDCl_3$): 8.0-7.1 (m, 9H) toluoyl (α+β anomers); (β-anomer) 5.13 (s, 1H) H-1; 4.70 (s) H-4#; 3.40 (s, 3H) $OCH_3$; (α-anomer) 5.37 (s, 1H) H-1; 4.61 (s) H-4#; 3.47 (s, 3H) $OCH_3$; 2.39 & 2.36 (2xs, 9H) 3x toluoyl-$CH_3$ (α+β anomers).

1-O-Acetyl-2,3,5-tri-O-(4-toluoyl)-α/β-D-ribofuranoside -1#,2,3,4#,5,5'-$^2H_6$ (6). _1-O-Methyl-2,3,5-tri-O-toluoyl-α/β-D-ribofuranoside 2,3,4#,5,5'-$^2H_4$ 4 (1.57 g, 3 mmol) was dissolved in acetic acid (4.3 ml) and acetic anhydride (1.0 ml) and treated with sulfuric acid (0.23 ml) with ice-cooling. Resulting mixture was stirred overnight at room temperature, then ice-water was added followed by usual work-up. Short column chromatography similar as for compound 4 gave 6 as a white foam. Yield: 1.36 g (82%). $^1$H-NMR ($CDCl_3$): 8.1-7.1 (m, 9H) toluoyl (α+β anomers); (β-anomer): 6.41 (s, 1H) H-1; 4.75 (s) H-4#; 2.01 (s, 3H) acetyl; (α-anomer) 6.68 (s, 1H) H-1; 2.13 (s, 3H) acetyl; 2.41 & 2.37 (2xs, 9H) 3x toluoyl-$CH_3$ (α+β anomers).

2',3',5'-Tri-O-(4-toluoyl)-1'#,2',3',4'#,5',5"-$^2H_6$-uridine (7). Uracil (73 mg, 0.65 mmol) was coevaporated with dry toluene (2×) then suspended in 1,1,1,3,3,3-hexamethyldisilazane (3.9 ml) followed by addition of chlorotrimethylsilane (0.39 ml) and the heterogeneous mixture was refluxed at 120° C. under an atmosphere of nitrogen for 60 min. The clear solution resulted was evaporated, then coevaporated with dry toluene (2×) to remove traces of hexamethyldisilazane. 1-O-Acetyl-2,3,5-tri-O-toluoyl-α/β-D-ribofuranoside-1#,2,3,4#,5,5'-$^2H_6$ 6 (276 mg, 0.5 mmol) was coevaporated three times with dry toluene, dissolved in 1,2-dichloroethane (6.5 ml) and added to the oily persilylated uracil followed by addition of trimethylsilyl trifluoromethanesulfonate (0.125 ml). The mixture was heated at 70° C. in nitrogene atmosphere for 4 h. Usual work-up and short column chromatography yielded compound 7. Yield: 0.23 g (75%). $R_f$: 0.45 (System B). $^1$H-NMR ($CDCl_3$): 8.81 (br. s, 1H) N—H; 8.0-7.1 (m, 12H) toluoyl; 7.42 (d, $J_{5,6}$=8.1 Hz, 1H) H-6; 6.35 (s, 1H) H-1'; 5.59 (dd, $J_{NH,5}$=2.2 Hz, 1H) H-5; 4.68 (s) H-4#; 2.42, 2,41 & 2.38 (3xs, 9H) 3x toluoyl-$CH_3$.

2',3',5'-Tri-O-(4-toluoyl)-1'#,2',3',4'#,5',5"-$^2H_6$-$N^4$-benzoylcytidine (8). $N^4$-Benzoyl-cytosine (140 mg, 0.65 mmol) was condensed with 1-O-acetyl-2,3,5-tri-O-toluoyl-α/β-D-ribofuranoside-1#,2,3,4#,5,5'-$^2H_6$ 6 (276 mg, 0.5 mmol) as written for compound 7 to afford compound 8. Yield: 0.42 g (85%). $^1$H-NMR ($CDCl_3$): 8.71 (br. s, 1H) N—H; 8.1-7.1 (m, 19H) toluoyl, benzoyl, H-5 & H-6; 6.50 (s, 1H) H-1'; 4.75 (s) H-4#; 2.44 & 2.20 (2xs, 9H) 3x toluoyl-$CH_3$.

2',3',5'-Tri-O-(4-toluoyl)-1'#,2',3',4'#,5',5"-$^2H_6$-$N^6$-benzoyladenosine (9). $N^6$-Benzoyl-adenine (650 mg, 2.71 mmol) and compound 6 (1.36 g, 2.47 mmol) was condensed as for compound 7. Usual work-up and short column chromatography afforded compound 9. Yield: 1.2 g (60%). $R_f$: 0.53 (System B). $^1$H-NMR ($CDCl_3$): 8.98 (br. s, 1H) N—H; 8.72 (s. 1H) H-8; 8.17 (s, 1H) H-2; 8.1-7.1 (m, 17H) toluoyl, benzoyl; 6.50 (s, 1H) H-1'; 4.82 (s) H-4#; 2.42 & 2.38 (2xs, 9H) 3x toluoyl-$CH_3$.

2',3',5'-Tri-O-(4-toluoyl)-1'#,2',3',4'#,5',5"-$^2H_6$-$N^2$-acetyl-$O^6$-diphenylcarbamoyl guanosine (10). $N^2$-acetyl-$O^6$-diphenylcarbamoylguanine (253 mg, 0.65 mmol) was condensed with the deuterated sugar derivative 6 (276 mg, 0.5 mmol) according to literature procedure[37]. Yield: 0.32 g (73%). $^1$H-NMR ($CDCl_3$): 8.10 (br. s, 1H) N—H; 8.05 (s. 1H) H-8; 8.0-7.1 (m, 22H) toluoyl, phenyls; 6.33 (s, 1H) H-1'; 4.82 (s) H-4#; 2.48 (s, 3H) acetyl; 2.42 & 2.38 (2xs, 9H) 3x toluoyl-$CH_3$.

1-(2',3',5'-Tri-O-(4-toluoyl)-1'#,2',3',4'#,5',5"-$^2H_6$-β-D-ribofuranosyl)-thymine (11). Thymine (82 mg, 0.65 mmol) was condensed with sugar derivative 6 (276 mg, 0.5 mmol) as written for compound 7. Yield: 0.28 g (91%). $^1$H-NMR ($CDCl_3$): 8.35 (br.s, 1H) N—H; 8.05 (s, 1H) H-8; 7.37-7.30 (m, 10H) Ar.; 6.09 (s, 1H) H-1'; 4.45 (s) H-4#; 2.46 (s, 3H) Ac-$N^2$; 2.15-1.88 (3xs, 9H) 3xOAc.

1'#,2',3',4'#,5',5"-$^2H_6$-Uridine (12). Compound 7 (264 mg, 0.43 mmol) treated as written for compound 14, but partition between water and dichloromethane followed by dichloromethane wash of water (3×) phase was used for purification. Evaporation of water gave crude compound 12. Yield: 87 mg (99%). $^1$H-NMR ($D_2O$, 500 MHz): 7.82 (d, $J_{5,6}$=8.0 Hz, 1H) H-6; 5.84 (s, 1H) H-1'; 5.83 (d, 1H) H-5; 4.05 (s) H-4#. MS: ($FAB^-$) $(M-H)^-$ Calc. for $C_9H_7{}^2H_4N_2O_6{}^-$: 247.0868 found 247.0877 (18%); for $C_9H_6{}^2H_5N_2O_6{}^-$: 248.0931 found 248.0926 (66%); for $C_9H_5{}^2H_6N_2O_6{}^-$: 249.0994 found 249.0981 (14%).

1'#,2',3',4'#,5',5"-$^2H_6$-$N^4$-Benzoylcytidine (13). Compound 8 (0.77 g, 1.1 mmol) was treated as written for compound 14 to give crude compound 13 with minor impurities. Yield: 0.375 g (98%). $^1$H-NMR ($CDCl_3$/ methanol-d$_4$/DMSO-d$_6$): 8.53 (d, J$_{5,6}$=7.7 Hz, 1H) H-6; 8.1-7.4 (m, 5H) benzoyl; 7.44 (d, J$_{5,6}$=7.7 Hz, 1H) H-5; 5.88 (s, 1H) H-1'; 4.03 (s) H-4'. MS: (FAB$^+$) (M+H)$^+$ Calc. for C$_{16}$H$_{14}^2$H$_4$N$_3$O$_6$$^+$: 352.1447 found 352.1433 (19%); for C$_{16}$H$_{13}^2$H$_5$N$_3$O$_6$$^+$: 353.1510 found 353.1519 (66%); for C$_{16}$H$_{12}^2$H$_6$N$_3$O$_6$$^+$: 354.1572 found 354.1561 (14%).

1'#,2',3',4'#,5',5"-$^2$H$_6$-N$^6$-Benzoyladenosine (14). Compound 9 (1.17 g, 1.6 mmol) was dissolved in a mixture of pyridine (3.2 ml, 2.0 ml/mmol) and ethanol (4.8 ml, 3.0 ml/mmol), and ethanolic sodium hydroxide solution (prepared from 6.4 ml 2N aqueous sodium hydroxide and 6.4 ml ethanol) was added. After stirring for 5 min at room temperature, the solution was neutralized by addition of Dowex ion exchange resin (H$^+$ form). Resin was filtered off, then washed with ethanol (200 ml), the combined filtrate and washing were evaporated. Repeated coevaporation with toluene gave a powder which was triturated with diethylether, filtered then rinsed with diethylether again. The air dried crude 14 was sufficiently pure for being taken in the next step. Yield: 0.63 g (105%). $^1$H-NMR (CDCl$_3$/methanol-d$_4$): 8.73 (s, 1H) H-8; 8.37 (s, 1H) H-2; 8.1-7.4 (m, 5H) benzoyl; 6.01 (s, 1H) H-1'; 4.25 (s) H-4#'. MS: (FAB$^+$) (M+H)$^+$ Calc. for C$_{17}$H$_{14}^2$H$_4$N$_5$O$_5$$^+$: 376.1559 found 376.1551 (19%); for C$_{17}$H$_{13}^2$H$_5$N$_5$O$_5$$^+$: 377.1622 found 377.1612 (65%); for C$_{17}$H$_{12}^2$H$_6$N$_5$O$_5$$^+$: 378.1685 found 378.1671 (15%).

1'#,2',3',4'#,5',5"-$^2$H$_6$-N$^2$-Acetyl-O$^6$-diphenylcarbamoylguanosine (15). Compound 10 (316 mg, 0.36 mmol) was treated as described for compound 14, but instead of trituration, a short column of silica was run to afford compound 15. Yield: 150 mg (79%). $^1$H-NMR (CDCl$_3$/methanol-d$_4$): 8.58 (s, 1H) H-8; 7.4 -7.2 (m, 10H) phenyls; 6.08 (s, 1H) H-1'; 4.13 (s) H-4#'; 2.28 (s, 3H) N$^2$-OAc. MS: (FAB$^+$) (M+H)$^+$ Calc. for C$_{25}$H$_{21}^2$H$_4$N$_6$O$_7$$^+$: 525.2036 found 525.2018 (18%); for C$_{25}$H$_{20}^2$H$_5$N$_6$O$_7$$^+$: 526.2099 found 526.2082 (65%); for C$_{25}$H$_{19}^2$H$_6$N$_6$O$_7$$^+$: 527.2162 found 527.2151 (16%).

1-(1'#,2',3',4'#,5',5"-$^2$H$_6$-β-D-Ribofuranosyl)-thymine (16). Compound 11 (264 mg, 0.43 mmol) treated as written for compound 12 to obtain crude compound 16. Yield: 112 mg (99%). $^1$H-NMR (D$_2$O, 500 MHz): 7.61 (d, J$_{SCH3,6}$=1.2 Hz, 1H) H-6; 5.83 (s, 1H) H-1'; 4.03 (s) H-4#', 1.81 (d, 3H) 5-CH$_3$. MS: (FAB$^-$) (M–H)$^-$ Calc. for C$_{10}$H$_9^2$H$_4$N$_2$O$_6$$^-$: 261.1025 found 261.1039 (18%); for C$_{10}$H$_8^2$H$_5$N$_2$O$_6$$^-$: 262.1088 found 262.1079 (65%); for C$_{10}$H$_7^2$H$_6$N$_2$O$_6$$^-$: 263.1151 found 263.1138 (15%).

Procedure A: 5'-O-MMTr-1'#,2',3',4'#,5',5"-$^2$H$_6$-uridine (17). To a solution of compound 12 (110 mg, 0.44 mmol), in dry pyridine (5 ml), MMTr-Cl (178 mg, 0.575 mmol) was added and stirred overnight at room temperature. After usual-work up and purification on short silica gel column compound 17 was obtained. Yield 121 mg (53%). $^1$H-NMR (CDCl$_3$): 8.0 (d, J$_{5,6}$=8.06 Hz, 1H) H-6; 7.5-6.8 (m, 14H) MMTr; 5.88 (s, 1H) H-1'; 5.33 (d, 1H) H-5; 4.15 (s) H-4#'; 3.77 (s, 3H) OCH$_3$.

5'-O-MMTr-1'#,2',3',4'#,5',5"-$^2$H$_6$-N$^4$-benzoylcytidine (18). Compound 13 (116 mg, 0.33 mmol) was treated with MMTr-Cl (122 mg, 0.39 mmol.) according to Procedure A. Yield 161 mg (78%). $^1$H-NMR (CDCl$_3$): 8.84 (br.s, 1H) N—H; 8.26 (d, J$_{5,6}$=7.57 Hz, 1H) H-6; 8.0-6.8 (m, 19H) MMTr+benzoyl; 5.87 (s, 1H) H-1'; 4.39 (s) H-4#'; 3.78 (s, 3H) OCH$_3$.

5'-O-MMTr-1'#,2',3',4'#,5',5"-$^2$H$_6$-N$^6$-benzoyladenosine (19). Compound 14 (150 mg, 0.4 mmol) was treated with MMTr-Cl (185 mg, 0.6 mmol) as in Procedure A. Yield: 186 mg. (72%). $^1$H-NMR (CDCl$_3$): 9.28 (br. s, 1H) NH; 8.66 (s, 1H) H-8; 8.24 (s, 1H) H-2; 8.1-6.7 (m, 19H) MMTr+benzoyl; 6.07 (s, 1H) H-1'; 4.38 (s) H-4#'; 3.75 (s, 3H) OCH$_3$.

5'-O-MMTr-1'#,2',3',4'#,5',5"-$^2$H$_6$-N$^2$-acetyl-O$^6$-diphenylcarbamoylguanosine (20). Procedure A was applied to compound 15 (145 mg, 0.275 mmol) and MMTr-Cl (102 mg, 0.33 mmol). Yield: 172 mg (78%). $^1$H-NMR (CDCl$_3$): 8.54 (s, 1H) N—H; 8.19 (s, 1H) H-8; 7.5-6.7 (m, 24H) MMTr+phenyls; 5.92 (s, 1H) H-1'; 4.49 (s) H-4#'; 3.75 (s, 3H) OCH$_3$; 2.23 (s, 3H) N$^2$-OAc.

Procedure B: 5'-O-MMTr-2',3'-di-O-acetyl-1'#,2',3',4'#,5',5"-$^2$H$_6$-uridine (21). Compound 17 (108 mg, 0.207 mmol) was coevaporated with dry pyridine (3×) then re-dissolved in dry pyridine (4 ml) and treated with acetic anhydride (63.5 mg, 2.5 mol eq.) and stirred at room temperature overnight. After usual work-up and purification on silica gel column compound 21 was obtained. Yield: 106 mg (85%). $^1$H-NMR (CDCl$_3$): 8.25 (br. s, 1H) N—H; 7.69 (d, J$_{5,6}$=8.3 Hz, 1H) H-6; 7.4-6.8(m, 14H) MMTr; 6.23 (s, 1H) H-1'; 5.32 (d, 1H) H-5; 4.22 (s) H-4#'; 3.81 (s, 3H) OCH$_3$; 1.60 (s,6H) OAc.

5'-O-MMTr-2',3'-di-O-acetyl-1'#,2',3',4'#,5',5"-$^2$H$_6$-N$^4$-benzoylcytidine (22). Compound 18 (142 mg, 0.227 mmol) was treated as in Procedure B. Yield: 157 mg (97%). $^1$H-NMR (CDCl$_3$): 8.25 (d, 1H) H-6; 8.0-6.8 (m, 19H) MMTr+benzoyl.; 6.32 (s, 1H) H-1'; 4.30 (s, 1H) H-4'; 3.82 (s, 3H) OMe; 2.12, 2.07 (2xs, 6H) 2xOAc.

5'-O-MMTr-2',3'-di-O-acetyl-1'#,2',3',4'#,5',5"-$^2$H$_6$-N$^6$-benzoyladenosine (23). Treatment of compound 19 (200 mg, 0.3 mmol) as in Procedure B afforded compound 23. Yield 208 mg (92%). $^1$H-NMR (CDCl$_3$): 8.59 (s, 1H) H-8; 8.25 (s, 1H) H-2; 7.7-6.8 (m, 19H) MMTr+benzoyl; 6.30 (s, 1H) H-1'; 4.33 (s) H-4#'; 3.78 (s, 3H) OMe; 2.12, 2.05 (2xs, 6H) OAc.

5'-O-MMTr-2',3'-di-O-acetyl-1'#,2',3',4'#,5',5"-$^2$H$_6$-N$^2$-acetyl-O$^6$-diphenylcarbamoylguanosine (24). Compound 20 (60 mg, 0.075 mmol) was acetylated according to Procedure B. Yield: 52 mg (78%). $^1$H-NMR (CDCl$_3$): 8.06 (s, 1H) H-8; 7.4-6.8 (m, 24H) MMTr+phenyls; 6.17 (s, 1H) H-1'; 4.32 (s) H-4#'; 3.75 (s, 3H) OMe; 2.36-2.05 (3xs, 9H) 3x Ac.

Procedure C: 2',3'-Di-O-acetyl-1'#,2',3',4'#,5',5"-$^2$H$_6$-uridine (25). Compound 21 (100 mg, 0.165 mmol) was dissolved in 80% acetic acid (8 ml) at room temperature and stirred overnight then volatile materials were evaporated and residue coevaporated with toluene twice. Purification on silica gel column gave compound 25. Yield 52 mg (95%). $^1$H-NMR (CDCl$_3$): 8.62 (br.s, 1H) N—H; 7.72 (d, J$_{5,6}$=8.06 Hz, 1H) H-6; 6.04 (s, 1H) H1'; 5.78 (d, 1H) H-5; 4.21 (s) H-4#'; 2.14, 2.09 (2xs, 6H) 2x OAc.

2',3'-Di-O-acetyl-1'#,2',3',4'#,5',5"-$^2$H$_6$-N$^4$-benzoylcytidine (26). Compound 22 (140 mg, 0.198 mmol) was subjected to Procedure C to give compound 26. Yield: 70 mg (81%). $^1$H-NMR (CDCl$_3$): 8.29 (d, 1H) H-6; 7.9-7.5 (m, 6H) benzoyl+H-5; 6.12 (s, 1H) H-1'; 4.27 (s, 1H) H-4'; 2.11, 2.08 (2xs, 6H) 2x OAc.

2',3'-Di-O-acetyl-1'#,2',3',4'#,5',5"-$^2$H$_6$-N$^6$-benzoyladenosine (27). Procedure C was performed on compound 23 (215 mg, 0.28 mmol) to give compound 27. Yield 132 mg (94%). $^1$H-NMR (CDCl$_3$): 9.27 (br. s, 1H) N—H; 8.76 (s, 1H) H-8; 8.13 (s, 1H) H-2; 8.1-7.5 (m, 5H) benzoyl; 6.13 (s, 1H) H-1'; 4.36 (s) H-4#'; 2.17-2.02 (2xs, 6H) 2x OAc.

2',3'-Di-O-acetyl-1'#,2',3',4'#,5',5"-$^2$H$_6$-N$^2$-acetyl-O$^6$-diphenylcarbamoylguanosine (28). Compound 24 (100 mg, 0.113 mmol) was treated according to Procedure C to obtain compound 28. Yield: 40 mg (58%). $^1$H-NMR (CDCl$_3$): 8.05

(s, 1H) H-8; 7.4-7.3 (m, 10H) phenyls; 6.03 (s, 1H) H-1'; 4.31 (s) H-4#'; 2.39-2.02 (3xs, 9H) 3xAc.

Procedure D: 1-(3',5'-O-(TPDS)-1'#,2',3',4'#,5',5"-$^2$H$_6$-β-D-ribofuranosyl)-thymine (32). 1-(2',3',4#',5',5"-$^2$H$_4$-β-D-Ribofuranosyl)-thymine 16 (0.53 g, 1.5 mmol) was repeatedly coevaporated with dry pyridine and re-dissolved in the same solvent (15 ml). After addition of 1,3-dichloro-1,1,3,3-tetraisopropyl disiloxane (0.62 ml, 1.95 mmol, 1.3 mol eq.), the resulting solution was stirred under dry condition for 1 h, followed by normal work-up. The resulting syrup was chromatographed on a short column of silica gel to give compound 32 as a foam. Yield: 0.46 g (61%). $^1$H-NMR (CDCl$_3$): 9.31 (br. s, 1H) N—H; 7.44 (d, J$_{SCH3,6}$=1.2 Hz, 1H) H-6; 5.71 (s, 1H) H-1'; 3.99 (s) H-4#'; 1.90 (br. s, 3H) 5-CH$_3$; 1.1-1.0 (m, 24H) CH$_3$ of TPDS.

3',5'-O-(TPDS)-1'#,2',3',4'#,5',5"-$^2$H$_6$-N$^4$-benzoylcytidine (29). Procedure D was applied to compound 18 (0.66 g, 1.88 mmol) to give compound 29 as a foam. Yield: 0.96 g (85%). $^1$H-NMR (CDCl$_3$): 8.28 (d, J$_{5,6}$=7.6 Hz, 1H) H-6; 8.0 -7.4 (m, 5H) benzoyl; 5.86 (s, 1H) H-1'; 4.23 (s) H-4#'; 1.1-1.0 (m, 24H) CH$_3$ of TPDS.

3',5'-O-(TPDS)-1'#,2',3',4'#,5',5"-$^2$H$_6$-N$^6$-benzoyladenosine (30). Procedure D was carried out on compound 19 (0.57 g, 1.52 mmol) to afford compound 30 as a foam. Yield: 0.72 g (77%). $^1$H-NMR (CDCl$_3$): 9.26 (br. s., 1H) N—H; 8.74 (s, 1H) H-8; 8.15 (s, 1H) H-2; 8.1-7.4 (m, 5H) Bz; 6.03 (s, 1H) H-1'; 4.11 (s) H-4#'; 1.1-1.0 (m, 24H) methyls of TPDS.

3',5'-O-(TPDS)-1'#,2',3',4'#,5',5"-$^2$H$_6$-N$^2$-acetyl-O$^6$-diphenylcarbamoylguanosine (31). Treatment of compound 20 (152 mg, 0.29 mmol) according to Procedure D gave compound 31. Yield: 185 mg (83%). $^1$H-NMR (CDCl$_3$): 8.29 (br. s., 1H) N—H; 8.18 (s, 1H) H-8; 7.5-7.2 (m, 10H) phenyls; 6.01 (s, 1H) H-1'; 4.12 (s) H-4#'; 2.49 (s, 3H) Ac; 1.1-1.0 (m, 24H) methyls of TPDS.

Procedure E: 1-(2'-O-Phenoxythiocarbonyl-3',5'-O-(TPDS)-1'#,2',3',4'#,5',5"-$^2$H$_6$-β-D-ribofuranosyl)thymine (36). To the mixture of vacuum-dried 32 (0.46 g, 0.92 mmol) and 1-methylimidazole (0.147 ml, 1.84 mmol, 2.0 mol eq.) in dry dichloromethane (10 ml), phenyl chlorothionoformate (0.179 ml, 1.29 mmol, 1.4 mol eq.) was added and stirred in nitrogen atmosphere at room temperature overnight. After dilution with dichloromethane, the reaction mixture was poured into saturated sodium hydrogene carbonate solution and extracted with dichloromethane. Pooled organic phases were washed with sat. citric acid solution (2x), dried with MgSO$_4$, evaporated and the residue was purified on a short column of silica gel to afford compound 32. Yield: 0.58 g (89%). $^1$H-NMR (CDCl$_3$): 8.66 (br. s., 1H) N—H; 7.6-7.0 (m, 6H) H-6+phenoxy; 5.92 (s, 1H) H-1'; 4.05 (s) H-4#'; 1.92 (d, J$_{SCH3,6}$=1.2 Hz, 3H) 5-CH$_3$; 1.1-1.0 (m, 24H) methyls of TPDS.

2'-O-Phenoxythiocarbonyl-3',5'-O-(TPDS)-1'#,2',3',4'#,5',5"-$^2$H$_6$-N$^4$-benzoylcytidine (33). Compound 29 (0.92 g, 1.55 mmol) was converted to compound 33 using Procedure E. Yield: 0.98 g (87%). $^1$H-NMR (CDCl$_3$): 8.88 (br. s., 1H) N—H; 8.27 (d, J$_{5,6}$=7.6 Hz, 1H) H-6; 8.0-7.1 (m, 11H) phenoxy+benzoyl+H-5; 6.08 (s, 1H) H-1'; 4.19 (s) H-4#'; 1.1-1.0 (m, 24H) CH$_3$ of TPDS.

2'-O-Phenoxythiocarbonyl-3',5'-O-(TPDS)-1'#,2',3',4'#,5',5"-$^2$H$_6$-N$^6$-benzoyladenosine (34). Compound 30 (0.72 g, 1.16 mmol) was subjected to Procedure E to afford compound 34. Yield: 0.77 g (88%). $^1$H-NMR (CDCl$_3$): 9.21 (br. s., 1H) N—H; 8.78 (s, 1H) H-8; 8.19 (s, 1H) H-2; 8.1-7.1 (m, 10H) phenoxy+benzoyl; 6.24 (s, 1H) H-1'; 4.14 (s) H-4#'; 1.1-1.0 (m, 24H) CH$_3$ of TPDS.

2'-O-Phenoxythiocarbonyl-3',5'-O-(TPDS)-1'#,2',3',4'#,5',5"-$^2$H$_6$-N$^2$-acetyl-O$^6$-diphenylcarbamoylguanosine (35) was obtained upon treatment of compound 32 (0.28 g, 0.37 mmol) as described in Procedure E. Yield: 0.30 g (89%). $^1$H-NMR (CDCl$_3$): 8.12 (s, 1H) H-8; 7.94 (br. s, 1-H) N—H; 7.6-7.0 (m, 15H) phenoxy; 6.20 (s, 1H) H-1'; 4.17 (s) H-4#'; 2.58 (s, 3H) Ac; 1.1-1.0 (m, 24H) methyls of TPDS.

Procedure F: 3',5'-O-(TPDS)-1'#,2',2",3',4'#,5',5"-$^2$H$_7$-thymidine (40). After coevaporation with dry toluene, compound 36 (0.70 g, 1.12 mmol) was dissolved in the same solvent (20 ml) and AIBN (37 mg, 0.23 mmol, 0.2 mol eq.) and tri-n-butyltin deuteride (0.46 ml, 1.71 mmol, 1.5 mol eq.) were added. The solution was degassed by nitrogen bubbling for 20 min followed by heating at 75° C. under nitrogen atmosphere for 3.5 h. Volatile materials were evaporated, the residual oil was subjected to column chromatography to afford compound 40. Yield: 0.52 g (95%). R$_f$: 0.44 (System B). $^1$H-NMR (CDCl$_3$): 9.04 (br. s., 1H) N—H; 7.42 (d, J$_{SCH3,6}$=1.2 Hz, 1H) H-6; 6.08 (s, 1H) H-1'; 3.74 (s) H-4#'; 1.92 (d, 3H) 5-CH$_3$; 1.1-1.0 (m, 24H) methyls of TPDS.

3',5'-O-(TPDS)-1'#,2',2",3',4'#,5',5"-$^2$H$_7$-N$^4$-benzoyl-2'-deoxycytidine (37). Procedure F was done on compound 33 (0.29 g, 0.39 mmol) for 14 h to give compound 37 as a foam. Yield: 0.17 g (75%). $^1$H-NMR (CDCl$_3$): 8.78 (br. s., 1H) N—H; 8.33 (d, J$_{5,6}$=7.7 Hz, 1H) H-6; 8.0-7.4 (m, 6H) benzoyl+H-5; 6.08 (s, 1H) H-1'; 3.83 (s) H-4#'; 1.1-1.0 (m, 24H) CH$_3$ of TPDS.

3',5'-O-(TPDS)-1'#,2',2",3',4'#,5',5"-$^2$H$_7$-N$^6$-benzoyl-2'-deoxyadenosine (38) was obtained upon treatment of compound 34 (0.76 g, 1.01 mmol) according to Procedure F. Yield: 0.47+0.07 g (77+15%). $^1$H-NMR (CDCl$_3$): 9.13 (br. s., 1H) N—H; 8.77 (s, 1H) H-8; 8.17 (s, 1H) H-2; 8.1-7.4 (m, 5H) benzoyl; 6.04 (s, 1H) H-1'; 4.12 (s) H-4#'; 1.1-1.0 (m, 24H) methyls of TPDS.

3',5'-O-(TPDS)-1'#,2',2",3',4'#,5',5"-$^2$H$_7$-N$^2$-acetyl-O$^6$-diphenylcarbamoyl-2'-deoxyguanosine (39). Compound 35 (0.66 g, 0.73 mmol) was treated as in Procedure F to obtain compound 39. Yield: 0.53 g (96%). $^1$H-NMR (CDCl$_3$): 8.21 (s, 1H) H-8; 8.03 (br. s., 1H) N—H; 7.6-7.1 (m, 10H) phenyls; 6.30 (s, 1H) H-1'; 3.89 (s) H-4#'; 2.55 (s, 3H) Ac; 1.1-1.0 (m, 24H) CH$_3$ of TPDS.

Procedure G: 1'#,2',2",3',4'#,5',5"-$^2$H$_7$-Thymidine (44). Compound 40 (0.49 g, 1.0 mmol) was dissolved in dry tetrahydrofurane (10 ml) and 1.0M TBAF solution in dry THF (1 ml, 1.0 mmol, 1.0 mol. eq.) was added. After stirring for 5 min, volatile materials were evaporated and the residue was purified on silica gel to give compound 44. Yield: 0.22 g (83%). $^1$H-NMR (CDCl$_3$/MeOH-d$_4$): 7.70 (d, J$_{SCH3,6}$=1.2 Hz, 1H) H-6; 6.26 (s, 1H) H-1'; 3.92 (s) H-4#'; 1.92 (d, 3H) 5-CH$_3$. MS: (FAB$^-$) (M—H)$^-$ Calc. for C$_{10}$H$_8$$^2$H$_5$N$_2$O$_5^-$: 246.1139 found 246.1123 (17%); for C$_{10}$H$_7$$^2$H$_6$N$_2$O$_5^-$: 247.1201 found 247.1221 (65%); for C$_{10}$H$_6$$^2$H$_7$N$_2$O$_5^-$: 248.1264 found 248.1259 (15%).

1'#,2',2",3',4'#,5',5"-$^2$H$_7$-N$^4$-Benzoyl-2'-deoxycytidine (41) was obtained when compound 37 (153 mg, 0.26 mmol) was treated according to Procedure G. Yield: 77 mg (88%). $^1$H-NMR (CDCl$_3$/MeOH-d$_4$): 8.53 (d, J$_{5,6}$=7.6 Hz, 1H) H-6; 8.1-7.5 (m, 6H) benzoyl+H-5; 6.23 (s, 1H) H-1'; 4.03 (s) H-4#'. MS: (FAB$^+$) (M+H)$^+$ Calc. for C$_{16}$H$_{13}$$^2$H$_5$N$_3$O$_5^+$: 337.1561 found 337.1572 (19%); for C$_{16}$H$_{12}$$^2$H$_6$N$_3$O$_5^+$: 338.1623 found 338.1639 (64%); for C$_{16}$H$_{11}$$^2$H$_7$N$_3$O$_5^+$: 339.1686 found 338.1671 (14%).

1'#,2',2",3',4'#,5',5"-$^2$H$_7$-N$^6$-Benzoyl-2'-deoxyadenosine (42). Compound 38 (0.51 g, 0.84 mmol) was subjected to the treatment in Procedure G to afford compound 42. Yield: 0.28 g (93%). $^1$H-NMR (CDCl$_3$/MeOH-d$_4$): 8.75 (s, 1H) H-8; 8.34 (s, 1H) H-2; 8.1-7.4 (m, 5H) benzoyl; 6.46 (s, 1H) H-1'; 4.17 (s) H-4#'. MS: (FAB$^+$) (M+H)$^+$ Calc. for C$_{17}$H$_{13}$$^2$H$_5$N$_5$O$_4$$^+$: 361.1673 found 361.1685 (19%); for C$_{17}$H$_{12}$$^2$H$_6$N$_5$O$_4$$^+$: 362.1735 found 362.1721 (64%); for C$_{17}$H$_{11}$$^2$H$_7$N$_5$O$_4$$^+$: 363.1798 found 363.1781 (15%).

1'#,2',2",3',4'#,5',5"-$^2$H$_7$-N$^2$-Acetyl-O$^6$-diphenylcarbamoyl-2'-deoxyguanosine (43). Upon treatment of compound 39 (0.21 g, 0.27 mmol) with TBAF as in Procedure G compound 43 was obtained. Yield: 0.22 g (80%). $^1$H-NMR (CDCl$_3$): 8.89 (br. s., 1H) N—H; 8.20 (s, 1H) H-8; 7.5-7.1 (m, 10H) phenyls; 6.26 (s, 1H) H-1'; 3.97 (s) H-4#'; 2.30 (s, 3H) N$^2$-Ac. MS: (FAB$^+$) (M+H)$^+$ Calc. for C$_{25}$H$_{20}$$^2$H$_5$N$_6$O$_6$$^+$: 510.2150 found 510.2157 (18%); for C$_{25}$H$_{19}$$^2$H$_6$N$_6$O$_6$$^+$: 511.2212 found 511.2201 (64%); for C$_{25}$H$_{18}$$^2$H$_7$N$_6$O$_6$$^+$: 512.2275 found 512.2258 (14%).

5'-O-MMTr-1'#,2',2",3',4'#,5',5"-$^2$H$_7$-N$^4$-benzoyl-2'-deoxycytidine (45) was obtained upon subjecting compound 41 (0.15 g, 0.44 mmol) to a treatment as in Procedure A. Yield: 0.23 g (87%). $^1$H-NMR (CDCl$_3$): 8.82 (br. s., 1H) N—H; 8.28 (d, J$_{5,6}$=7.3 Hz, 1H) H-6; 8.1-6.7 (m, 20H) MMTr+benzoyl+H-5; 6.30 (s, 1H) H-1'; 4.18 (s) H-4#'; 3.79 (s, 3H) OCH$_3$.

5'-O-MMTr-1'#,2',2",3',4'#,5',5"-$^2$H$_7$-N$^6$-benzoyl-2'-deoxyadenosine (46). Compound 42 (0.27 g, 0.75 mmol) was treated according to Procedure A to obtain compound 46. Yield: 0.43 g (90%). $^1$H-NMR (CDCl$_3$): 9.14 (br. s., 1H) N—H; 8.71 (s, 1H) H-8; 8.14 (s, 1H) H-2; 8.1-6.7 (m, 19H) MMTr+benzoyl; 6.46 (s, 1H) H-1'; 4.15 (s) H-4#'; 3.76 (s, 3H) OCH$_3$.

5'-O-MMTr-1'#,2',2",3',4'#,5',5"-$^2$H$_7$-N$^2$-acetyl-O$^6$-diphenylcarbamoyl-2'-deoxyguanosine (47). Compound 43 (0.11 g, 0.22 mmol) was treated according to Procedure A. Yield: 0.15 g (84%). $^1$H-NMR (CDCl$_3$): 8.20 (br. s., 1H) N—H; 8.08 (s, 1H) H-8; 7.5-6.7 (m, 24H) MMTr+phenyls; 6.42 (s, 1H) H-1'; 4.14 (s) H-4#'; 3.73 (s, 3H) OCH$_3$; 2.36 (s, 3H) N$^2$-Ac.

5'-O-MMTr-1'#,2',2",3',4'#,5',5"-$^2$H$_7$-thymidine (48). Compound 44 (0.22 g, 0.88 mmol) was treated as in Procedure A. Yield: 0.4 g (88%). $^1$H-NMR (CDCl$_3$): 9.45 (br. s., 1H) N—H; 7.60 (d, J$_{SCH3,6}$=1.2 Hz, 1H) H-6; 7.5-6.78 (m, 14H) MMTr; 6.42 (s, 1H) H-1'; 4.07 (s) H-4#'; 3.78 (s, 3H) OCH$_3$; 1.45 (d, 3H) 5-CH$_3$.

3'-O-Acetyl-5'-O-MMTr-1'#,2',2",3',4'#,5',5"-$^2$H$_7$-N$^4$-benzoyl-2'-deoxycytidine (49) was obtained by Procedure B treating compound 45 (0.23 g, 0.38 mmol). Yield: 0.22 g (89%). $^1$H-NMR (CDCl$_3$): 8.75 (br. s., 1H) N—H; 8.16 (d, J$_{5,6}$=7.6 Hz, 1H) H-6; 8.0-6.8 (m, 20H) MMTr+benzoyl+H-5; 6.31 (s, 1H) H-1'; 4.26 (s) H-4#'; 3.8 (s, 3H) OCH$_3$; 2.08 (s, 3H) OAc.

3'-O-Acetyl-5'-O-MMTr-1'#,2',2",3',4'#,5',5"-$^2$H$_7$-N$^6$-benzoyl-2'-deoxyadenosine (50). Treatment of compound 46 (0.28 g, 0.45 mmol) as in Procedure B with 1.3 eq. of acetic anhydride at 4° C. for 24 h afforded compound 50. Yield: 0.23 g (77%). $^1$H-NMR (CDCl$_3$): 9.12 (br. s., 1H) N—H; 8.74 (s, 1H) H-8; 8.18 (s, 1H) H-2; 8.1-6.7 (m, 19H) MMTr+benzoyl; 6.52 (s, 1H) H-1'; 4.30 (s) H-4#'; 3.78 (s, 3H) OCH$_3$; 2.12 (s, 3H) OAc.

3'-O-Acetyl-5'-O-MMTr-1'#,2',2",3',4'#,5',5"-$^2$H$_7$-N$^2$-acetyl-O$^6$-di-phenylcarbamoyl-2'-deoxyguanosine (51). Compound 47 (0.25 g, 0.32 mmol) was reacted according to Procedure B. Yield: 0.25 g (94%). $^1$H-NMR (CDCl$_3$): 8.20 (s, 1H) H-8; 7.94 (br. s., 1H) N—H; 7.5-6.7 (m, 24H) MMTr+phenyls; 6.37 (s, 1H) H-1'; 4.25 (s) H-4#'; 3.75 (s, 3H) OCH$_3$; 2.42 & 2.11 (ds, 2×3H) N$^2$ & OAc.

3'-O-Acetyl-5'-O-MMTr-1'#,2',2",3',4'#,5',5"-$^2$H$_7$-thymidine (52). Procedure B was applied to compound 48 (0.4 g, 0.77 mmol). Yield: 0.36 g (83%). $^1$H-NMR (CDCl$_3$): 9.15 (br. s., 1H) N—H; 7.61 (d, J$_{SCH3,6}$=1.2 Hz, 1H) H-6; 7.4-6.8 (m, 14H) MMTr; 5.29 (s, 1H) H-1'; 4.12 (s) H-4#'; 3.80 (s, 3H) OCH$_3$; 2.08 (s, 3H) Ac; 1.41 (d, 3H) 5-CH$_3$.

Procedure H: 3'-O-Acetyl-1'#,2',2",3',4'#,5',5"-$^2$H$_7$-thymidine (56). Compound 52 (0.34 g, 0.6 mmol) was dissolved in 12 ml (20 ml/mmol) of 2% benzenesulfonic acid in dichloromethane-methanol (70/30 v/v) at RT. After 6 min this solution was neutralized with triethylamine, volatile matters were evaporated and the residue was subjected to column chromatography to give compound 56. Yield: 0.12 g (69%). $^1$H-NMR (CDCl$_3$/MeOH-d$_4$): 7.75 (d, J$_{SCH3,6}$=1.2 Hz, 1H) H-6; 6.31 (s, 1H) H-1'; 4.08 (s) H-4#'; 2.12 (s, 3H) OAc; 1.92 (d, 3H) 5-CH$_3$.

3'-O-Acetyl-1'#,2',2",3',4'#,5',5"-$^2$H$_7$-N$^4$-benzoyl-2'-deoxycytidine (53). Procedure H was carried out on compound 49 (0.21 g, 0.32 mmol). Yield: 104 mg (86%). $^1$H-NMR (CDCl$_3$): 8.27 (d, J$_{5,6}$=7.3 Hz, 1H) H-6; 8.0-7.4 (m, 6H) benzoyl+H-5; 6.27 (s, 1H) H-1'; 4.19 (s) H-4#'; 2.11 (s, 3H) OAc.

3'-O-Acetyl-1'#,2',2",3',4'#,5',5"-$^2$H$_7$-N$^6$-benzoyl-2'-deoxy-adenosine (54) was obtained upon treatment of compound 50 (0.17 g, 0.25 mmol) as in Procedure H. Yield: 90 mg (90%). $^1$H-NMR (CDCl$_3$): 9.11 (br. s., 1H) N—H; 8.78 (s, 1H) H-8; 8.11 (s, 1H) H-2; 8.1-7.4 (m, 5H) benzoyl; 6.36 (s, 1H) H-1'; 4.28 (s) H-4#'; 2.14 (s, 3H) OAc.

3'-O-Acetyl-1'#,2',2",3',4'#,5',5"-$^2$H$_7$-N$^2$-acetyl-O$^6$-diphenylcarbamoyl-2'-deoxyguanosine (55). Compound 51 (0.21 g, 0.26 mmol) was treated as in Procedure H. Yield: 112 mg (78%). $^1$H-NMR (CDCl$_3$): 8.18 (br. s., 1H) N—H; 8.10 (s, 1H) H-8; 7.5-7.2 (m, 10H) Ph; 6.26 (s, 1H) H-1'; 4.19 (s) H-4#'; 2.40 & 2.12 (ds, 2×3H) N$^2$ & OAc.

1,2:3,4-Di-O-isopropylidene-ribitol. (116). This was Ribitol 115 (7.6 g, 50 mmol) was treated as in literature[55]. Yield: 9.2 g (78%). NMR was found to be identical to the literature[59]. MS: FAB$^-$ (M–H)$^-$ Calc. for C$_{11}$H$_{20}$O$_5$$^-$: 231.1233 found 231.1224.

1,2:3,4-Di-O-isopropylidene-ribitol-5-$^2$H$_2$ (117). Deuterated Raney nickel (settled volume: 10 ml), $^2$H$_2$O (40 ml) and compound 116 (9.0 g, 38.6 mmol) were refluxed together in an oil bath for two days as written for compound 2. Similar work-up resulted compound 117. Yield: 7.3 g (79%). MS: FAB$^-$ (M–H)$^-$ Calc. for C$_{11}$H$_{17}$$^2$H$_2$O$_5$$^-$: 233.1358 found 233.1371 (98%).

2,3:4,5-Di-O-isopropylidene-D-ribose-1-$^2$H$_1$ (118). A stirred solution of compound 117 (11.75 g 50 mmol) in dry dimethyl sulfoxide (200 ml) was treated with DCC (30.88 g, 150 mmol) and methylphosphonic acid (2.41 g, 25 mmol) according to literature method[56] at RT. Yield: 7.7 g (61%). MS: FAB$^-$ (M–H)$^-$ Calc. for C$_{11}$H$_{16}$$^2$HO$_5$$^-$: 230.1139 found 230.1123 (97%).

D-Ribose-1-$^2$H$_1$ (119). Route I: Compound 118 (6.02 g, 26 mmol) was deprotected with 80% aqueous acetic acid[28]. Yield: 3.59 g (91%). MS: FAB$^-$ (M–H)$^-$ Calc. for C$_5$H$_8$$^2$HO$_5$$^-$: 150.0513 found 150.0529 (97%). Route II: Ribonolactone 125 (2.22 g, 15 mmol) was reduced to 119 by literature method[58]. Yield: 0.98 g (43%). MS: FAB$^-$ (M–H)$^-$ Calc. for C$_5$H$_8$$^2$HO$_5$$^-$: 150.0513 found 150.0497 (98%).

Methyl α/β-D-ribopyranoside-1-$^2$H$_1$ (120). Compound 119 (8 g, 53.3 mmol) was treated as for compound 1, but the mixture was refluxed for 12 h. Yield: 6.41 g (72%). MS: (FAB$^-$) (M–H)$^-$ Calc. for C$_6$H$_{10}$$^2$HO$_5$$^-$: 164.0670 found 164.0652 (98%).

Methyl α/β-D-ribopyranoside-1,2,3,4-$^2$H$_4$ (121). Compound 120 (2.51 g, 15 mmol) was refluxed with deuterated Raney-nickel (settled volume: 25 ml) in $^2H_2O$ (40 ml) for 7 days as described for compound 2. Yield: 0.79 g (31%). MS: (FAB⁻) (M–H)⁻ Calc. for $C_6H_8{}^2H_3O_5{}^-$: 166.0795 found 166.0778 (8%); $C_6H_7{}^2H_4O_5{}^-$: 167.0858 found 167.0843 (89%).

D-Ribose-1,2,3,4-$^2H_4$ (122) was obtained upon treatment of 121 (0.79 g, 4.6 mmol) was treated with aqueous HCl (0.8N, 30 ml)[28]. The solution was neutralised with Amberlist ion exchange resin (OH⁻ form), filtered and evaporated to dryness to give compound 122. Yield: 0.59 g (83%). (M–H)⁻ Calc. for $C_5H_6{}^2H_3O_5{}^-$: 152.0639 found 152.0613 (7%); $C_5H_5{}^2H_4O_5{}^-$: 153.0701 found 153.0726 (90%).

Methyl α/β-D-ribofuranoside-1,2,3,4-$^2H_4$ (123). Compound 122 (7 g, 45.1 mmol) was treated with cc sulfuric acid in dry methanol as described for compound 1. Yield: 6.87 g (95%). (M–H)⁻ Calc. for $C_6H_8{}^2H_3O_5{}^-$: 166.0795 found 166.0778 (8%); $C_6H_7{}^2H_4O_5{}^-$: 167.0858 found 167.0843 (90%).

Methyl α/β-D-ribofuranoside-1,2,3,4,5,5'-$^2H_6$ (124). 24 h's treatment of compound 123 (1.12 g, 7 mmol) with deuterated Raney-nickel in $^2H_2O$ as described for compound 2 gave the fully deuterated sugar derivative 124. Yield: 0.89 g (78%). (M–H)⁻ Calc. for $C_6H_6{}^2H_5O_5{}^-$: 168.0921 found 168.0908 (12%); $C_6H_7{}^2H_4O_5{}^-$: 169.0983 found 169.0968 (85%).

1. (a) Jardetzky, O.; Roberts, G. C. K. *NMR in Molecular Biology*; Academic Press: New York, 1981; Chapter 13. (b) Wemmer, D. E.; Reid, B. R. *Ann. Rev. Phys. Chem.* 1985, 36, 105. (c) Wüthrich, K. *NMR of Proteins and Nucleic Acids*; Wiley: New York, 1986. (d) Reid, B. R. *Q. Rev. Biophys.* 1987, 20, 1. (e) Van de Ven, F. J. M.; Hilbers, C. W. *Eur. J. Biochem.* 1988, 178, 1. (f) Hosur, R. V.; Govil, G.; Miles, H. T. *Magn. Reson. Chem.* 1988, 26, 927.

2. (a) Ernst, R. R.; Bodenhausen, G.; Wokaun, A. *Principles of Nuclear Magnetic Resonance in One and Two Domensions*, Clarendon Press: Oxford, 1987. (b) Oppenheimer, N. J.; James, T. L. Eds. *Methods Enzymol.* 1989, 176, Chapter 1 & 2.

3. (a) Vuister, G. W.; Boelens, R. *J. Magn. Reson.* 1987, 73, 328. (b) Mooren, M. M. W.; Hilbers, C. W.; Van Der Marel, G. A.; Van Boom, J. H.; Wijmenga, S. S. *J. Magn. Reson.* 1991, 94, 101. (c) Majumdar, A.; Hosur, R. V. *J. Biomol. NMR*, 1991, 1, 205. (d) Sörensen, O. W. *J. Magn. Reson.* 1990, 90, 433.

4. Wüthrich, K., *NMR of Proteins and Nucleic Acids;* John Wiley & Sons, New York, 1986

5. (a) Neuhaus, D.; Williamson, M. P. *The Nuclear Overhauser Effect in Structural and Conformational Analysis;* VHC Publishers: New York, 1989; (b) James, T. L. *Current Opinion in Structural Biology*, 1, 1042 (1991); (c) Torda, A. E., Scheek, R. M., and van Gunsteren, W. F. *J. Mol. Biol.*, 214, 223 (1990); (d) Kaluarachchi, K, Meadows, R. P. and Gorenstein, D. G. *Biochemistry*, 30, 8785 (1991); (e) Pearlman, D. A. and Kollman, P. A., *J. Mol. Biol.* 220, 457 (1991).

6. (a) Brush, C. K.; Stone, M. P.; Harris, T. M. *Biochemistry* 1988, 27, 115. (b) Brush, C. K.; Stone, M. P.; Harris, T. M. *J. Am. Chem. Soc.* 1988, 110, 4405.

7. Schmidt, R. R.; Scholz, U; Schwille, D. *Chem. Ber.* 1968, 101, 590.

8. Schmidt, R. R.; Heermann, D.; Jung, K.-H. *Liebigs Ann. Chem.* 1974, 1856.

9. Dupre, M.; Gaudemer, A. *Tetrahedron Lett.* 1978, 2783.

10. Kintanar, A.; Alam, T. M.; Huang, W.-C.; Schindele, D. C.; Wemmer, D. E.; Drobny, G. *J. Am. Chem. Soc.* 1988, 110, 6367.

11. Berger, A.; Shaw, A.; Cadet, J. *Nucleosides & Nucleotides* 1987, 6, 395.

12. Ajmera, S.; Massof, S.; Kozarich, J. W. *J. Labelled Compd.* 1986, 23, 963.

13. Sinhababu, A. K.; Barrel, R. L.; Pochopin, N.; Borchardt, R. T. *J. Am. Chem. Soc.* 1985, 107, 7628.

14. Robins, M. J.; Samano, V.; Johnson, M. D. *J. Org. Chem.* 1990, 55, 410.

15. Fraser-Reid, B.; Radatus, B. *J. Am. Chem. Soc.* 1971, 93, 6342.

16. Radatus, B.; Yunker, M.; Fraser-Reid, B. *J. Am. Chem. Soc.* 1971, 93, 3086.

17. (a) David, S.; Eustache, J.; *Carbohyd. Res.* 1971, 16, 469. (b) David, S.; Eustache, J.; *Carbohyd. Res.* 1971, 20, 319.

18. Wong, M. Y. H.; Gray, G. R. *J. Am. Chem. Soc.* 1978, 100, 3548.

19. Pathak, T.; Bazin, H.; Chattopadhyaya, J. *Tetrahedron* 1986, 42, 5427.

20. Roy, S.; Hiyama, Y.; Torchia, D. A.; Cohen, J. S. *J. Am. Chem. Soc.* 1986, 108, 1675.

21. Wu, J.-C.; Bazin, H.; Chattopadhyaya, J. *Tetrahedron* 1987, 43, 2355.

22. Hodge, R. P.; Brush, C. K.; Harris, C. M.; Harris, T. M. *J. Org. Chem.* 1991, 56, 1553.

23. Hiyama, Y.; Roy, S.; Cohen, J. S.; Torchia, D. A. *J. Am. Chem. Soc.* 1989, 111, 8609.

24. (a) Alam, T. M.; Drobny, G. *Biochemistry* 1990, 29, 3421. (b) Alam, T. M.; Orban, J.; Drobny, G. *Biochemistry* 1990, 29, 9610. (c) Huang, W.-C.; Orban, J.; Kintanar, A.; Reid, B. R.; Drobny, G. P. *J. Am. Chem. Soc.* 1990, 112, 9059. (d) Alam, T. M.; Orban, J.; Drobny, G. P. *Biochemistry* 1991, 30, 9229.

25. (a) Kondo, N. S.; Danyluk, S. S. *J. Am. Chem. Soc.* 1972, 94, 5121. (b) Kondo, N. S.; Leung, A.; Danyluk, S. S. *J. Labelled Compd.* 1973, 9, 497. (c) Kondo, N. S.; Ezra, F.; Danyluk, S. S. *FEBS Lett.* 1975, 53, 213. (d) Kondo, N. S.; Danyluk, S. S. *Biochemistry*, 1976, 15, 756. (e) Lee, C.-H.; Ezra, F.; Kondo, N. S.; Sarma, R. H.; Danyluk, S. S. *Biochemistry*, 1976, 15, 3627. (f) Ezra, F. S.; Lee, C.-H.; Kondo, N. S.; Danyluk, S. S.; Sarma, R. H. *Biochemistry*, 1977, 16, 1977.

26. Yang, J. J.-H. *Diss. Abstr. Int. B.* 1980, 41, 1726.

27. (a) Koch, H. J.; Stuart, R. S. *Carbohydr. Res.* 1977, 59, C1. (b) Balza, F.; Cyr, N.; Hamer, G. K.; Perlin, A. S.; Koch, H. J.; Stuart, R. S. *Carbohydr. Res.* 1977, 59, C7. (c) Koch, H. J.; Stuart, R. S. *Carbohydr. Res.* 1978, 64, 127. (d) Koch, H. J.; Stuart, R. S.; *Carbohydr. Res.* 1978, 59, 341. (e) Balza, F.; Perlin, A. S. *Carbohydr. Res.* 1982, 107, 270. (f) Angyal, S. J.; Odier, L. *Carbohydr. Res.* 1983, 123, 13. (g) Wu, G. D.; Serianni, A. S.; Barker, R. *J. Org. Chem.* 1983, 48, 1750. (h) Angyal, S. J.; Stevens, J. D.; Odier, L. *Carbohydr. Res.* 1986, 157, 83. (i) Kline, P. C.; Serianni, A. S. *Magn. Reson. Chem.* 1988, 26, 120. (j) Kline, P-C.; Serianni, A. S. *Magn. Reson. Chem.* 1990, 28, 324.

28. Pathak, T.; Chattopadhyaya, J. *Tetrahedron* 1987, 43, 4227.

29. Robins, M. J.; Wilson, J. S.; Hansske, F. *J. Am. Chem. Soc.* 1983, 105, 4059.

30. (a) Sund, C.; Agback, P.; Koole, L. H.; Sandström, A.; Chattopadhyaya, J. *Tetrahedron* 1992, 48, 695. and references therein (b) Maltseva, T.; Sandström, A.; Zarytova, V.; Chattopadhyaya, J. manuscript in preparation.

31. (a) Vorbrüggen, H.; Höfle, G. *Chem. Ber.* 1981, 114, 1256. (b) Vorbrüggen, H.; Krolikiewicz, K.; Bennua, B. *Chem. Ber.* 1981, 114, 1234.

32. Barker, R.; Fletcher Jr., H. G. *J. Org. Chem.* 1961, 26, 4605.

33. (a) Mozingo, R. *Org. Synth.* 1985, 3, 181. (b) Augustine, R. L. "Catalytic Hydrogenation"; Marcell Dekker: NY, 1965; p 147.

34. Adkins, H.; Billica, H. R. *J. Am. Chem. Soc.* 1948, 70, 695.

35. Hoffer, M. *Chem. Ber.* 1960, 93, 2777.

36. Davoll, J.; Lowy, B. A. *J. Am. Chem. Soc.* 1951, 73, 1650.

37. Zou, R.; Robins, M. J. *Can. J. Chem.* 1987, 65, 1436.

38. Altermatt, R.; Tamm, C. *Helv. Chim. Acta* 1985, 68, 475.

39. Brown, E. L.; Belagaje, R.; Ryan, M. J.; Khorana, H. G. *Methods Enzymol.* 1979, 68, 109.

40. Markiewicz, W. T. *J. Chem. Research (S).* 1979, 24.

41. Van der Kerk, G. J. M.; Noltes, J. G.; Luijten, J. G. A. *J. Appl. Chem.* 1957, 7, 366.

42. Remaud, G.; Zhou, X.-X.; Chattopadhyaya, J.; Oivanen, M.; Lönnberg, H. *Tetrahedron* 1987, 43, 4453.

43. Reese, C. B. *Tetrahedron* 1978, 34, 3143.

44. (a) Sandström, A.; Kwiatkowski, M.; Chattopadhyaya, J. *Acta Chem. Scand.* 1985, B39, 273. (b) Chattopadhyaya, J.; Reese, C. B. *Tetrahedron Lett.* 1979, 5059. (c) Kwiatkowski, M.; Heikkilä, J; Björkman, S; Chattopadhyaya, J. *Chemica Scripta* 1983, 22, 30. (d) Zhou, X. X; Sandström, A.; Chattopadhya, J, *Chemica Scripta* 1986, 26, 241.

45. Jones, S. S.; Rayner, B.; Reese, C. B.; Ubasawa, A.; Ubasawa, M. *Tetrahedron* 1980, 36, 3075.

46. Reese, C. B.; Titmus, R. C.; Yau, L. *Tetrahedron Lett.* 1978, 2727.

47. (a) Stewart, W. E. *The Interferon System* 2nd Ed. Springer Verlag, New York 1981. (b) Lengyel, P. *Ann. Rev. Biochem.* 1982, 51, 251. (c) Johnston, M. I.; Torrence, P. F. In: Friedman, R. M.; Ed., Finter, N. B., Series Ed. *Interferon, Mechanisms of Production and Action* Elsevier Science, Amsterdam 1984, Vol. 3, Chapter 7., pp. 189–298.

48. Doornbos, J.; Den Hartog, J. A. J.; Van Boom, J. H.; Altona, C. *Eur. J. Biochem.* 1981, 116, 403.

49. (a) Chattopadhyaya, J. B. *Tetrahedron Lett.* 1980, 21, 4113. (b) Gioeli, C.; Kwiatkowski, M.; Öberg, B.; Chattopadhyaya, J. B. *Tetrahedron Lett.* 1981, 22, 1741. (c) Nyilas, A.; Vrang, L.; Drake, A.; Öberg, B.; Chattopadhyaya, J. *Acta Chem. Scand.* 1986, B40, 678.

50. Mitchell, T. N. *J. Organometal. Chem.* 1973, 59, 189.

51. Potter, P. E.; Pratt, L.; Wilkinson, G. *J. Chem. Soc.* 1964, 524.

52. Piantini, O. W.; Sorensen, O. W.; Ernst, R. R. *J. Am. Chem. Soc.* 1982, 104, 6800.

53. Bax, A.; Griffey, R. H.; Hawkins, B. L. *J. Magn. Reson.,* 1983, 55, 301.

54. Bax, A.; Morris, G. A. *J. Magn. Reson.,* 1981, 42, 501.

55. Holy, A. *Coll. Czech. Chem. Commun.* 1982, 47, 2786.

56. (a) Pfitzner, K. C.; Moffatt, J. G. *J. Am. Chem. Soc.* 1965, 87, 5661. (b) Craig, J. W.; Sternberg, E. D.; Jones, G. H.; Moffatt, J. G. *J. Org. Chem.* 1986, 51, 1258.

57. Jackson, E. L.; Hudson, C. S. Moffatt, J. G. *J. Am. Chem. Soc.* 1941, 63, 1229.

58. Topper, Y. J.; Stetten, D. *J. Biol. Chem.* 1951, 189, 191.

59. Aslani-Shotorbani, G.; Buchanan, J. G.; Edgar, A. LR.; Shahidi, P. K. *Carbohydr. Res.* 1985, 136, 37.

I claim:

1. Deuterated nucleoside units for RNA and DNA synthesis, according to the formula

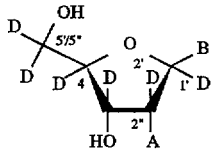

wherein

B is selected from the group consisting of adenine, guanine, thymine, cytosine and uracil and [bis ($^2$H-C8, C2)] adenine, [mono($^2$H-C8)]adenine, [mono($^2$H-C8, C2)]adenine, ($^2$H-C8)guanine, ($^2$H-C6)thymine, ($^2$H$_3$-C5-Me)thymine, [bis($^2$H-C6,$^2$H$_3$-C5-Me)]thymine, [bis($^2$H-C6,C5)]cytosine, ($^2$H-C5)cytosine, ($^2$H-C6) cytosine, ($^2$H-C6)cytosine, ($^2$H-C6)uracil, ($^2$H-C5) uracil, [bis($^2$H-C6,C5)]uracil and derivatives thereof, and A=hydroxyl or deuterium, and wherein the percentage of deuteration expressed as atom % $^2$H at each carbon of the sugar unit is sufficient for essentially eliminating resonance from said sugar unit in Nuclear Magnetic Resonance experiments performed on DNA or RNA oligo-/polymers, synthesized from (i) deuterated nucleoside units as defined above, and (ii) at least one non-deuterated nucleoside unit.

2. Deuterated nucleoside for RNA and DNA synthesis, as claimed in claim 1, wherein the percentage of deuteration expressed as atom % at each respective carbon site is the following:

C1'>17%, C2'>95%, C3'>95%, C4'>80%, C5'>95%, C5">95%, A (=$^2$H)>95%.

3. Deuterated nucleoside units as claimed in claim 1, with formulas:

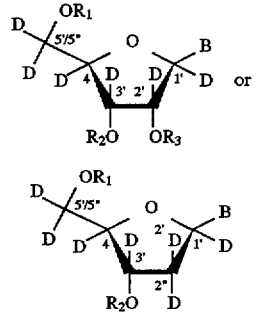

wherein the derivatives of said nucleobases B in claim 1 include: for Uracil:

N$^3$-Benzoyl, N$^3$-(4-toluoyl), N$^3$-(2-toluoyl), N$^3$-(4-anisoyl); N$^3$-(4-chlorobenzoyl), N$^3$-(2,2,2-trichloro-t-butyloxycarbonyl), N$^3$-(triphenylmethanesulfenyl), N$^3$-(butylthio-carbonyl), N$^3$-(methoxyethoxymethyl), O$^4$-(2-Nitrophenyl), O$^4$-(2-(4-cyanophenyl)-ethyl), O$^4$-(2-(4-nitrophenyl)-ethyl), O$^4$-phenyl, O$^4$-2-methylphenyl, O$^4$-4-methylphenyl, O$^4$-(2,4-dimethylphenyl), O$^4$-3-chlorophenyl, O$^4$-(2-(4-nitrophenylsulfonyl)-ethyl), O$^4$-(6-methyl-3-pyridyl), N$^3$-(4-nitrophenylethoxycarbonyl), O$^4$-(4-methyl-3-pyridyl), O$^4$-2,4,6-trimethylphenyl, for Cytosine:

$N^4$-Anisoyl, $N^4$-benzoyl, $N^4$-3,4-dimethylbenzoyl, $N^4$-acetyl, $N^4$-phenoxyacetyl, $N^4$-dimethylaminomethylene, $N^4$-benzyloxycarbonyl, $N^4$-levulinoyl, $N^4$-isobutyryl, $N^4$-(2-nitrophenylsulfenyl), $N^4$-isobutoxycarbonyl, $N^4$-(2,2,2-trichloro-t-butyloxycarbonyl), $N^4$-(9-fluorenylmethoxycarbonyl), $N^4$-(N-methyl-2-pyrrolidine amidine), $N^4$-(N,N-di-n-butylformamidine), $N^4$-(3-methoxy-4-phenoxybenzoyl), $N^4$-(isopropoxyacetyl), $N^4$-(2-(tertbutyldiphenylsilyloxymethyl)-benzoyl), $N^4$-(phenylsulfonylethoxycarbonyl) $N^4$-(4-chlorophenylsulfonylethoxycarbonyl), $N^4$-(2-chlorophenylsulfonylethoxycarbonyl), $N^4$-(4-nitrophenylethoxycarbonyl), $N^4$-2-(acetoxymethyl) benzoyl, for Adenine:

$N^6$-Di-n-butylformamidine, $N^6$-benzoyl, $N^6$-succinyl, $N^6,N^6$-phthaloyl, $N^6$-(4,5-dichlorophthaloyl), $N^6$-tetrachlorophthaloyl, $N^6$-(2-(4-nitrophenyl)-ethoxycarbonyl), $N^6$-phenoxyacetyl, $N^6$-(9-fluorenylmethoxycarbonyl), $N^6$-(3-chlorobenzoyl), $N^6$-anisoyl), $N^6$-(4-tertbutylbenzoyl), $N^6$-phenoxycarbonyl, $N^6$-benzyloxycarbonyl, $N^6$-isobutoxycarbonyl, $N^6$-(2,2,2-trichloro-t-butyloxycarbonyl), $N^6$-dimethylacetamidine, $N^6$-(2-nitrophenylsulfenyl), $N^6$-dimethylaminomethylene, $N^6$-di-n-butylaminomethylene, $N^6$-(N-methyl-2-pyrrolidine amidine), $N^6$-(N,N-di-n-butylformamidine), $N^6$-(3-methoxy-4-phenoxybenzoyl), $N^6$-isopropoxyacetyl, $N^6$-(2-(tertbutyldiphenylsilyloxymethyl)-benzoyl), $N^6$-phenylsulfonylethoxycarbonyl, $N^6$-(4-chlorophenylsulfonylethoxycarbonyl), $N^6$-(2-chlorophenylsulfonylethoxycarbonyl), $N^6$-(4-nitrophenylethoxycarbonyl), $N^6$-2-(acetoxymethyl) benzoyl, $N^6$-m-chlorobenzoyl, for Guanine:

$N^2$-Isobutyryl, acetyl, $N^2$-(4-tertbutylbenzoyl), $N^2$-benzyloxycarbonyl, $N^2$-phenoxyacetyl, $N^2$-benzoyl, $N^2$-levulinoyl, $N^2$-(2-nitrophenylsulfenyl), $N^2$-(9-fluorenylmethoxycarbonyl), $N^2$-(2,2,2-trichloro-t-butyloxycarbonyl), $N^2$-propionyl, $N^2$-dimethylaminomethylene, $N^2$-dimethylacetamidine, $N^2$-(N-methyl-2-pyrrolidineamidine), $N^2$-(N,N-di-n-butylformamidine), $N^2$-phenylacetyl, $N^2$-(1,2-diisobutyryloxyethylene), $N^2$-(3-methoxy-4-phenoxybenzoyl), $N^2$-methoxyacetyl, chlorophenoxyacetyl, $N^2$-isopropoxy-acetyl, $N^2$-(2-(tertbutyldiphenylsilyloxymethyl)-benzoyl), $N^2$-phenylsulfonylethoxycarbonyl, $N^2$-4-chlorophenylsulfonylethoxycarbonyl, $N^2$-2-(acetoxymethyl) benzoyl, $N^2$-3,4-dichlorobenzoyl, $O^6$-Benzyl, $O^6$-(2-(4-nitrophenyl)-ethyl), $O^6$-(2-nitrophenyl), $O^6$-(4-nitrophenyl), $O^6$-diphenylcarbamoyl, $O^6$-(3,4-dimethoxybenzyl), $O^6$-(3,5-dichlorophenyl), $O^6$-(2-cyanoethyl), $O^6$-(2-trimethylsilylethyl), $O^6$-phenylthioethyl, $O^6$-(4-nitrophenylthioethyl), $O^6$-butylthiocarbonyl, $O^6$-(6-methyl-3-pyridyl), $O^6$-(2-(4-nitrophenylsulfonyl)-ethyl), $O^6$-(4-methyl-3-pyridyl), $N^2$-(4-nitrophenylethoxycarbonyl), $O^6$-allyl or any combination of these protecting groups for $O^6$, $N^2$-dis protection, for Thymine:

$O^4$-phenyl, $O^4$-(2-(4-nitrophenyl)-ethyl), $O^4$-(2-(4-nitro phenylsulfonyl)-ethyl), $O^4$-2-methylphenyl, $O^4$-4-methyl phenyl, $O^4$-(2,4-dimethylphenyl), $N^3$-benzoyl, $N^3$-(4-anisoyl), $N^3$-(4-toluoyl), $N^3$-(2-toluoyl), $R^1$=5'-protecting group:

9-Fluorenylmethoxycarbonyl, 4-chlorophenylsulfonylethoxy carbonyl, 4-nitrophenylsulfonyl-ethoxycarbonyl, phenyl sulfonylethoxycarbonyl, 2,2,2-tribromoethoxycarbonyl, levulinyl, 4,4',4"-tris(4,5-dichlorophtalimide)trityl, 4,4',4"-tris(benzoyloxy) trityl, 4,4',4"-tris(levulinyl oxy)trityl, p-anisyl-1-naphtylphenylmethyl, di-p-anisyl-1-naphtylmethyl, p-tolyldiphenylmethyl, 3-(imidazolylmethyl) -4,4'-dimethoxytrityl, methoxyacetyl, chloroacetyl, phenoxyacetyl, 4-chlorophenoxyacetyl, trityloxyacetyl, β-benzoylpropionyl, isobutyloxycarbonyl, 4-nitrobenzyloxy carbonyl, 2-(methylthiomethoxymethyl)-benzoyl, 2-(isopropylthiomethoxymethyl) benzoyl, 4-(methylthiomethoxy butyryl, p-phenylazophenyloxycarbonyl, 2,4-dinitrophenyl ethoxycarbonyl, pivaloyl, 2-dibromomethylbenzoyl, tert-butyldimethylsilyl, 4,4'-dimethoxytrityl, 4'-monomethoxy trityl, 4-decyloxytrityl, 4-hexadecyloxytrityl, trityl, 1,1-bis-(4-methoxyphenyl)-1'-pyrenyl, 9-phenylxanthen-9-yl, 9-phenylthioxanthen-9-yl, 7-chloro-9-phenylthioxan then-9-yl, 9-(4-methoxyphenyl)-xanthen-9-yl, 9-(4-octadecyloxyphenyl)-xanthen-9-yl $R_2$=H, succinate or any of $R_3$ below $R_3$=2'-succinate or 2'-protecting group as follows:

tetrahydrofuranyl, tetrahydropyranyl, 4-methoxytetrahydro pyran-4-yl, 9-phenylxanthen-9-yl, 1-((2-chloro-4-methyl) phenyl)-4-methoxypiperidin-4-yl, 1-(2-fluorophenyl)-4-methoxypiperidin-4-yl, 4,4'-dimethoxytrityl, 1,3-benzo dithiol-2-yl, (2-(methylthio)phenyl)thiomethyl, 7-chloro-9-(p-anisyl)thioxanthen-9-yl, 7-chloro-9-phenylthioxanthen -9-yl, 9-phenylthioxanthen-9-yl, o-nitrobenzyl, 4-methoxybenzyl, 3,4-domethoxybenzyl, 1-(2-chloroethoxy) ethyl, (1-methyl-1-methoxy)ethyl, 3-methoxy-1,5-dicarbo methoxypentan-3-yl, p-nitrophenylethylsulfonyl, p-cyanoethylsulfonyl, carbomethoxyethylsulfonyl, tert-butyldimethylsilyl, triisopropylsilyl.

4. Nucleotide units based on the nucleoside units as claimed in claim 2, and defined according to the formula:

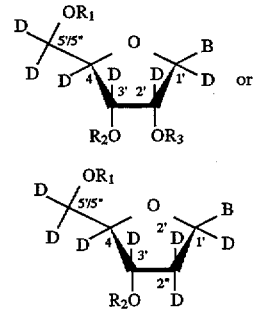

wherein $R_2$=3'-phosphate, H-phosphonate or phosphite as follows:

(a) 3'-phosphodiesters: 2,2,2-Trichloroethyl, 2,2,2-tribromoethyl, 2-cyanoethyl, benzyl, 4-chlorophenyl, 4-nitrophenylethyl, 2-chlorophenyl, 2-diphenylmethylsilyl ethyl, phenylthio;

(b) 3'-phosphotriesters: 2-Cyanoethyl-4-chlorophenyl, 2-cyanoethyl-2-cyanoethyl, 2-cyanoethyl-2-chlorophenyl, phenylsulfonylethyl-2-chlorophenyl, 9-fluorenylmethyl-2-chlorophenyl, 9-fluorenylmethyl-4-chlorophenyl, phenylsulfonylethyl-4-chlorophenyl, phenylsulfonylethyl-2-chloro phenyl, 2,2,2-tribromoethyl-4-chlorophenyl, 2,2,2-tribromo ethyl-2-chlorophenyl, 2,2,2-trichloroethyl-4-chlorophenyl, 2,2, 2-trichloroethyl-2-chlorophenyl, 2-cyanoethyl-2-chloro-4-tritylphenyl, 2,2,2-tribromoethyl-2-chloro-4-tertbutyl phenyl, 4-nitrophenyl-phenyl, 2,4-dinitrobenzyl-2-chloro phenyl, 2,4-dinitrobenzyl-4-chlorophenyl; S,S-diphenyl phosphorodithioate; 2-chlorophenyl-phosphoranilidate, phenylphosphoranilidate, (c) 3'-halophosphites (chloro or bromo): phenylsulfonylethoxy, methylsulfonylethoxy, 2-(isopropyl sulfonyl)-ethoxy, 2-(tertbutylsulfonyl)-ethoxy, benzyl sulfonylethoxy, 4-nitrobenzylsulfonylethoxy, 9-fluorenyl methoxy, 2-(4-nitrophenyl)-ethoxy, methoxy, 2-cyano-1,1-dimethylethoxy, 2,2,2-trichloro-1,1-dimethylethoxy, 2,2,2-trichloroethoxy, 2-cyanoethoxy, 2-cyano-1-methylethoxy, 2-cyano-1,1-dimethylethoxy-, 2-(4-nitrophenyl)-ethoxy, 2(2-pyridyl)-ethoxy, 2-methylbenzyloxy, 4-chlorobenzyloxy, 2-chlorobenzyloxy, 2,4-dichlorobenzyloxy, 4-nitrobenzyloxy, allyloxy, phenoxy, 4-nitrophenoxy, pentafluorophenyoxy, pentachlorophenoxy, 2,4,5-trichlorophenoxy, 2-bromophenoxy, 4-bromophenoxy, 2-methylphenoxy, 2,6-dimethylphenoxy, 2,4-nitrophenoxy, 1,1,1,3,3,3-hexafluoro-2-propyloxy, 2-chlorophenoxy (d) 3'-phosporamidites: phenylsulfonylethoxydimethylamino, methylsulfonylethoxy-morpholino, 2-(isopropylsulfonyl)-ethoxy-morpholino, 2-(tertbutylsulfonyl)-ethoxy-morpholino, benzylsulfonylethoxy-morpholino, 4-nitrobenzylsulfonylethoxy-morpholino, 9-fluorenylmethoxymorpholino, 2-(4-nitrophenyl)-ethoxy-morpholino, 2-(4-nitrophenyl)-ethoxy-hexahydroazepine, 2-(4-nitrophenyl)ethoxy-octahydrazonine, 2-(4-nitrophenyl)-ethoxyazacyclo tridecane, methoxy-pirrolidino, methoxy-piperidino, methoxy-diethylamino, methoxy-diisopropilamino, methoxy-2,2,6,6-tetramethyl-N-piperidino, methoxy-morpholino, 2-cyano-1,1-dimethylethoxy-morpholino, 2,2,2-trichloro-1,1-dimethylethoxydimethylamino, 2,2, 2-trichloro-1,1-dimethyl ethoxydiethylamino, 2,2,2-trichloro-1,1-dimethylethoxy-diisopropylamino, 2,2,2-trichloro-1,1-dimethylethoxymorpholino, 2,2,2-trichloroethoxydimethylamino, 2-cyanoethoxy diethylamino, 2-cyanoethoxydiisopropylamino, 2-cyanoethoxy morpholino, 2-cyano-1-methylethoxy-diethylamino, 2-cyano-1,1-dimethylethoxydiethylamino, 2-cyano-1,1-dimethylethoxy-diisopropylamino, methylsulfonylethoxydiethylamino, methylsulfonylethoxydiisopropylamino, 2,2,2-trichloroethoxydiisopropylamino, 2,2,2-trichloro-1,1-dimethylethoxydiisopropylamino, 2-(4-nitrophenyl)-ethoxy-diisopropyl amino, 2(2-pyridyl)-ethoxy-diisopropylamino, 2(4-pyridyl) ethoxydiisopropylamino, 2-methylbenzyloxy-diisopropyl amino, 4-chlorobenzyloxy-diisopropylamino, 2-chlorobenzyl oxydiisopropylamino, 2,4-dichlorobenzyloxy-diisopropyl amino, 4-nitrobenzyloxydiisopropylamino, allyloxydiiso propylamino, allyloxydimethylamino, phenoxydiethylamino, 4-nitrophenoxydiethylamino, pentafluorophenoxydiethyl amino, pentachlorophenoxy-diethylamino, 2,4,5-trichloro phenoxydiethylamino, 2-bromophenoxydiethylamino, 4-bromophenoxydiethylamino, 2-methylphenoxydiethylamino, 2,6-dimethylphenoxydiethylamino, 2,4-nitrophenoxy diethylamino, 1,1,1,3,3,3-hexafluoro-2-propyloxydiiso propylamino, 2-chlorophenoxy-morpholino, bis (diisopropyl amino), bis(diethylamino), bis (morpholino).

5. 5'-triphosphates of deuterated nucleoside units as claimed in claim 2 or 4 with general formulae:

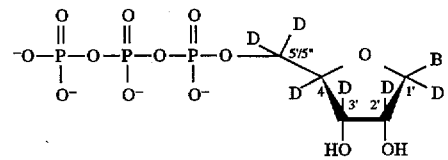

6. Methyl-α/β-1,2,3,4,5,5,'-$^2$H$_6$-ribofuranoside.

7. Methyl-α/β-1,2,3,4,5,5'-$^2$H$_6$-ribofuranoside, wherein the percentage of deuteration expressed as atom % at the respective carbons is as follows:

C1>17%, C2>95%, C3>95%, C4>80%, C5>95%, C5'>95%.

8. A method of preparing methyl-α/β-1,2,3,4,5,5'-$^2$H$_6$-ribofuranoside, comprising heating an epimeric mixture of methyl-α/β-ribofuranoside, $^2$H$_2$O and deuterated Raney Nickel under reflux and exclusion of atmospheric moisture, for at least 3 days.

9. The method as claimed in claim 8, wherein at least 10 ml $^2$H$_2$O/g of methyl-α/β-ribofuranoside is used.

10. In a method for the preparation of RNA and DNA oligo-/polymers suitable for NMR-window experiments, the improvement wherein a compound according to any of claims 1–7 is used.

11. Deuterated nucleoside according to claim 1 according to the formula

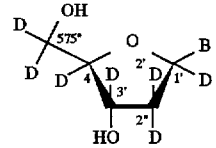

wherein
R=H or OH: and
B is Adenine-9-yl, or
Guanine-9-yl, or
Cytosine-1-yl, or
Urazil-1-yl, or
Thymine-1-yl.

12. In a method for the preparation of RNA and DNA oligo-/polymers suitable for NMR-window experiments, the improvement wherein a compound according to claim 11 is used.

13. Deuterated nucleoside units for RNA and DNA synthesis according to claim 2, wherein the percentage of deuteration at each respective carbon site is the following:

C1'>20%, C2'>97%; C3'>97%, C4'>80%, C5'>97%, C5">97%, A=$^2$H>97%.

14. Deuterated nucleoside units for RNA and DNA synthesis according to claim 13, wherein the percentage of deuteration at each respective carbon site is the following:

C1'>97%, C2'>97%; C3'>97%, C4'>97%, C5'>97%, C5">97%, A=$^2$H>97%.

15. Methyl-α/β-1,2,3,4,5,5'-$^2$H$_6$-ribofuranoside according to claim 7 wherein the percentage of deuteration expressed as atom % $^2$H at the respective carbons is as follows:

C1>20%, C2>97%, C3>97%, C4>80%, C5>97%, C5'>97%.

16. Methyl-α/β-1,2,3,4,5,5'-$^2$H$_6$-ribofuranoside according to claim 15 wherein the percentage of deuteration expressed as atom % $^2$H at the respective carbons is as follows:

C1>97%, C2>97%, C3>97%, C4>97%, C5>97%, C5'>97%.

17. The method as claimed in claim 8 wherein the Raney Nickel catalyst is prepared by adding Ni—Al alloy to NaOH solution under stirring while maintaining the temperature at 50°±4° C. and continuing heating for approximately 30 minutes;

continuing heating at 50° C. for another 60 minutes;

allowing the solution formed to cool at room temperatures;

washing the particles until the pH in the liquid is between 6.5 and 7.0;

adding $^2$H$_2$O to the particles under stirring for approximately 30 minutes and then removing the liquid;

repeating said adding, stirring and removing at least five times.

18. Deuterated nucleoside units as claimed in claims 2 or 13 or 14 with formulas:

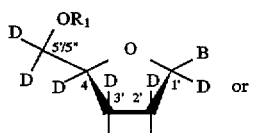

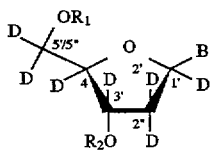

wherein the derivatives of said nucleobases B in claim 1 include:

for Uracil:

N$^3$-Benzoyl, N$^3$-(4-toluoyl), N$^3$-(2-toluoyl), N$^3$-(4-anisoyl), N$^3$-(4-chlorobenzoyl), N$^3$-(2,2,2-trichloro-t-butyloxycarbonyl), N$^3$-(triphenylmethanesulfenyl), N$^3$-(butylthio-carbonyl), N$^3$-(methoxyethoxymethyl), O$^4$-(2-Nitrophenyl), O$^4$-(2-(4-cyanophenyl)-ethyl), O$^4$-(2-(4-nitrophenyl)-ethyl), O$^4$-phenyl, O$^4$-2-methylphenyl, O$^4$-4-methylphenyl, O$^4$-(2,4-dimethylphenyl), O$^4$-3-chlorophenyl, O$^4$-(2-(4-nitrophenylsulfonyl)-ethyl), O$^4$-(6-methyl-3-pyridyl), N$^3$-(4-nitrophenylethoxycarbonyl), O$^4$-(4-methyl-3-pyridyl), O$^4$-2,4,6-trimethylphenyl, oxycarbonyl, N$^4$-levulinoyl, N$^4$-isobutyryl, N$^4$-(2-nitrophenylsulfenyl), N$^4$-isobutoxycarbonyl, N$^4$-(2,2-trichloro-t-butyloxycarbonyl), N$^4$-(9-fluorenylmethoxycarbonyl), N$^4$-(N-methyl-2-pyrrolidine amidine), N$^4$-(N,N-di-n-butylformamidine), N$^4$-(3-methoxy-4-phenoxybenzyl), N$^4$-(isopropoxyacetyl), N$^4$-(2-(tertbutyldiphenylsilyloxymethyl)-benzoyl), N$^4$-(phenylsulfonylethoxycarbonyl), N$^4$-(4-chlorophenylsulfonylethoxycarbonyl), N$^4$-(2-chlorophenylsulfonylethoxycarbonyl), N$^4$-(4-nitrophenylethoxycarbonyl), N$^4$-2-(acetoxymethyl) benzoyl, for Adenine:

N$^6$-Di-n-butylformamidine, N$^6$-benzoyl, N$^6$-succinyl, N$^6$,N$^6$-phthaloyl, N$^6$-(4,5-dichlorophthaloyl), N$^6$-tetrachlorophthaloyl, N$^6$-(2-(4-nitrophenyl)-ethoxycarbonyl), N$^6$-phenoxyacetyl, N$^6$-(9-fluorenylmethoxycarbonyl), N$^6$-(3-chlorobenzoyl), N$^6$-anisoyl), N$^6$-(4-tertbutylbenzoyl), N$^6$-phenoxycarbonyl, N$^6$-benzyloxycarbonyl, N$^6$-isobutoxycarbonyl, N$^6$-(2,2,2-trichloro-t-butyloxycarbonyl), N$^6$-dimethylacetamidine, N$^6$-(2-nitrophenylsulfenyl), N$^6$-dimethylaminomethylene, N$^6$-di-n-butylaminomethylene, N$^6$-(N-methyl-2-pyrrolidine amidine), N$^6$-(N,N-di-n-butylformamidine), N$^6$-(3-methoxy-4-phenoxybenzoyl), N$^6$-isopropoxyacetyl, N$^6$-(2-(tertbutyldiphenylsilyloxymethyl)-benzoyl), N$^6$-phenylsulfonylethoxycarbonyl, N$^6$-(4-chlorophenylsulfonylethoxycarbonyl), N$^6$-(2-chlorophenylsulfonylethoxycarbonyl), N$^6$-(4-nitrophenylethoxycarbonyl), N$^6$-2-(acetoxymethyl) benzoyl, N$^6$-m-chlorobenzoyl;

for Guanine:

N$^2$-Isobutyryl, acetyl, N$^2$-(4-tertbutylbenzyl), N$^2$-benzyloxycarbonyl, N$^2$-phenoxyacetyl, N$^2$-benzoyl, N$^2$-levulinoyl, N$^2$-(2-nitrophenylsulfenyl), N$^2$-(9-fluorenylmethoxycarbonyl), N$^2$-(2,2,2-trichloro-t-butyloxycarbonyl), N$^2$-propionyl, N$^2$-dimethylaminomethylene, N$^2$-dimethylacetamidine, N$^2$-(N-methyl-2-pyrrolidineamidine), N$^2$-(N,N-di-n-butyl-formamidine), N$^2$-phenylacetyl, N$^2$-(1,2-diisobutyryloxyethylene), N$^2$-(3-methoxy-4-phenoxybenzoyl), N$^2$-methoxyacetyl, chlorophenoxyacetyl, N$^2$-isopropoxy-acetyl, N$^2$-(2-(tertbutyldiphenylsilyloxymethyl)-benzoyl), N$^2$-phenylsulfonylethoxycarbonyl, N$^2$-4-chlorophenylsulfonylethoxycarbonyl, N$^2$-2-(acetoxymethyl) benzoyl, N$^2$-3,4-dichlorobenzoyl, O$^6$-Benzyl, O$^6$-(2-(4-nitrophenyl)-ethyl), O$^6$-(2-nitrophenyl), O$^6$-(4-nitrophenyl), O$^6$-diphenylcarbamoyl, O$^6$-(3,4-dimethoxybenzyl), O$^6$-(3,5-dichlorophenyl), O$^6$-(2-cyanoethyl), O$^6$-(2-trimethylsilylethyl), O$^6$-phenylthioethyl, O$^6$-(4-nitrophenylthioethyl), O$^6$-butylthiocarbonyl, O$^6$-(6-methyl-3-pyridyl), O$^6$-(2-(4-nitrophenylsulfonyl)-ethyl), O$^6$-(4-methyl-3-pyridyl), N$^2$-(4-nitrophenylethoxycarbonyl), O$^6$-allyl or any combination of these protecting groups for O$^6$, N$^2$-dis protection;

for Thymine:

O$^4$-Phenyl, O$^4$-(2-(4-nitrophenyl)-ethyl), O$^4$-(2-(4-nitro phenylsulfonyl)-ethyl), O$^4$-2-methylphenyl, O$^4$-4-methyl phenyl, O$^4$-(2,4-dimethylphenyl), N$^3$-benzoyl, N$^3$-(4-anisoyl), N$^3$-(4-toluoyl), N$^3$-(2-toluoyl), R$_1$=5'-protecting group:

9-Fluorenylmethoxycarbonyl, 4-chlorophenylsulfonylethoxy carbonyl, 4-nitrophenylsulfonyl-ethoxycarbonyl, phenyl sulfonylethoxycarbonyl, 2,2,2-tribromoethoxycarbonyl, levulinyl, 4,4',4"-tris(4,5-dichlorophtalimido)trityl, 4,4',4"-tris(benzoyloxy) trityl, 4,4',4"-tris(levulinyl oxy)trityl, p-anisyl-1-naphtylphenylmethyl, di-p-anisyl-1-naphtylmethyl, p-tolyldiphenylmethyl, 3-(imidazolylmethyl) -4,4'-dimethoxytrityl, methoxyacetyl, chloroacetyl, phenoxyacetyl, 4-chlorophenoxyacetyl, trityloxyacetyl, β-benzoylpropionyl, isobutyloxycarbonyl, 4-nitrobenzyloxy carbonyl, 2-(methylthiomethoxymethyl)-benzoyl, 2-(iso propylthiomethoxymethyl) benzoyl, 4-(methylthiomethoxy butyryl, p-phenylazophenyloxycarbonyl, 2,4-dinitrophenyl ethoxycarbonyl, pivaloyl, 2-dibromomethylbenzoyl, tert-butyldimethylsilyl, 4,4'-dimethoxytrityl, 4'-monomethoxy trityl, 4-decyloxytrityl, 4-hexadecyloxytrityl, trityl, 1,1-bis-(4-methoxyphenyl)-1'-pyrenyl, 9-phenylxanthen-9-yl, 9-phenylthioxanthen-9-yl, 7-chloro-9-phenylthioxanthen-9-yl, 9-(4-methoxyphenyl)-xanthen-9-yl, 9-(4-octadecyloxyphenyl)-xanthen-9-yl $R_2$=H, succinate or any of $R_3$ below $R_3$=2'-succinate or 2'-protecting group as follows:

tetrahydrofuranyl, tetrahydropyranyl, 4-methoxytetrahydro pyran-4-yl, 9-phenylxanthen-9-yl, 1-((2-chloro-4-methyl) phenyl)-4-methoxypiperidin-4-yl, 1-(2-fluorophenyl)-4-methoxypiperidin-4-yl, 4,4'-dimethoxytrityl, 1,3-benzo dithiol-2-yl, (2-(methylthio)phenyl)thiomethyl, 7-chloro-9-(p-anisyl)thioxanthen-9-yl, 7-chloro-9-phenylthioxanthen -9-yl, 9-phenylthioxanthen-9-yl, o-nitrobenzyl, 4-methoxybenzyl, 3,4-domethoxybenzyl, 1-(2-chloroethoxy) ethyl, (1-methyl-1-methoxy)ethyl, 3-methoxy-1,5-dicarbo methoxypentan-3-yl, p-nitrophenylethylsulfonyl, p-cyanoethylsulfonyl, carbomethoxyethylsulfonyl, tert-butyldimethylsilyl, triisopropylsilyl.

19. The method as claimed in claim 18 wherein at least 10 ml $^2H_2O$/g of methyl-α/β-ribofuranoside is used.

* * * * *